United States Patent
Gori

(10) Patent No.: US 11,739,287 B2
(45) Date of Patent: Aug. 29, 2023

(54) CLEANING COMPOSITIONS AND USES THEREOF

(71) Applicant: Novozymes A/S, Bagsvaerd (DK)

(72) Inventor: Klaus Gori, Dyssegaard (DK)

(73) Assignee: Novozymes A/S, Bagsvaerd (DK)

( * ) Notice: Subject to any disclaimer, the term of this patent is extended or adjusted under 35 U.S.C. 154(b) by 199 days.

(21) Appl. No.: 17/188,017

(22) Filed: Mar. 1, 2021

(65) Prior Publication Data

US 2021/0222090 A1 Jul. 22, 2021

Related U.S. Application Data

(62) Division of application No. 16/500,424, filed as application No. PCT/EP2018/056730 on Mar. 16, 2018, now Pat. No. 10,968,416.

(30) Foreign Application Priority Data

Apr. 6, 2017 (EP) .................................. 17165343

(51) Int. Cl.
*C12N 9/22* (2006.01)
*C11D 3/386* (2006.01)
*C11D 11/00* (2006.01)

(52) U.S. Cl.
CPC ...... *C11D 3/38636* (2013.01); *C11D 3/38645* (2013.01); *C11D 11/0017* (2013.01)

(58) Field of Classification Search
CPC .................................. C12N 9/248; C12N 9/22
See application file for complete search history.

(56) References Cited

U.S. PATENT DOCUMENTS

2020/0199498 A1   6/2020   Gori

FOREIGN PATENT DOCUMENTS

| WO | 2014/087011 A1 | 6/2014 |
|---|---|---|
| WO | 2014/124927 A2 | 8/2014 |
| WO | 2015/155350 A1 | 10/2015 |
| WO | 2015/155351 A1 | 10/2015 |
| WO | 2015/166075 A1 | 11/2015 |
| WO | 2015/181286 A1 | 12/2015 |
| WO | 2015/181287 A1 | 12/2015 |
| WO | 2015/181827 A1 | 12/2015 |
| WO | 2016/162556 A2 | 10/2016 |
| WO | 2016/162558 A1 | 10/2016 |
| WO | 2017/001471 A1 | 1/2017 |
| WO | 2017/001472 A1 | 1/2017 |
| WO | 2017/059802 A1 | 4/2017 |
| WO | 2017/060475 A2 | 4/2017 |

*Primary Examiner* — Tekchand Saidha
(74) *Attorney, Agent, or Firm* — Elias Lambiris

(57) ABSTRACT

The present invention relates to compositions such as cleaning compositions comprising a mix of enzymes. The invention further relates, use of compositions comprising such enzymes in cleaning processes.

20 Claims, No Drawings
Specification includes a Sequence Listing.

CLEANING COMPOSITIONS AND USES THEREOF

CROSS-REFERENCE TO RELATED APPLICATIONS

This application is a divisional of U.S. application Ser. No. 16/500,424 filed Oct. 3, 2019, now pending, which is a 35 U.S.C. 371 national application of international application no. PCT/EP2018/056730 filed Mar. 16, 2018, which claims priority under 35 U.S.C. 119 of European application no. 17165343.9 filed Apr. 6, 2017. The content of each application is fully incorporated herein by reference.

REFERENCE TO A SEQUENCE LISTING

This application contains a Sequence Listing in computer readable form, which is incorporated herein by reference.

BACKGROUND OF THE INVENTION

The present invention relates to compositions such as cleaning compositions comprising a mix of enzymes. The invention further relates, use of compositions comprising such enzymes in cleaning processes and/or for deep cleaning of biofilm soiling, methods for removal or reduction of biofilm related soiling.

DESCRIPTION OF THE RELATED ART

Enzymes have been used in detergents for decades. Usually a cocktail of various enzymes is added to detergent compositions. The enzyme cocktail often comprises various enzymes, wherein each enzyme targets it specific substrate, e.g., amylases are active towards starch stains, proteases on protein stains and so forth. Textiles surface and hard surfaces, such as dishes or the inner space of a laundry machine enduring a number of wash cycles, become soiled with many different types of soiling which may compose of proteins, grease, starch etc. One type of soiling may be organic matter, such as biofilm, EPS, etc. Organic matter composes different molecules such as polysaccharides, extracellular DNA (eDNA), and proteins. Some organic matter composes an extracellular polymeric matrix, which may be sticky or glueing, which when present on textile, attracts soils and may course redeposition or backstaining of soil resulting in a greying of the textile. Additionally, organic matters such as biofilms often cause malodor issue as various malodor molecules can be adhered by the polysaccharides, extracellular DNA (eDNA), and proteins in the complex extracellular matrix and be slowly released out to cause consumer noticeable malodor issue. There is still a need for cleaning compositions, which effectively prevent, reduce or remove components of organic stains, e.g., biofilm, an effect described in the present application as "deep cleaning". The present invention provides new compositions fulfilling such need.

SUMMARY OF THE INVENTION

A first aspect of the present invention, relates to a cleaning composition comprising a DNase, at least one carbohydrase and a cleaning component, wherein the carbohydrase is a cellulase, an amylase, a mannanase or a xylanase. Another aspect of the invention relates to a cleaning composition comprising at least 0.001 ppm DNase and at least 0.001 ppm carbohydrase and a cleaning component, wherein the cleaning component is selected from
  a. 0.1 to 15 wt. %, e.g., from about 1% to about 40% of at least one a surfactant;
  b. 0.5 to 20 wt. %, e.g., from about 5% to about 50% of at least one builder; and
  c. 0.01 to 10 wt. %, e.g., from about 1% to about 20% of at least one bleach component.

The invention further relates to the use of a composition for deep cleaning of an item, wherein the item is a textile or a surface. The invention further relates to the use of a cleaning composition comprising a DNase, at least one carbohydrase and a cleaning component, wherein the carbohydrase is a cellulase, an amylase, a mannanase or a xylanase. The invention further relates to a method of formulating a cleaning composition comprising adding a DNase, a carbohydrase and at least one cleaning component. The invention further relates to a kit intended for deep cleaning, wherein the kit comprises a solution of an enzyme mixture comprising a DNase and a carbohydrase, wherein the carbohydrase is a cellulase, an amylase, a mannanase or a xylanase. The invention further relates to a method of deep cleaning an item, comprising the steps of: a) contacting the item with a cleaning composition comprising a DNase, at least one carbohydrase and a cleaning component, wherein the carbohydrase is a cellulase, an amylase, a mannanase or a xylanase; and b) optionally rinsing the item, wherein the item is preferably a textile. The invention further relates to a method of deep cleaning of an item, comprising the steps of: a) contacting the item with a solution comprising an enzyme mixture comprising a DNase and a carbohydrase and optionally a protease; and a cleaning component, wherein the cleaning component is selected from 0.1 to 15 wt. %, e.g., from about 1% to about 40% of at least one a surfactant; 0.5 to 20 wt. %, e.g., from about 5% to about 50% of at least one builder; and 0.01 to 10 wt. %, e.g., from about 1% to about 20% of at least one bleach component; and b) optionally rinsing the item, wherein the item is preferably a textile.

DETAILED DESCRIPTION OF THE INVENTION

Various enzymes are applied in cleaning processes each targeting specific types of soiling such as protein, starch and grease soiling. Enzymes are now standard ingredients in detergents for laundry and dish wash. The effectiveness of these commercial enzymes provides detergents which removes much of the soiling. However, organic matters such as EPS (extracellular polymeric substance) comprised in much biofilm constitute a challenging type of staining due to the complex nature of such organic matters. None of the commercially available cleaning compositions effectively remove or reduce EPS and/or biofilm related stains. Biofilm may be produced when a group of microorganisms' cells stick to each other or stick to a surface, such as a textile, dishware or hard surface or another kind of surface. These adherent cells are frequently embedded within a self-produced matrix of extracellular polymeric substance (EPS), which constitute 50% to 90% of the biofilm's total organic matter. EPS is mostly composed of polysaccharides (exopolysaccharides) and proteins, but include other macro-molecules such as eDNA, lipids and other organic substances. Organic matter like biofilm may be sticky or glueing, which when present on textile, may give rise to redeposition or backstaining of soil resulting in a greying of the textile. Another drawback of organic matter, e.g., biofilm is the malodor as various malodor related molecules are often associated with organic matter, e.g., biofilm. Further, when dirty laundry items are washed together with less dirty laundry items the dirt present in the wash liquor tend to stick to organic matter, e.g., biofilm or biofilm components as a result, hereof the laundry item is more "soiled" after wash than before wash. This is effect may also be termed redeposition.

The compositions of the invention comprise a blend of DNase and a carbohydrase, wherein the carbohydrase is a cellulase, an amylase, a mannanase or a xylanase and effectively reduce or remove organic components, such as protein and DNA from surfaces such as textiles and hard surfaces, e.g., dishes.

The compositions of the invention comprise a blend of DNase and a carbohydrase, wherein the carbohydrase is a cellulase, an amylase, a mannanase or a xylanase and effectively reduce or limit redeposition when applied in, e.g., laundry process.

The compositions of the invention comprise a blend of DNase and a carbohydrase, wherein the carbohydrase is a cellulase, an amylase, a mannanase or a xylanase and effectively reduce or limit malodor of, e.g., textiles or hard surfaces such as dishes.

The compositions of the invention comprise a blend of DNase and a carbohydrase, wherein the carbohydrase is a cellulase, an amylase, a mannanase or a xylanase and improve whiteness of textile.

A composition of the invention is preferably a cleaning composition, the composition of the invention comprises at least one DNase and at least one a carbohydrase, wherein the carbohydrase is a cellulase, an amylase, a mannanase or a xylanase. Examples of useful DNases and carbohydrases are mentioned below in the sections "Polypeptides having DNase activity" and "Polypeptides having mannanase, cellulase, xylanase or amylase activity" respectively.

Polypeptides Having DNase Activity

The term "DNase" means a polypeptide with DNase (deoxyribonuclease) activity that catalyzes the hydrolytic cleavage of phosphodiester linkages in a DNA backbone, thus degrading DNA. Exodeoxyribonuclease cut or cleaves residues at the end of the DNA back bone where endodeoxyribonucleases cleaves or cut within the DNA backbone. A DNase may cleave only double-stranded DNA or may cleave double stranded and single stranded DNA. The term "DNases" and the expression "a polypeptide with DNase activity" are used interchangeably throughout the application. For purposes of the present invention, DNase activity is determined according to the procedure described in the Assay I.

Preferably the DNase is selected from any of the enzyme classes E.C.3.1, preferably E.C.3.1.21, e.g., such as E.C.3.1.21.X, where X=1, 2, 3, 4, 5, 6, 7, 8 or 9, or, e.g., Deoxyribonuclease I, Deoxyribonuclease IV, Type I site-specific deoxyribonuclease, Type II site-specific deoxyribonuclease, Type III site-specific deoxyribonuclease, CC-preferring endo-deoxyribonuclease, Deoxyribonuclease V, T(4) deoxyribonuclease II, T(4) deoxyribonuclease IV or E.C. 3.1.22.Y where Y=1, 2, 4 or 5, e.g., Deoxyribonuclease II, *Aspergillus* deoxyribonuclease K(1), Crossover junction endo-deoxyribonuclease, Deoxyribonuclease X.

Preferably, the polypeptide having DNase activity is obtained from a microorganism and the DNase is a microbial enzyme. The DNase is preferably of fungal or bacterial origin.

The DNase may be obtainable from *Bacillus* e.g., *Bacillus licheniformis, Bacillus subtilis, Bacillus* sp-62451, *Bacillus horikoshii, Bacillus* sp-62451, *Bacillus* sp-16840, *Bacillus* sp-62668, *Bacillus* sp-13395, *Bacillus horneckiae, Bacillus* sp-11238, *Bacillus cibi, Bacillus idriensis, Bacillus* sp-62520, *Bacillus* sp-16840, *Bacillus* sp-62668, *Bacillus algicola, Bacillus vietnamensis, Bacillus hwajinpoensis, Bacillus indicus, Bacillus marisflavi, Bacillus luciferensis, Bacillus* sp. SA2-6.

The DNase may also be obtained from any of the following *Pyrenochaetopsis* sp., *Vibrissea flavovirens, Setosphaeria rostrate, Endophragmiella valdina, Corynespora cassiicola, Paraphoma* sp. XZ1965, *Monilinia fructicola, Curvularia lunata, Penicillium reticulisporum, Penicillium quercetorum, Setophaeosphaeria* sp., *Alternaria, Alternaria* sp. XZ2545, *Trichoderma reesei, Chaetomium thermophilum, Scytalidium thermophilum, Metapochonia suchlasporia, Daldinia fissa, Acremonium* sp. XZ2007, *Acremonium* sp. XZ2414, *Acremonium dichromosporum, Sarocladium* sp. XZ2014, *Metarhizium* sp. HNA15-2, *Isaria tenuipes Scytalidium circinatum, Metarhizium lepidiotae, Thermobispora bispora, Sporormia fimetaria, Pycnidiophora* cf. *dispera*, Enviromental sample D, Enviromental sample O, Clavicipitaceae sp-70249, *Westerdykella* sp. AS85-2, *Humicolopsis cephalosporioides, Neosartorya massa, Roussoella intermedia, Pleosporales, Phaeosphaeria* or *Didymosphaeria futilis*.

The DNases to be used in a composition of the invention preferable belong to the NUC1 group of DNases. The NUC1 group of DNases comprises polypeptides which in addition to having DNase activity, may comprise one or more of the motifs [T/D/S][G/N]PQL (SEQ ID NO 69), [F/L/Y/I]A[N/R]D[L/I/P/V] (SEQ ID NO: 70), or C[D/N]T[A/R] (SEQ ID NO: 71). One embodiment of the invention relates to a composition comprising a carbohydrase, selected from cellulases, amylases, mannanases and xylanases, and polypeptides having DNase activity, wherein the polypeptides comprises one or more of the motifs [T/D/S][G/N]PQL (SEQ ID NO 69), [F/L/Y/I]A[N/R]D[L/I/P/V] (SEQ ID NO: 70) or C[D/N]T[A/R] (SEQ ID NO: 71).

The DNases preferably comprises a NUC1_A domain [D/Q][I/V]DH (SEQ ID NO 72). In addition to comprising any of the domain motifs [T/D/S][G/N]PQL, [F/L/Y/I]A[N/R]D[L/I/P/V] or C[D/N]T[A/R] the polypeptides having DNase activity, to be used in a composition of the invention, may comprise the NUC1_A domain and may share the common motif [D/Q][I/V]DH (SEQ ID NO 72). One embodiment the invention relates to compositions comprising a carbohydrase, selected from cellulases, amylases, mannanases and xylanases, and polypeptides, which comprises one or more motifs selected from the motifs [T/D/S][G/N]PQL, [F/L/Y/I]A[N/R]D[L/I/P/V], C[D/N]T[A/R] and [D/Q][I/V]DH, wherein the polypeptides have DNase activity.

The DNases to be added to a composition of the invention preferably belong to the group of DNases comprised in the GYS-clade, which are group of DNases on the same branch of a phylogenetic tree having both structural and functional similarities. These NUC1 and/or NUC1_A DNases comprise the conservative motifs [D/M/L][S/T]GYSR[D/N] (SEQ ID NO: 73) or ASXNRSKG (SEQ ID NO: 74) and share similar structural and functional properties. The DNases of the GYS-clade are preferably obtained from *Bacillus* genus.

One embodiment of the invention relates to a composition comprising a carbohydrase, selected from cellulases, amylases, mannanases and xylanases, a polypeptide of the GYS Glade having DNase activity, optionally wherein the polypeptide comprise one or both of the motifs [D/M/L][S/T]

GYSR[D/N] (SEQ ID NO: 73), ASXNRSKG (SEQ ID NO: 74) and wherein the polypeptide is selected from the group of polypeptides:

a) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 1, b) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 2, c) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 3, d) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 4, e) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 5, f) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 6, g) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 7, h) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 8, i) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 9, j) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 10, k) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 11, l) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 12, m) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 13, n) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 14, o) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 15, p) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 16, q) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 17, r) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 18, s) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 19, t) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 20, u) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 21, v) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 22, w) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 23, x) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 24, and y) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 25.

Polypeptides having DNase activity and which comprise the GYS-clade motifs have shown particularly good deep cleaning properties, e.g., the DNases are particularly effective in removing or reducing DNA stains, e.g., associated with biofilm or dead cell debris, from an item such as a textile or a hard surface. In addition, these DNases are particularly effective in removing or reducing malodor, from an item such as a textile or a hard surface. Further, the GYS-clade DNases are particularly effective in preventing redeposition when laundering an item such as textile.

In one embodiment the DNases to be added in a composition of the invention preferably belong to the group of DNases comprised in the NAWK-clade, which are NUC1 and NUC1_A DNases, which may further comprise the conservative motifs [V/I]PL[S/A]NAWK (SEQ ID NO: 75) or NPQL (SEQ ID NO: 76).

One embodiment of the invention relates to a composition comprising a carbohydrase selected from a cellulase, an amylase, a mannanase or a xylanase, and a polypeptide of the NAWK-clade having DNase activity, optionally wherein the polypeptide comprise one or both of the motifs [V/I]PL [S/A]NAWK (SEQ ID NO: 75) or NPQL (SEQ ID NO: 76) and wherein the polypeptide is selected from the group of polypeptides:

a) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 26, b) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 27, c) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 28, d) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 29, e) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 30, f) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 31, g) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 32, h) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 33, i) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 34, j) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 35, k) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 36, l) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 37, and m) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 38.

Polypeptides having DNase activity and which comprise the NAWK-clade motifs have shown particularly good deep cleaning properties, e.g., the DNases are particularly effective in removing or reducing DNA stains, e.g., associated with biofilm or dead cell debris, from an item such as a textile or a hard surface. In addition, these DNases are particularly effective in removing or reducing malodor, from an item such as a textile or a hard surface. Further, the NAWK-clade DNases are particularly effective in preventing redeposition when laundering an item such as textile.

The DNases to be added in a composition of the invention preferably belong to the group of DNases comprised in the KNAW-clade, which are NUC1 and NUC1_A DNases which may further comprise the conservative motifs P[Q/E]L[W/Y] (SEQ ID NO: 77) or [K/H/E]NAW (SEQ ID NO: 78).

One embodiment of the invention relates to a composition comprising a carbohydrase, selected from a cellulase, an amylase, a mannanase or a xylanase, and a polypeptide of the KNAW Glade having DNase activity, optionally wherein the polypeptide comprise one or both of the motifs P[Q/E]L[W/Y] (SEQ ID NO: 77) or [K/H/E]NAW (SEQ ID NO: 78), and wherein the polypeptide is selected from the group of polypeptides:

a) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 39, b) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 40, c) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 41, d) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 42, e) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 43 f) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 44, g) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 45, h) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 46, i) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 47, j) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 48, k) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 49, l) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 50, and m) a polypeptide having at least 60%, at least 65%, at least 70%, at least 75% at least 80%, at least 85%, at least 90%, at least 95%, at least 98% or at least 100% sequence identity to the polypeptide shown in SEQ ID NO: 51.

Polypeptides having DNase activity and which comprise the KNAW-clade motifs have shown particularly good deep cleaning properties, e.g., the DNases are particularly effective in removing or reducing DNA stains, e.g., associated with biofilm or dead cell debris, from an item such as a textile or a hard surface. In addition, these DNases are particularly effective in removing or reducing malodor, from an item such as a textile or a hard surface. Further, the KNAW-clade DNases are particularly effective in preventing redeposition when laundering an item such as textile.

In some embodiments, the present invention relates to compositions comprising a carbohydrase, selected from cellulases, amylases, mannanases and xylanases, and a polypeptide obtainable from *Bacillus*, e.g., obtainable from *Bacillus* sp-62451 and having a sequence identity to the polypeptide shown in SEQ ID NO: 1 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 1.

In some embodiments, the present invention relates to compositions comprising a carbohydrase, selected from cellulases, amylases, mannanases and xylanases, and a polypeptide obtainable from *Bacillus*, e.g., obtainable from *Bacillus horikoshii* and having a sequence identity to the polypeptide shown in SEQ ID NO: 2 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 2.

In some embodiments, the present invention relates to compositions comprising a carbohydrase, selected from cellulases, amylases, mannanases and xylanases, and a polypeptide obtainable from *Bacillus*, e.g., obtainable from *Bacillus* sp-62520 and having a sequence identity to the polypeptide shown in SEQ ID NO: 3 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 3.

In some embodiments, the present invention relates to compositions comprising a carbohydrase, selected from cellulases, amylases, mannanases and xylanases, and a polypeptide obtainable from *Bacillus*, e.g., obtainable from *Bacillus* sp-62520 and having a sequence identity to the polypeptide shown in SEQ ID NO: 4 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 4.

In some embodiments, the present invention relates to compositions comprising a carbohydrase, selected from cellulases, amylases, mannanases and xylanases, and a polypeptide obtainable from *Bacillus*, e.g., obtainable from *Bacillus horikoshii* and having a sequence identity to the polypeptide shown in SEQ ID NO: 5 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 5.

In some embodiments, the present invention relates to compositions comprising a carbohydrase, selected from cellulases, amylases, mannanases and xylanases, and a polypeptide obtainable from *Bacillus*, e.g., obtainable from *Bacillus horikoshii* and having a sequence identity to the polypeptide shown in SEQ ID NO: 6 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 6.

In some embodiments, the present invention relates to compositions comprising a carbohydrase, selected from cellulases, amylases, mannanases and xylanases, and a polypeptide obtainable from *Bacillus*, e.g., obtainable from *Bacillus* sp-16840 and having a sequence identity to the polypeptide shown in SEQ ID NO: 7 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 7.

In some embodiments, the present invention relates to compositions comprising a carbohydrase, selected from cellulases, amylases, mannanases and xylanases, and a polypeptide obtainable from *Bacillus*, e.g., obtainable from *Bacillus* sp-16840 and having a sequence identity to the polypeptide shown in SEQ ID NO: 8 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 8.

In some embodiments, the present invention relates to compositions comprising a carbohydrase, selected from cellulases, amylases, mannanases and xylanases, and a polypeptide obtainable from *Bacillus*, e.g., obtainable from *Bacillus* sp-62668 and having a sequence identity to the polypeptide shown in SEQ ID NO: 9 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 9.

In some embodiments, the present invention relates to compositions comprising a carbohydrase, selected from cellulases, amylases, mannanases and xylanases, and a polypeptide obtainable from *Bacillus*, e.g., obtainable from *Bacillus* sp-13395 and having a sequence identity to the polypeptide shown in SEQ ID NO: 10 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 10.

In some embodiments, the present invention relates to compositions comprising a carbohydrase, selected from cellulases, amylases, mannanases and xylanases, and a polypeptide obtainable from *Bacillus*, e.g., obtainable from *Bacillus horneckiae* and having a sequence identity to the polypeptide shown in SEQ ID NO: 11 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 11.

In some embodiments, the present invention relates to compositions comprising a carbohydrase, selected from cellulases, amylases, mannanases and xylanases, and a polypeptide obtainable from *Bacillus*, e.g., obtainable from *Bacillus* sp-11238 and having a sequence identity to the polypeptide shown in SEQ ID NO: 12 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 12.

In some embodiments, the present invention relates to compositions comprising a carbohydrase, selected from cellulases, amylases, mannanases and xylanases, and a polypeptide obtainable from *Bacillus*, e.g., obtainable from *Bacillus cibi* and having a sequence identity to the polypeptide shown in SEQ ID NO: 13 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 13.

In some embodiments, the present invention relates to compositions comprising a carbohydrase, selected from cellulases, amylases, mannanases and xylanases, and a polypeptide obtainable from *Bacillus*, e.g., obtainable from *Bacillus* sp-18318 and having a sequence identity to the polypeptide shown in SEQ ID NO: 14 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 14.

In some embodiments, the present invention relates to compositions comprising a carbohydrase, selected from cellulases, amylases, mannanases and xylanases, and a polypeptide obtainable from *Bacillus*, e.g., obtainable from *Bacillus idriensis* and having a sequence identity to the polypeptide shown in SEQ ID NO: 15 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 15.

In some embodiments, the present invention relates to compositions comprising a carbohydrase, selected from cellulases, amylases, mannanases and xylanases, and a polypeptide obtainable from *Bacillus*, e.g., obtainable from *Bacillus algicola* having a sequence identity to the polypeptide shown in SEQ ID NO: 16 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 16.

In some embodiments, the present invention relates to compositions comprising a carbohydrase, selected from cellulases, amylases, mannanases and xylanases, and a polypeptide obtainable from Enviromental sample J and having a sequence identity to the polypeptide shown in SEQ ID NO: 17 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 17.

In some embodiments, the present invention relates to compositions comprising a carbohydrase, selected from cellulases, amylases, mannanases and xylanases, and a polypeptide obtainable from *Bacillus*, e.g., obtainable from *Bacillus vietnamensis* and having a sequence identity to the polypeptide shown in SEQ ID NO: 18 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 18.

In some embodiments, the present invention relates to compositions comprising a carbohydrase, selected from cellulases, amylases, mannanases and xylanases, and a polypeptide obtainable from *Bacillus*, e.g., obtainable from *Bacillus hwajinpoensis* and having a sequence identity to the polypeptide shown in SEQ ID NO: 19 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 19.

In some embodiments, the present invention relates to compositions comprising a carbohydrase, selected from cellulases, amylases, mannanases and xylanases, and a polypeptide obtainable from *Paenibacillus mucilaginosus* and having a sequence identity to the polypeptide shown in SEQ ID NO: 20 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 20.

In some embodiments, the present invention relates to compositions comprising a carbohydrase, selected from cellulases, amylases, mannanases and xylanases, and a polypeptide obtainable from *Bacillus*, e.g., obtainable from *Bacillus indicus* and having a sequence identity to the polypeptide shown in SEQ ID NO: 21 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 21.

In some embodiments, the present invention relates to compositions comprising a carbohydrase, selected from cellulases, amylases, mannanases and xylanases, and a polypeptide obtainable from *Bacillus*, e.g., obtainable from *Bacillus marisflavi* and having a sequence identity to the polypeptide shown in SEQ ID NO: 22 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 22.

In some embodiments, the present invention relates to compositions comprising a carbohydrase, selected from cellulases, amylases, mannanases and xylanases, and a polypeptide obtainable from *Bacillus*, e.g., obtainable from *Bacillus luciferensis* and having a sequence identity to the polypeptide shown in SEQ ID NO: 23 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 23.

In some embodiments, the present invention relates to compositions comprising a carbohydrase, selected from cellulases, amylases, mannanases and xylanases, and a polypeptide obtainable from *Bacillus*, e.g., obtainable from *Bacillus marisflavi* and having a sequence identity to the polypeptide shown in SEQ ID NO: 24 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 24.

In some embodiments, the present invention relates to compositions comprising a carbohydrase, selected from cellulases, amylases, mannanases and xylanases, and a polypeptide obtainable from *Bacillus*, e.g., obtainable from *Bacillus* sp. SA2-6 and having a sequence identity to the polypeptide shown in SEQ ID NO: 25 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 25.

In some embodiments, the present invention relates to compositions comprising a carbohydrase, selected from cellulases, amylases, mannanases and xylanases, and a polypeptide obtainable from *Pyrenochaetopsis* sp. and having a sequence identity to the polypeptide shown in SEQ ID NO: 26 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 26.

In some embodiments, the present invention relates to compositions comprising a carbohydrase, selected from cellulases, amylases, mannanases and xylanases, and a polypeptide obtainable from *Vibrissea flavovirens* and having a sequence identity to the polypeptide shown in SEQ ID NO: 27 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 27.

In some embodiments, the present invention relates to compositions comprising a carbohydrase, selected from cellulases, amylases, mannanases and xylanases, and a polypeptide obtainable from *Setosphaeria rostrate* and having a sequence identity to the polypeptide shown in SEQ ID NO: 28 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 28.

In some embodiments, the present invention relates to compositions comprising a carbohydrase, selected from cellulases, amylases, mannanases and xylanases, and a polypeptide obtainable from *Endophragmiella valdina* and having a sequence identity to the polypeptide shown in SEQ ID NO: 29 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 29.

In some embodiments, the present invention relates to compositions comprising a carbohydrase, selected from cellulases, amylases, mannanases and xylanases, and a polypeptide obtainable from *Corynespora cassiicola* and having a sequence identity to the polypeptide shown in SEQ ID NO: 30 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 30.

In some embodiments, the present invention relates to compositions comprising a carbohydrase, selected from cellulases, amylases, mannanases and xylanases, and a polypeptide obtainable from *Paraphoma* sp. XZ1965 and having a sequence identity to the polypeptide shown in SEQ ID NO: 31 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 31.

In some embodiments, the present invention relates to compositions comprising a carbohydrase, selected from cellulases, amylases, mannanases and xylanases, and a polypeptide obtainable from *Monilinia fructicola* and having a sequence identity to the polypeptide shown in SEQ ID NO: 32 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 32.

In some embodiments, the present invention relates to compositions comprising a carbohydrase, selected from cellulases, amylases, mannanases and xylanases, and a polypeptide obtainable from *Curvularia lunata* and having a sequence identity to the polypeptide shown in SEQ ID NO: 33 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 33.

In some embodiments, the present invention relates to compositions comprising a carbohydrase, selected from cellulases, amylases, mannanases and xylanases, and a polypeptide obtainable from *Penicillium reticulisporum* and having a sequence identity to the polypeptide shown in SEQ ID NO: 34 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 34.

In some embodiments, the present invention relates to compositions comprising a carbohydrase, selected from cellulases, amylases, mannanases and xylanases, and a polypeptide obtainable from *Penicillium quercetorum* and having a sequence identity to the polypeptide shown in SEQ ID NO: 35 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 35.

In some embodiments, the present invention relates to compositions comprising a carbohydrase, selected from cellulases, amylases, mannanases and xylanases, and a polypeptide obtainable from *Setophaeosphaeria* sp. and having a sequence identity to the polypeptide shown in SEQ ID NO: 36 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 36.

In some embodiments, the present invention relates to compositions comprising a carbohydrase, selected from cellulases, amylases, mannanases and xylanases, and a polypeptide obtainable from *Alternaria* sp. XZ2545 and having a sequence identity to the polypeptide shown in SEQ ID NO: 37 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 37.

In some embodiments, the present invention relates to compositions comprising a carbohydrase, selected from cellulases, amylases, mannanases and xylanases, and a polypeptide obtainable from *Alternaria* and having a sequence identity to the polypeptide shown in SEQ ID NO: 38 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 38.

In some embodiments, the present invention relates to compositions comprising a carbohydrase, selected from cellulases, amylases, mannanases and xylanases, and a polypeptide obtainable from *Trichoderma reesei* and having a sequence identity to the polypeptide shown in SEQ ID NO: 39 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 39.

In some embodiments, the present invention relates to compositions comprising a carbohydrase, selected from cellulases, amylases, mannanases and xylanases, and a polypeptide obtainable from *Chaetomium thermophilum* and having a sequence identity to the polypeptide shown in SEQ ID NO: 40 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 40.

In some embodiments, the present invention relates to compositions comprising a carbohydrase, selected from cellulases, amylases, mannanases and xylanases, and a polypeptide obtainable from *Scytalidium thermophilum* and having a sequence identity to the polypeptide shown in SEQ ID NO: 41 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 41.

In some embodiments, the present invention relates to compositions comprising a carbohydrase, selected from cellulases, amylases, mannanases and xylanases, and a polypeptide obtainable from *Metapochonia suchlasporia* and having a sequence identity to the polypeptide shown in SEQ ID NO: 42 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 42.

In some embodiments, the present invention relates to compositions comprising a carbohydrase, selected from cellulases, amylases, mannanases and xylanases, and a polypeptide obtainable from *Daldinia fissa* and having a sequence identity to the polypeptide shown in SEQ ID NO: 43 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 43.

In some embodiments, the present invention relates to compositions comprising a carbohydrase, selected from cellulases, amylases, mannanases and xylanases, and a polypeptide obtainable from *Acremonium* sp. XZ2007 and having a sequence identity to the polypeptide shown in SEQ ID NO: 44 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 44.

In some embodiments, the present invention relates to compositions comprising a carbohydrase, selected from cellulases, amylases, mannanases and xylanases, and a polypeptide obtainable from *Acremonium dichromosporum* and having a sequence identity to the polypeptide shown in SEQ ID NO: 45 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 45.

In some embodiments, the present invention relates to compositions comprising a carbohydrase, selected from cellulases, amylases, mannanases and xylanases, and a polypeptide obtainable from *Sarocladium* sp. XZ2014 and having a sequence identity to the polypeptide shown in SEQ ID NO: 46 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 46.

In some embodiments, the present invention relates to compositions comprising a carbohydrase, selected from cellulases, amylases, mannanases and xylanases, and a polypeptide obtainable from *Metarhizium* sp. HNA15-2 and having a sequence identity to the polypeptide shown in SEQ ID NO: 47 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 47.

In some embodiments, the present invention relates to compositions comprising a carbohydrase, selected from cellulases, amylases, mannanases and xylanases, and a polypeptide obtainable from *Acremonium* sp. XZ2414 and having a sequence identity to the polypeptide shown in SEQ ID NO: 48 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 48.

In some embodiments, the present invention relates to compositions comprising a carbohydrase, selected from cellulases, amylases, mannanases and xylanases, and a polypeptide obtainable from *Isaria tenuipes* and having a sequence identity to the polypeptide shown in SEQ ID NO: 49 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 49.

In some embodiments, the present invention relates to compositions comprising a carbohydrase, selected from cellulases, amylases, mannanases and xylanases, and a polypeptide obtainable from *Scytalidium circinatum* and having a sequence identity to the polypeptide shown in SEQ ID NO: 50 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 50.

In some embodiments, the present invention relates to compositions comprising a carbohydrase, selected from cellulases, amylases, mannanases and xylanases, and a polypeptide obtainable from *Metarhizium lepidiotae* and having a sequence identity to the polypeptide shown in SEQ ID NO: 51 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 51.

In some embodiments, the present invention relates to compositions comprising a carbohydrase, selected from cellulases, amylases, mannanases and xylanases, and a polypeptide obtainable from *Thermobispora bispora* and having a sequence identity to the polypeptide shown in SEQ ID NO: 52 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 52.

In some embodiments, the present invention relates to compositions comprising a carbohydrase, selected from cellulases, amylases, mannanases and xylanases, and a polypeptide obtainable from *Sporormia fimetaria* and having a sequence identity to the polypeptide shown in SEQ ID NO: 53 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 53.

In some embodiments, the present invention relates to compositions comprising a carbohydrase, selected from cellulases, amylases, mannanases and xylanases, and a polypeptide obtainable from *Pycnidiophora* cf. dispera and having a sequence identity to the polypeptide shown in SEQ ID NO: 54 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 54.

In some embodiments, the present invention relates to compositions comprising a carbohydrase, selected from cellulases, amylases, mannanases and xylanases, and a polypeptide obtainable from Enviromental sample D and having a sequence identity to the polypeptide shown in SEQ ID NO: 55 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 55.

In some embodiments, the present invention relates to compositions comprising a carbohydrase, selected from cellulases, amylases, mannanases and xylanases, and a polypeptide obtainable from Enviromental sample O and having a sequence identity to the polypeptide shown in SEQ ID NO: 56 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 56.

In some embodiments, the present invention relates to compositions comprising a carbohydrase, selected from cellulases, amylases, mannanases and xylanases, and a polypeptide obtainable from Clavicipitaceae sp-70249 and having a sequence identity to the polypeptide shown in SEQ ID NO: 57 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 57.

In some embodiments, the present invention relates to compositions comprising a carbohydrase, selected from cellulases, amylases, mannanases and xylanases, and a polypeptide obtainable from *Westerdykella* sp. AS85-2 and having a sequence identity to the polypeptide shown in SEQ ID NO: 58 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 58.

In some embodiments, the present invention relates to compositions comprising a carbohydrase, selected from cellulases, amylases, mannanases and xylanases, and a polypeptide obtainable from *Humicolopsis cephalosporioides* and having a sequence identity to the polypeptide shown in SEQ ID NO: 59 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 59.

In some embodiments, the present invention relates to compositions comprising a carbohydrase, selected from cellulases, amylases, mannanases and xylanases, and a polypeptide obtainable from *Neosartorya massa* and having a sequence identity to the polypeptide shown in SEQ ID NO: 60 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 60.

In some embodiments, the present invention relates to compositions comprising a carbohydrase, selected from cellulases, amylases, mannanases and xylanases, and a polypeptide obtainable from *Roussoella intermedia* and having a sequence identity to the polypeptide shown in SEQ ID NO: 61 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 61.

In some embodiments, the present invention relates to compositions comprising a carbohydrase, selected from cellulases, amylases, mannanases and xylanases, and a polypeptide obtainable from Pleosporales and having a sequence identity to the polypeptide shown in SEQ ID NO: 62 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 62.

In some embodiments, the present invention relates to compositions comprising a carbohydrase, selected from cellulases, amylases, mannanases and xylanases, and a polypeptide obtainable from *Phaeosphaeria* and having a sequence identity to the polypeptide shown in SEQ ID NO: 63 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 63.

In some embodiments, the present invention relates to compositions comprising a carbohydrase, selected from cellulases, amylases, mannanases and xylanases, and a polypeptide obtainable from *Didymosphaeria futilis* and having a sequence identity to the polypeptide shown in SEQ ID NO: 64 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 64.

In some embodiments, the present invention relates to compositions comprising a carbohydrase, selected from cellulases, amylases, mannanases and xylanases, and a polypeptide obtainable from *Bacillus*, e.g., obtainable from *Bacillus licheniformis* having a sequence identity to the polypeptide shown in SEQ ID NO: 65 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 65.

In some embodiments, the present invention relates to compositions comprising a carbohydrase, selected from cellulases, amylases, mannanases and xylanases, and a polypeptide obtainable from *Bacillus*, e.g., obtainable from

*Bacillus subtilis* having a sequence identity to the polypeptide shown in SEQ ID NO: 66 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 66.

In some embodiments, the present invention relates to compositions comprising a carbohydrase, selected from cellulases, amylases, mannanases and xylanases, and a polypeptide obtainable from *Aspergillus*, e.g., obtainable from *Aspergillus oryzae* having a sequence identity to the polypeptide shown in SEQ ID NO: 67 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 67.

In some embodiments, the present invention relates to compositions comprising a carbohydrase, selected from cellulases, amylases, mannanases and xylanases, and a polypeptide obtainable from *Trichoderma*, e.g., obtainable from *Trichoderma harzianum* having a sequence identity to the polypeptide shown in SEQ ID NO: 68 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 68.

The DNases above may be combined with any of the carbohydrases below to form a blend to be added to a composition according to the invention.

Polypeptides Having Carbohydrase Activity (Carbohydrases)

Carbohydrase is a protein/enzyme that catalyse carbohydrates to break down carbohydrates to, e.g., simple sugar such as monosaccharides. Thus, carbohydrases are any of a group of enzymes that promote hydrolysis of a carbohydrate. Starch hydrolyzing carbohydrases (e.g., amylases) work on, e.g., amylose and amylopectin and non-starch carbohydrases includes enzymes which hydrolyze polymers made up of carbon sugars, e.g., cellulases which will ultimately produce glucose when complete hydrolysis is achieved. Another example is lactase which hydrolyses lactose to glucose and galactose. Examples of carbohydrases includes amylases, cellulases and mannanases. The carbohydrases to be incorporated in a composition according to the invention is preferably selected from xylanases, cellulases, mannanases and amylases.

Polypeptides Having Mannanase Activity

The term "mannanase" is defined here as an enzyme that hydrolyses compounds known as mannanes. The term "mannanase activity" is as an enzyme catalyzed hydrolysis of mannan, for purposes of the present invention, mannanase activity is determined according to the procedure described in the Assay II. Suitable mannanases include those of bacterial or fungal origin. Chemically or genetically modified mannanases are included. The mannanase may be an alkaline mannanase of Family 5 or 26. It may be a wild-type from *Bacillus* or *Humicola*, particularly *B. agaradhaerens, B. licheniformis, B. halodurans, B. clausii*, or *H. insolens*. Suitable mannanases are described in WO 1999/064619. Commercially available mannanases are Mannaway (Novozymes A/S), and EFFECTENZ™ M1000 from Dupont. In one aspect, the present invention relates to a cleaning composition comprising at least one enzyme having mannanase activity, which may be obtained from a bacterial strain of the genus *Bacillus*. Preferably, a polypeptide selected from the group of polypeptides comprising the amino acid sequence shown in SEQ ID NO: 82. In one aspect the present invention relates to a cleaning composition comprising at least one enzyme classified in the EC 3.2.1.78 and which has mannanase activity.

Useful mannanases include polypeptides that are substantially homologous to the polypeptides shown in SEQ ID NO: 82 and species homologs (paralogs or orthologs) thereof.

The term "substantially homologous" is used herein to denote polypeptides having at least 60%, at least 65%, preferably at least 70%, more preferably at least 75%, more preferably at least 80%, more preferably at least 85%, more preferably at least 90% more preferably at least 95%, more preferably at least 97%, even more preferably at least 98% sequence identity to the sequence.

In some embodiments, the present invention relates compositions comprising a DNase and a polypeptide having a sequence identity to the polypeptide shown in SEQ ID NO: 82 of at least 60%, e.g., at least 65%, at least 70%, at least 75%, at least 80%, at least 85%, at least 90%, at least 95%, at least 96%, at least 97%, at least 98%, at least 99%, or 100% and which have mannanase activity. In one aspect, the polypeptides differ by up to 10 amino acids, e.g., 1, 2, 3, 4, 5, 6, 7, 8, 9, or 10, from the mature polypeptide shown in SEQ ID NO: 82.

The mannanase suitable for a composition of the invention may, in addition to the enzyme core comprising a catalytically domain, also comprise a cellulose binding domain (CBD), the cellulose binding domain and enzyme core (the catalytically active domain) of the enzyme being operably linked.

In one aspect, the present invention relates to a composition comprising a mannanase and a DNase, wherein the a mannanase is: i) polypeptide comprising an amino acid sequence as shown in SEQ ID NO:82; or ii) or a polypeptide having a sequence identity of at least 65%, at least 70%, at least 75%, at least 80%, at least 85%, at least 90%, at least 95%, at least 96%, at least 97%, at least 98%, or at least 99% to the amino acid sequence shown in SEQ ID NO 82.

In one aspect, the present invention relates to a composition comprising a mannanase and a DNase, wherein the mannanase is selected from a polypeptide having at least 65%, at least 70%, at least 75%, at least 80%, at least 85%, at least 90%, at least 95%, at least 96%, at least 97%, at least 98%, or at least 99% or 100% sequence identity to the polypeptide shown in SEQ ID NO: 82.

Polypeptides Having Cellulase Activity

The term "cellulase" is defined in the present context as an enzyme that hydrolyses cellulose. In a preferred embodiment of the invention, the cellulase is an endoglucanase. The term "cellulase activity" is defined herein as an enzyme catalyzed hydrolysis of 1,4-beta-D-glucosidic linkages in beta-1,4-glucan (cellulose). For purposes of the present invention, cellulase activity is determined using AZCL-HE-cellulose (from Megazyme) as the reaction substrate, as shown in Assay IV. Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophth-* thora thermophila and Fusarium oxysporum disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 0495257, EP 0531372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO 99/01544.

Other cellulases are endo-beta-1,4-glucanase enzyme having a sequence of at least 97% identity to the amino acid sequence of position 1 to position 773 of SEQ ID NO:2 of WO 02/99091 or a family 44 xyloglucanase, which a xyloglucanase enzyme having a sequence of at least 60% identity to positions 40-559 of SEQ ID NO: 2 of WO 01/62903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft™ (Novozymes A/S), Whitezyme™ (Novozymes A/S), Clazinase™, and Puradax HA™ (Genencor International Inc.), and KAC-500(B)™ (Kao Corporation), Revitalenz™ 1000, Revitalenz™ 2000, Revitalenz™ 3000 (Dupont).

In one aspect of the present invention, the cleaning composition comprise a DNase and a polypeptide having cellulase activity, which comprise the amino acid sequence of SEQ ID NO: 83. In one aspect of the present invention, the cleaning composition comprise a DNase and a polypeptide having cellulase activity, which comprises an amino acid sequence having at least 60%, at least 65%, at least 70%, more preferably at least 75%, more preferably at least 80%, more preferably at least 85%, more preferably at least 90%, more preferably at least 95%, more preferably at least 96%, even more preferably at least 97%, most preferably at least 98%, or even most preferably at least 99% or 100% sequence identity to SEQ ID NO: 83.

In one aspect of the present invention, the cleaning composition comprise a DNase and a polypeptide having cellulase activity, which comprise the amino acid sequence of SEQ ID NO: 84. In one aspect of the present invention, the cleaning composition comprise a DNase and a polypeptide having cellulase activity, which comprises an amino acid sequence having at least 60%, at least 65%, at least 70%, more preferably at least 75%, more preferably at least 80%, more preferably at least 85%, more preferably at least 90%, more preferably at least 95%, more preferably at least 96%, even more preferably at least 97%, most preferably at least 98%, or even most preferably at least 99% or 100% sequence identity to SEQ ID NO: 84.

In one aspect of the present invention, the cleaning composition comprise a DNase and a polypeptide having cellulase activity, which comprise the amino acid sequence of SEQ ID NO: 85. In one aspect of the present invention, the cleaning composition comprise a DNase and a polypeptide having cellulase activity, which comprises an amino acid sequence having at least 60%, at least 65%, at least 70%, more preferably at least 75%, more preferably at least 80%, more preferably at least 85%, more preferably at least 90%, more preferably at least 95%, more preferably at least 96%, even more preferably at least 97%, most preferably at least 98%, or even most preferably at least 99% or 100% sequence identity to SEQ ID NO: 85.

In one aspect of the present invention, the cleaning composition comprise a DNase and a polypeptide having cellulase activity, which comprise the amino acid sequence of SEQ ID NO: 86. In one aspect of the present invention, the cleaning composition comprise a DNase and a polypeptide having cellulase activity, which comprises an amino acid sequence having at least 60%, at least 65%, at least 70%, more preferably at least 75%, more preferably at least 80%, more preferably at least 85%, more preferably at least 90%, more preferably at least 95%, more preferably at least 96%, even more preferably at least 97%, most preferably at least 98%, or even most preferably at least 99% or 100% sequence identity to SEQ ID NO: 86.

In the present invention, the cleaning composition can also comprise a cellulase, which is a xyloglucanase. The term "xyloglucanase activity" is defined herein as an enzyme catalyzed hydrolysis of xyloglucan, which is shown in Assay III. Xyloglucanase can comprise parent xyloglucanase and the variants thereof.

In one embodiment of the present invention, the xyloglucanase is a polypeptide comprising an amino acid sequence of SEQ ID NO 87. In one aspect of the present invention, the cleaning composition comprise a DNase and a polypeptide having xyloglucanase activity, which comprises an amino acid sequence having at least 60%, at least 65%, at least 70%, more preferably at least 75%, more preferably at least 80%, more preferably at least 85%, more preferably at least 90%, more preferably at least 95%, more preferably at least 96%, even more preferably at least 97%, most preferably at least 98%, or even most preferably at least 99% or 100% sequence identity to SEQ ID NO: 87.

Polypeptides Having Amylase Activity

An amylase is an enzyme that hydrolyses starch into sugars, for purposes of the present invention, amylase activity is determined according to the procedure described in the Assay V. Suitable amylases include alpha-amylases and/or a glucoamylases and may be of bacterial or fungal origin. Chemically modified or protein engineered mutants are included. Amylases include, for example, alpha-amylases obtained from Bacillus, e.g., a special strain of Bacillus licheniformis, described in more detail in GB 1,296,839.

In one aspect of the present invention, the cleaning composition comprise a DNase and a polypeptide having amylase activity, which comprise the amino acid sequence of SEQ ID NO: 88. In one aspect of the present invention, the cleaning composition comprise a DNase and a polypeptide having amylase activity, which comprises an amino acid sequence having at least 60%, at least 65%, at least 70%, more preferably at least 75%, more preferably at least 80%, more preferably at least 85%, more preferably at least 90%, more preferably at least 95%, more preferably at least 96%, even more preferably at least 97%, most preferably at least 98%, even most preferably at least 99% or 100% sequence identity to SEQ ID NO: 88.

In one aspect of the present invention, the cleaning composition comprise a DNase and a polypeptide having amylase activity, which comprise the amino acid sequence of SEQ ID NO: 89. In one aspect of the present invention, the cleaning composition comprise a DNase and a polypeptide having amylase activity, which comprises an amino acid sequence having at least 60%, at least 65%, at least 70%, more preferably at least 75%, more preferably at least 80%, more preferably at least 85%, more preferably at least 90%, more preferably at least 95%, more preferably at least 96%, even more preferably at least 97%, most preferably at least 98%, even most preferably at least 99% or 100% sequence identity to SEQ ID NO: 89.

In one aspect of the present invention, the cleaning composition comprise a DNase and a polypeptide having amylase activity, which comprise the amino acid sequence of SEQ ID NO: 90. In one aspect of the present invention, the cleaning composition comprise a DNase and a polypeptide having amylase activity, which comprises an amino acid sequence at least 60%, at least 65%, at least 70%, more preferably at least 75%, more preferably at least 80%, more preferably at least 85%, more preferably at least 90%, more preferably at least 95%, more preferably at least 96%, even more preferably at least 97%, most preferably at least 98%, or even most preferably at least 99%, identity SEQ ID NO: 90.

In one aspect of the present invention, the cleaning composition comprise a DNase and a polypeptide having amylase activity, which comprise the amino acid sequence of SEQ ID NO: 91. In one aspect of the present invention, the cleaning composition comprise a DNase and a polypeptide having amylase activity, which comprises an amino acid sequence at least 60%, at least 65%, at least 70%, more preferably at least 75%, more preferably at least 80%, more preferably at least 85%, more preferably at least 90%, more preferably at least 95%, more preferably at least 96%, even more preferably at least 97%, most preferably at least 98%, or even most preferably at least 99%, identity SEQ ID NO: 91.

Additional amylases include amylases comprising the polypeptide shown in SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444. Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193. Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: 48, 49, 107, 156, 181, 190, 197, 201, 209 and 264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;
H156Y+A181T+N190F+A209V+Q264S; or
G48A+T49I+G107A+H156Y+A181T+N190F+I201F+A209V+Q264S.

Further amylases which are suitable are amylases having SEQ ID NO: 6 in WO 99/19467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184. Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/23873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 2008/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264. Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128O+K178L+T182G+Y305R+G475K;
N128O+K178L+T182G+F202Y+Y305R+D319T+G475K;
S125A+N128C+K178L+T182G+Y305R+G475K; or
S125A+N128C+T131I+T165I+K178L+T182G+Y305R+G475K wherein the variants are C-terminally truncated and optionally further comprises a substitution at position 243 and/or a deletion at position 180 and/or position 181.

Further suitable amylases are amylases having SEQ ID NO: 1 of WO 2013/184577 or variants having 90% sequence identity to SEQ ID NO: 1 thereof. Preferred variants of SEQ ID NO: 1 are those having a substitution, a deletion or an insertion in one of more of the following positions: K176, R178, G179, T180, G181, E187, N192, M199, I203, S241, R458, T459, D460, G476 and G477. More preferred variants of SEQ ID NO: 1 are those having the substitution in one of more of the following positions: K176L, E187P, N192FYH, M199L, I203YF, S241QADN, R458N, T459S, D460T, G476K and G477K and/or deletion in position R178 and/or S179 or of T180 and/or G181. Most preferred amylase variants of SEQ ID NO: 1 are those having the substitutions:

E187P+I203Y+G476K
E187P+I203Y+R458N+T459S+D460T+G476K,
wherein the variants optionally further comprise a substitution at position 241 and/or a deletion at position 178 and/or position 179.

Further suitable amylases are amylases having SEQ ID NO: 1 of WO 2010/104675 or variants having 90% sequence identity to SEQ ID NO: 1 thereof. Preferred variants of SEQ ID NO: 1 are those having a substitution, a deletion or an insertion in one of more of the following positions: N21, D97, V128 K177, R179, S180, I181, G182, M200, L204, E242, G477 and G478. More preferred variants of SEQ ID NO: 1 are those having the substitution in one of more of the following positions: N21D, D97N, V128I K177L, M200L, L204YF, E242QA, G477K and G478K and/or deletion in position R179 and/or S180 or of I181 and/or G182. Most preferred amylase variants of SEQ ID NO: 1 are those having the substitutions:

N21D+D97N+V128I wherein the variants optionally further comprise a substitution at position 200 and/or a deletion at position 180 and/or position 181. Other suitable amylases are the alpha-amylase comprising the polypeptide sequence shown in SEQ ID NO: 12 in WO 01/66712 or a variant having at least 90% sequence identity to SEQ ID NO: 12. Preferred amylase variants are those having a substitution, a deletion or an insertion in one of more of the following positions of SEQ ID NO: 12 in WO 01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions. Other examples are amylase variants such as those described in WO 2011/098531, WO 2013/001078 and WO 2013/001087.

Commercially available amylases are Duramyl™, Termamyl™, Fungamyl™, Stainzyme™ Stainzyme Plus™, Natalase™, Liquozyme X and BAN™ (from Novozymes A/S), and Rapidase™, Purastar™/Effectenz™, Powerase, Preferenz S1000, Preferenz S100 and Preferenz S110 (from Genencor International Inc./DuPont).

A composition comprising:

The invention relates to compositions, preferably cleaning compositions comprising a DNase and a carbohydrase in combination with one or more additional cleaning composition components.

One embodiment of the invention relates to a cleaning composition comprising a DNase, at least one carbohydrase and a cleaning component, wherein the carbohydrase is a cellulase, an amylase, a mannanase or a xylanase. The carbohydrase may be any of the cellulases, amylases, mannanases or xylanases mentioned under the heading "Polypeptides having cellulase, amylase, mannanase or xylanase activity" respectively.

As shown in the examples of the present invention carbohydrases such as cellulases act synergistically with the DNase in reduction, and removal of biofilm or components hereof. Biofilm is a complex structure comprising, the target substrate, e.g., the DNA may be embedded in the biofilm structure and It's believed that when the DNases and carbohydrases are acting together, the DNA components are more effectively dispersed or removed. It is thus advantageous to formulate DNases with carbohydrases such as cellulases, amylases, mannanases and xylanases in cleaning compositions, e.g., for deep cleaning. One aspect of the invention relates to a method of formulating a cleaning composition comprising adding a DNase, at least one carbohydrase and a cleaning component, wherein the carbohydrase is a cellulase, an amylase, a mannanase or a xylanase.

The invention further relates to a kit intended for deep cleaning, wherein the kit comprises a solution of an enzyme mixture comprising a DNase and a carbohydrase, wherein the carbohydrase is a cellulase, an amylase, a mannanase or a xylanase.

In one aspect of the invention the carbohydrase is a cellulase. In one aspect, the invention relates to a cleaning composition comprising a DNase, a carbohydrase and a cleaning component, wherein the carbohydrase is a cellulase. In one aspect, the invention relates to a cleaning composition comprising a DNase, a carbohydrase and a cleaning component, wherein the carbohydrase is a cellulase, preferably selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86.

In one aspect of the invention the carbohydrase is an amylase.

In one aspect of the invention the carbohydrase is an amylase. In one aspect, the invention relates to a cleaning composition comprising a DNase, a carbohydrase and a cleaning component, wherein the carbohydrase is an amylase. In one aspect, the invention relates to a cleaning composition comprising a DNase, a carbohydrase and a cleaning component, wherein the carbohydrase is an amylase, preferably selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91.

In one aspect of the invention the carbohydrase is a mannanase. In one aspect, the invention relates to a cleaning composition comprising a DNase, a carbohydrase and a cleaning component, wherein the carbohydrase is a mannanase. In one aspect, the invention relates to a cleaning composition comprising a DNase, a carbohydrase and a cleaning component, wherein the carbohydrase is a mannanase, preferably a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82.

In one aspect of the invention the carbohydrase is a xylanase. In one aspect, the invention relates to a cleaning composition comprising a DNase, a carbohydrase and a cleaning component, wherein the carbohydrase is a xylanase. In one aspect, the invention relates to a cleaning composition comprising a DNase, a carbohydrase and a cleaning component, wherein the carbohydrase is a xylanase, preferably a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87.

The DNases to be formulated together with the carbohydrases or to be used together with the carbohydrases should be compatible with cleaning components. DNases are at present not standard ingredients in cleaning compositions. However, the applicant has identified DNases suitable for use in cleaning compositions, e.g., in WO 2017/060475, WO 2014/087011, WO 2015/155350 and WO 2015/155351. These applications also mentioned that DNases may be formulated with other enzymes, e.g., carbohydrases. However, none of these applications indicate that the DNases may have synergy with, e.g., cellulases. Enzymes, such as DNases should not only be compatible with the cleaning components, the DNases should also be compatible with other enzymes which may be present in a typical cleaning composition. Surprisingly, it was found that carbohydrases such as cellulases and DNases not only are compatible but even act synergistically in respect of biofilm reduction and removal, e.g., in deep cleaning.

Particularly useful DNases may be those of microbial origin. One embodiment of the invention relates to a cleaning composition comprising a DNase, a carbohydrase and at least one cleaning component, wherein the carbohydrase is a cellulase, an amylase, a mannanase or a xylanase and wherein the DNase is microbial, preferably obtained from bacteria or fungi. In one embodiment, the cleaning composition comprise a DNase from bacteria. One embodiment of the invention relates to a cleaning composition comprising a DNase, a carbohydrase and at least one cleaning component, wherein the carbohydrase is a cellulase, an amylase, a mannanase or a xylanase and wherein the DNase is obtained from *Bacillus*, preferably *Bacillus cibi, Bacillus horikoshii, Bacillus licheniformis, Bacillus subtilis, Bacillus horneckiae, Bacillus idriensis, Bacillus algicola, Bacillus vietnamensis, Bacillus hwajinpoensis, Bacillus indicus, Bacillus marisflavi* or *Bacillus luciferensis*.

As mentioned above the DNases to be used in a composition of the invention preferable belong to the NUC1 group of DNases. The NUC1 group of DNases may comprise one or more of the motifs [T/D/S][G/N]PQL (SEQ ID NO 69), [F/L/Y/I]A[N/R]D[L/I/P/V] (SEQ ID NO: 70), or C[D/N]T[A/R] (SEQ ID NO: 71). One embodiment of the invention relates to a cleaning composition comprising a DNase, a carbohydrase, selected from cellulases, amylases, mannanases and xylanases, and at least one cleaning component, wherein the DNase comprises one or more of the motifs [T/D/S][G/N]PQL, [F/L/Y/I]A[N/R]D[L/I/P/V] or C[D/N]T[A/R]. The DNases preferably additionally comprises a NUC1_A domain [D/Q][I/V]DH (SEQ ID NO 72).

One embodiment of the invention relates to a cleaning composition comprising a DNase, a carbohydrase, selected from cellulases, amylases, mannanases and xylanases, and at least one cleaning component, wherein the DNase comprises one or more motifs selected from the motifs [T/D/S][G/N]PQL, [F/L/Y/I]A[N/R]D[L/I/P/V], C[D/N]T[A/R] and [D/Q][I/V]DH.

One preferred embodiment of the invention relates to a cleaning composition comprising a DNase, a carbohydrase, selected from cellulases, amylases, mannanases and xylanases, and at least one cleaning component, wherein the DNase comprises two or more motifs selected from the motifs [T/D/S][G/N]PQL, [F/L/Y/I]A[N/R]D[L/I/P/V], C[D/N]T[A/R] and [D/Q][I/V]DH.

One preferred embodiment of the invention relates to a cleaning composition comprising a DNase, a carbohydrase, selected from cellulases, amylases, mannanases and xylanases, and at least one cleaning component, wherein the DNase comprises three or more motifs selected from the motifs [T/D/S][G/N]PQL, [F/L/Y/I]A[N/R]D[L/I/P/V], C[D/N]T[A/R] and [D/Q][I/V]DH.

One preferred embodiment of the invention relates to a cleaning composition comprising a DNase, a carbohydrase, selected from cellulases, amylases, mannanases and xylanases, and at least one cleaning component, wherein the DNase comprises four or more motifs selected from the motifs [T/D/S][G/N]PQL, [F/L/Y/I]A[N/R]D[L/I/P/V], C[D/N]T[A/R] and [D/Q][I/V]DH.

One preferred embodiment of the invention relates to a cleaning composition comprising a DNase, a carbohydrase, selected from cellulases, amylases, mannanases and xylanases, and at least one cleaning component, wherein the DNase comprises all five motifs [T/D/S][G/N]PQL, [F/L/Y/I]A[N/R]D[L/I/P/V], C[D/N]T[A/R] and [D/Q][I/V]DH.

The DNases to be added to a composition of the invention preferably belong to the group of DNases comprised in the GYS-clade, which are NUC1 and NUC1_A DNases further comprising the conservative motifs [D/M/L][S/T]GYSR[D/N] (SEQ ID NO: 73) or ASXNRSKG (SEQ ID NO: 74) and which share similar structural and functional properties. The DNases of the GYS-clade are preferably obtained from *Bacillus* genus.

One embodiment of the invention relates to a cleaning composition comprising a DNase, at least one carbohydrase and a cleaning component, wherein the carbohydrase is a cellulase, an amylase, a mannanase or a xylanase and wherein the DNase comprises one or both of the motif(s) [D/M/L][S/T]GYSR[D/N] (SEQ ID NO: 73) or ASXNR-SKG (SEQ ID NO: 74).

In a particularly preferred embodiment the *Bacillus* DNase comprises one or both of the motif(s) [D/M/L][S/T]GYSR[D/N] (SEQ ID NO: 73) or ASXNRSKG (SEQ ID NO: 74). In another particularly preferred embodiment the DNase comprises one or both of the motif(s) [D/M/L][S/T]GYSR[D/N] (SEQ ID NO: 73) or ASXNRSKG (SEQ ID NO: 74) and is obtained from *Bacillus cibi*. In yet another preferred embodiment the DNase comprises the amino acid sequence shown in SEQ ID NO 13 or DNases closely related hereto.

One embodiment of the invention relates to a cleaning composition comprising a DNase, at least one carbohydrase and a cleaning component, wherein the carbohydrase is a cellulase, an amylase, a mannanase or a xylanase and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 13.

Other preferred DNases include those comprising the amino acid sequence shown in SEQ ID NO 65 and 66.

One embodiment of the invention relates to a cleaning composition comprising a DNase, at least one carbohydrase and a cleaning component, wherein the carbohydrase is a cellulase, an amylase, a mannanase or a xylanase and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 65.

One embodiment of the invention relates to a cleaning composition comprising a DNase, at least one carbohydrase and a cleaning component, wherein the carbohydrase is a cellulase, an amylase, a mannanase or a xylanase and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 66.

The DNase may also preferably be fungal. Particularly preferred are DNases obtained from *Aspergillus* in particular, *Aspergillus oryzae*.

One embodiment of the invention relates to a cleaning composition comprising a DNase, at least one carbohydrase and a cleaning component, wherein the carbohydrase is a cellulase, an amylase, a mannanase or a xylanase and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 67.

Other particularly preferred are DNases obtained from *Trichoderma* in particular, *Trichoderma harzianum*.

One embodiment of the invention relates to a cleaning composition comprising a DNase, at least one carbohydrase and a cleaning component, wherein the carbohydrase is a cellulase, an amylase, a mannanase or a xylanase and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 68.

One embodiment relates to a cleaning composition comprising a *Bacillus* DNase, a cellulase and at least one cleaning component, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86.

One embodiment relates to a cleaning composition comprising a *Bacillus* DNase, an amylase and at least one cleaning component, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91.

One embodiment relates to a cleaning composition comprising a *Bacillus* DNase, a mannanase and at least one cleaning component, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82.

One embodiment relates to a cleaning composition comprising a *Bacillus* DNase, a xylanase and at least one cleaning component, wherein the xylanase is selected from preferably a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87.

One embodiment relates to a cleaning composition comprising a DNase, a cellulase and at least one cleaning component, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 13.

One embodiment relates to a cleaning composition comprising a DNase, an amylase and at least one cleaning component, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 13.

One embodiment relates to a cleaning composition comprising a DNase, a mannanase and at least one cleaning component, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 13.

One embodiment relates to a cleaning composition comprising a DNase, a xylanase and at least one cleaning component, wherein the xylanase is selected from preferably a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 13.

One embodiment relates to a cleaning composition comprising a DNase, a cellulase and at least one cleaning component, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 65.

One embodiment relates to a cleaning composition comprising a DNase, an amylase and at least one cleaning component, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 65.

One embodiment relates to a cleaning composition comprising a DNase, a mannanase and at least one cleaning component, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 65.

One embodiment relates to a cleaning composition comprising a DNase, a xylanase and at least one cleaning component, wherein the xylanase is selected from preferably a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 65.

One embodiment relates to a cleaning composition comprising a DNase, a cellulase and at least one cleaning component, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 66.

One embodiment relates to a cleaning composition comprising a DNase, an amylase and at least one cleaning component, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 66.

One embodiment relates to a cleaning composition comprising a DNase, a mannanase and at least one cleaning component, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 66.

One embodiment relates to a cleaning composition comprising a DNase, a xylanase and at least one cleaning component, wherein the xylanase is selected from preferably a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 66.

One embodiment relates to a cleaning composition comprising a DNase, a cellulase and at least one cleaning component, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 67.

One embodiment relates to a cleaning composition comprising a DNase, an amylase and at least one cleaning component, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 67.

One embodiment relates to a cleaning composition comprising a DNase, a mannanase and at least one cleaning component, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 67.

One embodiment relates to a cleaning composition comprising a DNase, a xylanase and at least one cleaning component, wherein the xylanase is selected from preferably a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 67.

One embodiment relates to a cleaning composition comprising a DNase, a cellulase and at least one cleaning component, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 68.

One embodiment relates to a cleaning composition comprising a DNase, an amylase and at least one cleaning component, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 68.

One embodiment relates to a cleaning composition comprising a DNase, a mannanase and at least one cleaning component, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 68.

One embodiment relates to a cleaning composition comprising a DNase, a xylanase and at least one cleaning component, wherein the xylanase is selected from preferably a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 68.

One embodiment of the invention relates to a composition comprising
  a) at least 0.001 ppm, e.g., 0.1 ppm or 1 ppm of at least one polypeptide having DNase activity, wherein the DNase is selected for the group consisting of:
  i) a DNase comprising one or more of the motif(s) [T/D/S][G/N]PQL (SEQ ID NO 69), [F/L/Y/1]A[N/R]D[L/I/P/V] (SEQ ID NO: 70), C[D/N]T[A/R] (SEQ ID NO: 71);
  ii) a DNase comprising the motif [D/Q][I/V]DH (SEQ ID NO 72);
  iii) a DNase comprising one or both of the motif(s) [D/M/L][S/T]GYSR[D/N] (SEQ ID NO: 73) or ASXNRSKG (SEQ ID NO: 74);
  iv) a DNase comprising one or both of the motifs [V/I]PL[S/A]NAWK (SEQ ID NO: 75) or NPQL (SEQ ID NO: 76);
  v) a DNase comprising one or both of the motifs P[Q/E]L[W/Y] (SEQ ID NO: 77) or [K/H/E]NAW (SEQ ID NO:78);
  vi) a DNase selected from: a polypeptide having at least 80% sequence identity to the polypeptide shown in SEQ ID NO: 1, a polypeptide having at least 80% sequence identity to the polypeptide shown in SEQ ID NO: 2, a polypeptide having at least 80% sequence identity to the polypeptide shown in SEQ ID NO: 3, a polypeptide having at least 80% sequence identity to the polypeptide shown in SEQ ID NO: 4, a polypeptide having at least 80% sequence identity to the polypeptide shown in SEQ ID NO: 5, a polypeptide having at least 80% sequence identity to the polypeptide shown in SEQ ID NO: 6, a polypeptide having at least 80% sequence identity to the polypeptide shown in SEQ ID NO: 7, a polypeptide having at least 80% sequence identity to the polypeptide shown in SEQ ID NO: 8, a polypeptide having at least 80% sequence identity to the polypeptide shown in SEQ ID NO: 9, a polypeptide having at least 80% sequence identity to the polypeptide shown in SEQ ID NO: 10, a polypeptide having at least 80% sequence identity to the polypeptide shown in SEQ ID NO: 11, a polypeptide having at least 80% sequence identity to the polypeptide shown in SEQ ID NO: 12, a polypeptide having at least 80% sequence identity to the polypeptide shown in SEQ ID NO: 13, a polypeptide having at least 80% sequence identity to the polypeptide shown in SEQ ID NO: 14, a polypeptide having at least 80% sequence identity to the polypeptide shown in SEQ ID NO: 15, a polypeptide having at least 80% sequence identity to the polypeptide shown in SEQ ID NO: 16, a polypeptide having at least 80% sequence identity to the polypeptide shown in SEQ ID NO: 17, a polypeptide having at least 80% sequence identity to the polypeptide shown in SEQ ID NO: 18, a polypeptide having at least 80% sequence identity to the polypeptide shown in SEQ ID NO: 19, a polypeptide having at least 80% sequence identity to the polypeptide shown in SEQ ID NO: 20, a polypeptide having at least 80% sequence identity to the polypeptide shown in SEQ ID NO: 21, a polypeptide having at least 80% sequence identity to the polypeptide shown in SEQ ID NO: 22, a polypeptide having at least 80% sequence identity to the polypeptide shown in SEQ ID NO: 23, a polypeptide having at least 80% sequence identity to the polypeptide shown in SEQ ID NO: 24, a polypeptide having at least 80% sequence identity to the polypeptide shown in SEQ ID NO: 25, a polypeptide having at least 80% sequence identity to the polypeptide shown in SEQ ID NO: 26, a polypeptide having at least 80% sequence identity to the polypeptide shown in SEQ ID NO: 27, a polypeptide having at least 80% sequence identity to the polypeptide shown in SEQ ID NO: 28, a polypeptide having at least 80% sequence identity to the polypeptide shown in SEQ ID NO: 29, a polypeptide having at least 80% sequence identity to the polypeptide shown in SEQ ID NO: 30, a polypeptide having at least 80% sequence identity to the polypeptide shown in SEQ ID NO: 31, a polypeptide having at least 80% sequence identity to the polypeptide shown in SEQ ID NO: 32, a polypeptide having at least 80% sequence identity to the polypeptide shown in SEQ ID NO: 33, a polypeptide having at least 80% sequence identity to the polypeptide shown in SEQ ID NO: 34, a polypeptide having at least 80% sequence identity to the polypeptide shown in SEQ ID NO: 35, a polypeptide having at least 80% sequence identity to the polypeptide shown in SEQ ID NO: 36, a polypeptide having at least 80% sequence identity to the polypeptide shown in SEQ ID NO: 37, a polypeptide having at least 80% sequence identity to the polypeptide shown in SEQ ID NO: 38, a polypeptide having at least 80% sequence identity to the polypeptide shown in SEQ ID NO: 39, a polypeptide having at least 80% sequence identity to the polypeptide shown in SEQ ID NO: 40, a polypeptide having at least 80% sequence identity to the polypeptide shown in SEQ ID NO: 41, a polypeptide having at least 80% sequence identity to the polypeptide shown in SEQ ID NO: 42, a polypeptide having at least 80% sequence identity to the polypeptide shown in SEQ ID NO: 43, a polypeptide having at least 80% sequence identity to the polypeptide shown in SEQ ID NO: 44, a polypeptide having at least 80% sequence identity to the polypeptide shown in SEQ ID NO: 45, a polypeptide having at least 80% sequence identity to the polypeptide shown in SEQ ID NO: 46, a polypeptide having at least 80% sequence identity to the polypeptide shown in SEQ ID NO: 47, a polypeptide having at least 80% sequence identity to the polypeptide shown in SEQ ID NO: 48, a polypeptide having at least 80% sequence identity to the polypeptide shown in SEQ ID NO: 49, a polypeptide having at least 80% sequence identity to the polypeptide shown in SEQ ID NO: 50, a polypeptide having at least 80% sequence identity to the polypeptide shown in SEQ ID NO: 51, a polypeptide having at least 80% sequence identity to the polypeptide shown in SEQ ID NO: 52, a polypeptide having at least 80% sequence identity to the polypeptide shown in SEQ ID NO: 53, a polypeptide having at least 80% sequence identity to the polypeptide shown in SEQ ID NO: 54, a polypeptide having at least 80% sequence identity to the polypeptide shown in SEQ ID NO: 55, a polypeptide having at least 80% sequence identity to the polypeptide shown in SEQ ID NO: 56, a polypeptide having at least 80% sequence identity to the polypeptide shown in SEQ ID NO: 57, a polypeptide having at least 80% sequence identity to the polypeptide shown in SEQ ID NO: 58, a polypeptide having at least 80% sequence identity to the polypeptide shown in SEQ ID NO: 59, a polypeptide having at least 80% sequence identity to the polypeptide shown in SEQ ID NO: 60, a polypeptide having at least 80% sequence identity to the polypeptide shown in SEQ ID NO: 61, a polypeptide having at least 80% sequence identity to the polypeptide shown in SEQ ID NO: 62, a polypeptide having at least 80% sequence identity to the polypeptide shown in SEQ ID NO: 63, a polypeptide having at least 80% sequence identity to the polypeptide shown in SEQ ID NO: 64, a polypeptide having at least 80% sequence identity to the polypeptide shown in SEQ ID NO: 65, a polypeptide having at least 80% sequence identity to the polypeptide shown in SEQ ID NO: 66, a polypeptide having at least 80% sequence identity to the polypeptide shown in SEQ ID NO: 67, and a polypeptide having at least 80% sequence identity to the polypeptide shown in SEQ ID NO: 68; and b) at least 0.001 ppm, e.g., 0.1 ppm or 1 ppm of one or more carbohydrase, wherein the carbohydrase is selected from the group consisting of:
  i. a cellulase selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 80% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86;
  ii. a xylanase selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87;
  iii. a mannanase selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82;
  iv. an amylase selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91; and c) at least one additional component, e.g., cleaning component, preferably selected from surfactants, builders, bleach components, polymers and dispersing agents.

The carbohydrase and DNase may be included in the cleaning composition of the present invention at a level of from 0.01 to 1000 ppm, from 1 ppm to 1000 ppm, from 10 ppm to 1000 ppm, from 50 ppm to 1000 ppm, from 100 ppm to 1000 ppm, from 150 ppm to 1000 ppm, from 200 ppm to 1000 ppm, from 250 ppm to 1000 ppm, from 250 ppm to 750 ppm, from 250 ppm to 500 ppm. The DNases above may be combined with carbohydrases to form a blend to be added to the wash liquor solution according to the invention. The concentration of the DNase in the wash liquor solution is typically in the range of wash liquor from 0.00001 ppm to 10 ppm, from 0.00002 ppm to 10 ppm, from 0.0001 ppm to 10 ppm, from 0.0002 ppm to 10 ppm, from 0.001 ppm to 10 ppm, from 0.002 ppm to 10 ppm, from 0.01 ppm to 10 ppm, from 0.02 ppm to 10 ppm, 0.1 ppm to 10 ppm, from 0.2 ppm to 10 ppm, from 0.5 ppm to 5 ppm. The concentration of the carbohydrases in the wash liquor solution is typically in the range of wash liquor from 0.00001 ppm to 10 ppm, from 0.00002 ppm to 10 ppm, from 0.0001 ppm to 10 ppm, from 0.0002 ppm to 10 ppm, from 0.001 ppm to 10 ppm, from 0.002 ppm to 10 ppm, from 0.01 ppm to 10 ppm, from 0.02 ppm to 10 ppm, 0.1 ppm to 10 ppm, from 0.2 ppm to 10 ppm, from 0.5 ppm to 5 ppm. The DNases may be combined with any of the carbohydrases below to form a blend to be added to a composition according to the invention.

One embodiment relates to a cleaning composition comprising a DNase, a carbohydrase and at least one cleaning component, wherein the amount of DNase in the composition is from 0.01 to 1000 ppm and the amount of carbohydrase is from 0.01 to 1000 ppm.

The invention relates to cleaning compositions comprising an enzyme combination of the present invention in combination with one or more additional cleaning composition component(s). The choice of additional components is within the skill of the artisan and includes conventional ingredients, including the exemplary non-limiting components set forth below.

The choice of cleaning components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 0.1% to about 15%, such as about 1% to about 40%, or about 3% to about 20%, or about 3% to about 10%. The surfactant(s) is chosen based on the desired cleaning application, and may include any conventional surfactant(s) known in the art. When included therein the detergent will usually contain from about 1% to about 40% by weight of an anionic surfactant, such as from about 5% to about 30%, including from about 5% to about 15%, or from about 15% to about 20%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

When included therein the detergent will usually contain from about 1% to about 40% by weigh of a cationic surfactant, for example from about 0.5% to about 30%, in particular from about 1% to about 20%, from about 3% to about 10%, such as from about 3% to about 5%, from about 8% to about 12% or from about 10% to about 12%. Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, ester quats, and combinations thereof.

When included therein the detergent will usually contain from about 0.2% to about 40% by weight of a nonionic surfactant, for example from about 0.5% to about 30%, in particular from about 1% to about 20%, from about 3% to about 10%, such as from about 3% to about 5%, from about 8% to about 12%, or from about 10% to about 12%. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof. When included therein the detergent will usually contain from about 0.01% to about 10% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl) amine oxide, and combinations thereof. When included therein the detergent will usually contain from about 0.01% to about 10% by weight of a zwitterionic surfactant. Non-limiting examples of zwitterionic surfactants include betaines such as alkyldimethylbetaines, sulfobetaines, and combinations thereof.

Builders and Co-Builders

The detergent composition may contain about 0-65% by weight, such as about 5% to about 50%, such as from about 0.5% to about 20% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1-ol), triethanolamine (TEA, also known as 2,2',2"-nitrilotriethan-1-ol), and (carboxymethyl)inulin (CMI), and combinations thereof.

The detergent composition may also contain 0-50% by weight, such as about 5% to about 30%, of a detergent co-builder. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (H EDP), ethylenediaminetetra(methylenephosphonic acid) (EDTMPA), diethylenetriaminepentakis(methylenephosphonic acid) (DTMPA or DTPMPA), N-(2-hydroxyethyl)iminodiacetic acid (EDG), aspartic acid-N-monoacetic acid (ASMA), aspartic acid-N, N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MI DA), α-alanine-N, N-diacetic acid (α-ALDA), serine-N,N-diacetic acid (SEDA), isoserine-N, N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N, N-diacetic acid (SMDA), N-(2-hydroxyethyl)ethylenediamine-N,N',N"-triacetic acid (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 2009/102854, U.S. Pat. No. 5,977,053.

Bleaching Systems

The detergent may contain 0-30% by weight, such as about 1% to about 20%, such as from about 0.01 to about 10 wt. % of a bleaching system. Any bleaching system comprising components known in the art for use in cleaning detergents may be utilized. Suitable bleaching system components include sources of hydrogen peroxide; sources of peracids; and bleach catalysts or boosters.

Sources of Hydrogen Peroxide:

Suitable sources of hydrogen peroxide are inorganic persalts, including alkali metal salts such as sodium percarbonate and sodium perborates (usually mono- or tetrahydrate), and hydrogen peroxideurea (1/1).

Sources of Peracids:

Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.

a) Suitable preformed peracids include, but are not limited to, peroxycarboxylic acids such as peroxybenzoic acid and its ring-substituted derivatives, peroxy-α-naphthoic acid, peroxyphthalic acid, peroxylauric acid, peroxystearic acid, ε-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyldiperoxybutanedioic acid, and diperoxyphthalic, -isophthalic and -terephthalic acids; perimidic acids; peroxymonosulfuric acid; peroxydisulfuric acid; peroxyphosphoric acid; peroxysilicic acid; and mixtures of said compounds. It is understood that the peracids mentioned may in some cases be best added as suitable salts, such as alkali metal salts (e.g., Oxone®) or alkaline earth-metal salts.

b) Suitable bleach activators include those belonging to the class of esters, amides, imides, nitriles or anhydrides and, where applicable, salts thereof. Suitable examples are tetraacetylethylenediamine (TAED), sodium 4-[(3,5,5-trimethylhexanoyl)oxy]benzene-1-sulfonate (ISONOBS), sodium 4-(dodecanoyloxy)benzene-1-sulfonate (LOBS), sodium 4-(decanoyloxy)benzene-1-sulfonate, 4-(decanoyloxy)benzoic acid (DOBA), sodium 4-(nonanoyloxy)benzene-1-sulfonate (NOBS), and/or those disclosed in WO 98/17767. A particular family of bleach activators of interest was disclosed in EP 624154 and particularly preferred in that family is acetyl triethyl citrate (ATC). ATC or a short chain triglyceride like triacetin has the advantage that they are environmentally friendly. Furthermore, acetyl triethyl citrate and triacetin have good hydrolytical stability in the product upon storage and are efficient bleach activators. Finally, ATC is multifunctional, as the citrate released in the perhydrolysis reaction may function as a builder.

Bleach Catalysts and Boosters

The bleaching system may also include a bleach catalyst or booster.

Some non-limiting examples of bleach catalysts that may be used in the compositions of the present invention include manganese oxalate, manganese acetate, manganese-collagen, cobalt-amine catalysts and manganese triazacyclononane (MnTACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(O)3Mn(Me3-TACN)](PF6)2, and [2,2',2"-nitrilotris(ethane-1,2-diylazanylylidene-κN-methanylylidene)triphenolato-κ3O]manganese(III). The bleach catalysts may also be other metal compounds; such as iron or cobalt complexes.

In some embodiments, where a source of a peracid is included, an organic bleach catalyst or bleach booster may be used having one of the following formulae:

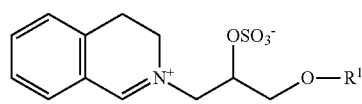

(i)

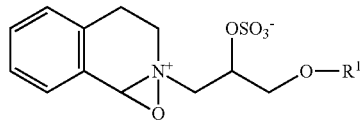

(ii)

(iii) and mixtures thereof; wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

Other exemplary bleaching systems are described, e.g., in WO 2007/087258, WO 2007/087244, WO 2007/087259, EP 1867708 (Vitamin K) and WO 2007/087242. Suitable photobleaches may for example be sulfonated zinc or aluminium phthalocyanines.

Metal Care Agents

Metal care agents may prevent or reduce the tarnishing, corrosion or oxidation of metals, including aluminium, stainless steel and non-ferrous metals, such as silver and copper. Suitable examples include one or more of the following:

(a) benzatriazoles, including benzotriazole or bis-benzotriazole and substituted derivatives thereof. Benzotriazole derivatives are those compounds in which the available substitution sites on the aromatic ring are partially or completely substituted. Suitable substituents include linear or branch-chain Ci-C20-alkyl groups (e.g., C1-C20-alkyl groups) and hydroxyl, thio, phenyl or halogen such as fluorine, chlorine, bromine and iodine.

(b) metal salts and complexes chosen from the group consisting of zinc, manganese, titanium, zirconium, hafnium, vanadium, cobalt, gallium and cerium salts and/or complexes, the metals being in one of the oxidation states II, III, IV, V or VI. In one aspect, suitable metal salts and/or metal complexes may be chosen from the group consisting of Mn(II) sulphate, Mn(II) citrate, Mn(II) stearate, Mn(II) acetylacetonate, K^TiF6 (e.g., K2TiF6), K^ZrF6 (e.g., K2ZrF6), CoSO4, Co(NOs)2 and Ce(NOs)3, zinc salts, for example zinc sulphate, hydrozincite or zinc acetate.

(c) silicates, including sodium or potassium silicate, sodium disilicate, sodium metasilicate, crystalline phyllosilicate and mixtures thereof.

Further suitable organic and inorganic redox-active substances that act as silver/copper corrosion inhibitors are disclosed in WO 94/26860 and WO 94/26859. Preferably the composition of the invention comprises from 0.1 to 5% by weight of the composition of a metal care agent, preferably the metal care agent is a zinc salt.

Hydrotropes

The detergent may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Polymers

The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl) cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Suitable examples include PVP-K15, PVP-K30, ChromaBond S-400, ChromaBond S-403E and Chromabond S-100 from Ashland Aqualon, and Sokalan® HP 165, Sokalan® HP 50 (Dispersing agent), Sokalan® HP 53 (Dispersing agent), Sokalan® HP 59 (Dispersing agent), Sokalan® HP 56 (dye transfer inhibitor), Sokalan® HP 66 K (dye transfer inhibitor) from BASF. Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated. Particularly preferred polymer is ethoxylated homopolymer Sokalan® HP 20 from BASF.

Fabric Hueing Agents

The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO 2005/003274, WO 2005/003275, WO 2005/003276 and EP 1876226 (hereby incorporated by reference). The detergent composition preferably comprises from about 0.00003 wt. % to about 0.2 wt. %, from about 0.00008 wt. % to about 0.05 wt. %, or even from about 0.0001 wt. % to about 0.04 wt. % fabric hueing agent. The composition may comprise from 0.0001 wt. % to 0.2 wt. % fabric hueing agent, this may be especially preferred when the composition is in the form of a unit dose pouch. Suitable hueing agents are also disclosed in, e.g., WO 2007/087257 and WO 2007/087243.

Enzymes

The detergent additive as well as the detergent composition may comprise one or more additional enzymes such as one or more protease, lipase, cutinase, pectinase, arabinase, galactanase, xylanase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Proteases

The term "protease activity" means a proteolytic activity (EC 3.4). Proteases usably in cleaning compositions of the present invention are mainly endopeptidases (EC 3.4.21). There are several protease activity types: The three main activity types are: trypsin-like where there is cleavage of amide substrates following Arg or Lys at P1, chymotrypsin-like where cleavage occurs following one of the hydrophobic amino acids at P1, and elastase-like with cleavage following an Ala at P1.

The most widely used proteases in the detergent industry such as laundry and dish wash are the serine proteases. Serine proteases is a subgroup of proteases characterised by having a serine in the active site, which forms a covalent adduct with the substrate. Serine proteases are characterized by having two active site amino acid residues apart from the serine, namely a histidine residue and an aspartic acid residue. Subtilase refer to a sub-group of serine protease according to Siezen et al., 1991, *Protein Engng.* 4: 719-737 and Siezen et al., 1997, *Protein Science* 6: 501-523. The subtilases may be divided into 6 sub-divisions, i.e., the Subtilisin family, the Thermitase family, the Proteinase K family, the Lantibiotic peptidase family, the Kexin family and the Pyrolysin family.

Suitable proteases for the compositions of the invention include those of bacterial, fungal, plant, viral or animal origin, e.g., vegetable or microbial origin. Microbial origin is preferred. Chemically modified or protein engineered mutants are included. It may be an alkaline protease, such as a serine protease or a metalloprotease. A serine protease may for example be of the 51 family, such as trypsin, or the S8 family such as subtilisin. A metalloproteases protease may for example be a thermolysin from, e.g., family M4 or other metalloprotease such as those from M5, M7 or M8 families.

Examples of subtilases are those derived from *Bacillus* such as *Bacillus lentus, Bacillus alkalophilus, Bacillus subtilis, Bacillus amyloliquefaciens, Bacillus pumilus* and *Bacillus gibsonii* described in; U.S. Pat. No. 7,262,042 and WO 2009/021867, and subtilisin lentus, subtilisin Novo, subtilisin Carlsberg, *Bacillus licheniformis*, subtilisin BPN', subtilisin 309, subtilisin 147 and subtilisin 168 described in WO 89/06279 and protease PD138 described in (WO 93/18140). Other useful proteases may be those described in WO 92/175177, WO 01/16285, WO 02/26024 and WO 02/16547. Examples of trypsin-like proteases are trypsin (e.g., of porcine or bovine origin) and the *Fusarium* protease described in WO 89/06270, WO 94/25583 and WO 2005/040372, and the chymotrypsin proteases derived from *Cellumonas* described in WO 2005/052161 and WO 2005/052146.

A further preferred protease is the alkaline protease from *Bacillus lentus* DSM 5483, as described for example in WO 95/23221, and variants thereof which are described in WO 92/21760, WO 95/23221, EP 1921147 and EP 1921148.

Examples of metalloproteases are the neutral metalloproteases as described in WO 2007/044993 (Genencor Int.) such as those derived from *Bacillus amyloliquefaciens*.

Examples of useful proteases are the variants described in: WO 92/19729, WO 96/034946, WO 98/20115, WO 98/20116, WO 99/11768, WO 01/44452, WO 03/006602, WO 2004/03186, WO 2004/041979, WO 2007/006305, WO 2011/036263, WO 2011/036264, especially protease variants comprising a substitution in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269, wherein the positions correspond to the positions of the *Bacillus lentus* protease shown in SEQ ID NO 69. More preferred the protease variants may comprise one or more of the mutations selected from the group consisting of: S3T, V4I, S9R, S9E, A15T, S24G, S24R, K27R, N42R, S55P, G59E, G59D, N60D, N60E, V66A, N74D, S85R, A96S, S97G, S97D, S97A, S97SD, S99E, S99D, S99G, S99M, S99N, S99R, S99H, S101A, V102I, V102Y, V102N, S104A, G116V, G116R, H118D, H118N, A120S, S126L, P127Q, S128A, S154D, A156E, G157D, G157P, S158E, Y161A, R164S, Q176E, N179E, S182E, Q185N, A188P, G189E, V193M, N198D, V199I, Y203W, S206G, L211Q, L211D, N212D, N212S, M216S, A226V, K229L, Q230H, Q239R, N246K, N255W, N255D, N255E, L256E, L256D T268A and R269H. The protease variants are preferably variants of the *Bacillus lentus* protease (Savinase®) shown in SEQ ID NO 79 or the *Bacillus amylolichenifaciens* protease (BPN') shown in SEQ ID NO 80. The protease variants preferably have at least 80% sequence identity to SEQ ID NO 79 or SEQ ID NO 80.

A protease variant comprising a substitution at one or more positions corresponding to positions 171, 173, 175, 179, or 180 of SEQ ID NO: 81, wherein said protease variant has a sequence identity of at least 75% but less than 100% to SEQ ID NO: 81.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Blaze®, Blaze Evity® 100T, Blaze Evity® 125T, Blaze Evity® 150T, Neutrase®, Everlase® and Esperase® (Novozymes A/S), those sold under the tradename Maxatase®, Maxacal®, Maxapem®, Purafect Ox®, Purafect OxP®, Puramax®, FN2®, FN3®, FN4®, Excellase®, Excellenz P1000™, Excellenz P1250™, Eraser®, Preferenz P100™, Purafect Prime®, Preferenz P110™, Effectenz P1000™, Purafect®™, Effectenz P1050™, Purafect Ox®™, Effectenz P2000™, Purafast®, Properase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Peroxidases/Oxidases

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include Guardzyme™ (Novozymes A/S).

Lipases and Cutinases:

Suitable lipases and cutinases include those of bacterial or fungal origin. Chemically modified or protein engineered mutant enzymes are included. Examples include lipase from *Thermomyces*, e.g., from *T. lanuginosus* (previously named *Humicola lanuginosa*) as described in EP 258068 and EP 305216, cutinase from *Humicola*, e.g., *H. insolens* (WO 96/13580), lipase from strains of *Pseudomonas* (some of these now renamed to *Burkholderia*), e.g., *P. alcaligenes* or *P. pseudoalcaligenes* (EP 218272), *P. cepacia* (EP 331376), P. sp. strain SD705 (WO 95/06720 & WO 96/27002), *P. wisconsinensis* (WO 96/12012), GDSL-type *Streptomyces* lipases (WO 2010/065455), cutinase from *Magnaporthe grisea* (WO 2010/107560), cutinase from *Pseudomonas mendocina* (U.S. Pat. No. 5,389,536), lipase from *Thermobifida fusca* (WO 2011/084412), *Geobacillus stearothermophilus* lipase (WO 2011/084417), lipase from *Bacillus subtilis* (WO 2011/084599), and lipase from *Streptomyces griseus* (WO 2011/150157) and *S. pristinaespiralis* (WO 2012/137147).

Other examples are lipase variants such as those described in EP 407225, WO 92/05249, WO 94/01541, WO 94/25578, WO 95/14783, WO 95/30744, WO 95/35381, WO 95/22615, WO 96/00292, WO 97/04079, WO 97/07202, WO 00/34450, WO 00/60063, WO 01/92502, WO 2007/87508 and WO 2009/109500.

Preferred commercial lipase products include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g., acyltransferases with homology to *Candida antarctica* lipase A (WO 2010/111143), acyltransferase from *Mycobacterium smegmatis* (WO 2005/056782), perhydrolases from the CE 7 family (WO 2009/067279), and variants of the *M. smegmatis* perhydrolase in particular the S54V variant used in the commercial product Gentle Power Bleach from Huntsman Textile Effects Pte Ltd (WO 2010/100028).

Peroxidases/Oxidases

A peroxidase according to the invention is a peroxidase enzyme comprised by the enzyme classification EC 1.11.1.7, as set out by the Nomenclature Committee of the International Union of Biochemistry and Molecular Biology (IUBMB), or any fragment derived therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179486), and variants thereof as those described in WO 93/24618, WO 95/10602, and WO 98/15257.

A suitable peroxidase includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions. Preferably, the haloperoxidase is a vanadium haloperoxidase, i.e., a vanadate-containing haloperoxidase. Haloperoxidases have been isolated from many different fungi, in particular from the fungus group dematiaceous hyphomycetes, such as Caldariomyces, e.g., *C. fumago, Alternaria, Curvularia*, e.g., *C. verruculosa* and *C. inaequalis, Drechslera, Ulocladium* and *Botrytis*.

Haloperoxidases have also been isolated from bacteria such as *Pseudomonas*, e.g., *P. pyrrocinia* and *Streptomyces*, e.g., *S. aureofaciens*.

A suitable oxidase includes in particular, any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5). Preferred laccase enzymes are enzymes of microbial origin. The enzymes may be derived from plants, bacteria or fungi (including filamentous fungi and yeasts). Suitable examples from fungi include a laccase derivable from a strain of *Aspergillus, Neurospora*, e.g., *N. crassa, Podospora, Botrytis, Collybia, Fomes, Lentinus, Pleurotus, Trametes*, e.g., *T. villosa* and *T. versicolor, Rhizoctonia*, e.g., *R. solani, Coprinopsis*, e.g., *C. cinerea, C. comatus, C. friesii*, and *C. plicatilis, Psathyrella*, e.g., *P. condelleana, Panaeolus*, e.g., *P. papilionaceus, Myceliophthora*, e.g., *M. thermophila, Schytalidium*, e.g., *S. thermophilum, Polyporus*, e.g., *P. pinsitus, Phlebia*, e.g., *P. radiata* (WO 92/01046), or *Coriolus*, e.g., *C. hirsutus* (JP 2238885). Suitable examples from bacteria include a laccase derivable from a strain of *Bacillus*. A laccase derived from *Coprinopsis* or *Myceliophthora* is preferred; in particular, a laccase derived from *Coprinopsis cinerea*, as disclosed in WO 97/08325; or from *Myceliophthora thermophila*, as disclosed in WO 95/33836.

Dispersants

The cleaning compositions of the present invention can also contain dispersants. In particular, powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The cleaning compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent

The cleaning compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxy-ethylamino)-s-triazin-6-ylamino) stilbene-2, 2'-disulfonate, 4,4'-bis-(4-phenyl-1,2,3-triazol-2-yl)stilbene-2,2'-disulfonate and sodium 5-(2H-naphtho[1,2-d][1,2,3] triazol-2-yl)-2-[(E)-2-phenylvinyl]benzenesulfonate.

Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt. % to upper levels of 0.5 or even 0.75 wt. %.

Soil Release Polymers

The cleaning compositions of the present invention may also include one or more soil release polymers which aid the removal of soils from fabrics such as cotton and polyester based fabrics, in particular, the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers is amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore, random graft co-polymers are suitable soil release polymers. Suitable graft co-polymers are described in more detail in WO 2007/138054, WO 2006/108856 and WO 2006/113314 (hereby incorporated by reference). Suitable polyethylene glycol polymers include random graft co-polymers comprising: (i) hydrophilic backbone comprising polyethylene glycol; and (ii) side chain(s) selected from the group consisting of: C4-C25 alkyl group, polypropylene, polybutylene, vinyl ester of a saturated C1-C6 mono-carboxylic acid, C1-C6 alkyl ester of acrylic or methacrylic acid, and mixtures thereof. Suitable polyethylene glycol polymers have a polyethylene glycol backbone with random grafted polyvinyl acetate side chains. The average molecular weight of the polyethylene glycol backbone can be in the range of from 2,000 Da to 20,000 Da, or from 4,000 Da to 8,000 Da. The molecular weight ratio of the polyethylene glycol backbone to the polyvinyl acetate side chains can be in the range of from 1:1 to 1:5, or from 1:1.2 to 1:2. The average number of graft sites per ethylene oxide units can be less than 1, or less than 0.8, the average number of graft sites per ethylene oxide units can be in the range of from 0.5 to 0.9, or the average number of graft sites per ethylene oxide units can be in the range of from 0.1 to 0.5, or from 0.2 to 0.4. A suitable polyethylene glycol polymer is Sokalan HP22. Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The cleaning compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The cleaning compositions of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable cleaning composition components include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

The cleaning composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid.

Pouches can be configured as single or multicompartments. It can be of any form, shape and material which is suitable for hold the composition, e.g., without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by Mono-Sol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water-soluble film. The compartment for liquid components can be different in composition than compartments containing solids: US 2009/0011970.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Granular Detergent Formulations

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238216.

The DNase may be formulated as a granule for example as a co-granule that combines one or more enzymes. Each enzyme will then be present in more granules securing a more uniform distribution of enzymes in the detergent. This also reduces the physical segregation of different enzymes due to different particle sizes. Methods for producing multi-enzyme co-granulate for the detergent industry is disclosed in the IP.com disclosure IPCOM000200739D.

Another example of formulation of enzymes by the use of co-granulates are disclosed in WO 2013/188331, which relates to a detergent composition comprising (a) a multi-enzyme co-granule; (b) less than 10 wt. % zeolite (anhydrous basis); and (c) less than 10 wt. % phosphate salt (anhydrous basis), wherein said enzyme co-granule comprises from 10 to 98 wt. % moisture sink component and the composition additionally comprises from 20 to 80 wt. % detergent moisture sink component. WO 2013/188331 also relates to a method of treating and/or cleaning a surface, preferably a fabric surface comprising the steps of (i) contacting said surface with the detergent composition as claimed and described herein in aqueous wash liquor, (ii) rinsing and/or drying the surface.

An embodiment of the invention relates to an enzyme granule/particle comprising the DNase and at least one carbohydrase and a cleaning component, wherein the carbohydrase is a cellulase, an amylase, a mannanase or a xylanase. The granule is composed of a core, and optionally one or more coatings (outer layers) surrounding the core. Typically, the granule/particle size, measured as equivalent spherical diameter (volume based average particle size), of the granule is 20-2000 μm, particularly 50-1500 μm, 100-1500 μm or 250-1200 μm. The core may include additional materials such as fillers, fibre materials (cellulose or synthetic fibres), stabilizing agents, solubilising agents, suspension agents, viscosity regulating agents, light spheres, plasticizers, salts, lubricants and fragrances. The core may include binders, such as synthetic polymer, wax, fat, or carbohydrate. The core may comprise a salt of a multivalent cation, a reducing agent, an antioxidant, a peroxide decomposing catalyst and/or an acidic buffer component, typically as a homogenous blend. The core may consist of an inert particle with the enzyme absorbed into it, or applied onto the surface, e.g., by fluid bed coating. The core may have a diameter of 20-2000 μm, particularly 50-1500 μm, 100-1500 μm or 250-1200 μm. The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in Handbook of Powder Technology; Particle size enlargement by C. E. Capes; Volume 1; 1980; Elsevier.

The core of the enzyme granule/particle may be surrounded by at least one coating, e.g., to improve the storage stability, to reduce dust formation during handling, or for coloring the granule. The optional coating(s) may include a salt coating, or other suitable coating materials, such as polyethylene glycol (PEG), methyl hydroxy-propyl cellulose (MHPC) and polyvinyl alcohol (PVA). Examples of enzyme granules with multiple coatings are shown in WO 93/07263 and WO 97/23606. The coating may be applied in an amount of at least 0.1% by weight of the core, e.g., at least 0.5%, 1% or 5%. The amount may be at most 100%, 70%, 50%, 40% or 30%. The coating is preferably at least 0.1 μm thick, particularly at least 0.5 μm, at least 1 μm or at least 5 μm. In a one embodiment, the thickness of the coating is below 100 μm. In another embodiment, the thickness of the coating is below 60 μm. In an even more particular embodiment the total thickness of the coating is below 40 μm. The coating should encapsulate the core unit by forming a substantially continuous layer. A substantially continuous layer is to be understood as a coating having few or no holes, so that the core unit it is encapsulating/enclosing has few or none uncoated areas. The layer or coating should be homogeneous in thickness. The coating can further contain other materials as known in the art, e.g., fillers, antisticking agents, pigments, dyes, plasticizers and/or binders, such as titanium dioxide, kaolin, calcium carbonate or talc. A salt coating may comprise at least 60% by weight w/w of a salt, e.g., at least 65%, at least 70%, at least 75%, at least 80%, at least 85%, at least 90%, at least 95% or at least 99% by weight w/w. The salt may be added from a salt solution where the salt is completely dissolved or from a salt suspension wherein the fine particles is less than 50 μm, such as less than 10 μm or less than 5 μm. The salt coating may comprise a single salt or a mixture of two or more salts. The salt may be water soluble, and may have a solubility at least 0.1 grams in 100 g of water at 20° C., preferably at least 0.5 g per 100 g water, e.g., at least 1 g per 100 g water, e.g., at least 5 g per 100 g water. The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used. The salt in the coating may have a constant humidity at 20° C. above 60%, particularly above 70%, above 80% or above 85%, or it may be another hydrate form of such a salt (e.g., anhydrate). The salt coating may be as described in WO 00/01793 or WO 2006/034710. Specific examples of suitable salts are NaCl ($CH_{20° C.}$=76%), $Na_2CO_3$ ($CH_{20° C.}$=92%), $NaNO_3$ ($CH_{20° C.}$=73%), $Na_2HPO_4$ ($CH_{20° C.}$=95%), $Na_3PO_4$ ($CH_{20° C.}$=92%), $NH_4Cl$ ($CH_{20° C.}$=79.5%), $(NH_4)_2HPO_4$ ($CH_{20° C.}$=93.0%), $NH_4H_2PO_4$ ($CH_{20° C.}$=93.1%), $(NH_4)_2SO_4$ ($CH_{20° C.}$=81.1%), KCl ($CH_{20° C.}$=85%), $K_2HPO_4$ ($CH_{20° C.}$=92%), $KH_2PO_4$ ($CH_{20° C.}$=96.5%), $KNO_3$ ($CH_{20° C.}$=93.5%), $Na_2SO_4$ ($CH_{20° C.}$=93%), $K_2SO_4$ ($CH_{20° C.}$=98%), $KHSO_4$ ($CH_{20° C.}$=86%), $MgSO_4$ ($CH_{20° C.}$=90%), $ZnSO_4$ ($CH_{20° C.}$=90%) and sodium citrate ($CH_{20° C.}$=86%). Other examples include $NaH_2PO_4$, $(NH_4)H_2PO_4$, $CuSO_4$, $Mg(NO_3)_2$ and magnesium acetate. The salt may be in anhydrous form, or it may be a hydrated salt, i.e., a crystalline salt hydrate with bound water(s) of crystallization, such as described in WO 99/32595. Specific examples include anhydrous sodium sulfate ($Na_2SO_4$), anhydrous magnesium sulfate ($MgSO_4$), magnesium sulfate heptahydrate ($MgSO_4.7H_2O$), zinc sulfate heptahydrate ($ZnSO_4.7H_2O$), sodium phosphate dibasic heptahydrate ($Na_2HPO_4.7H_2O$), magnesium nitrate hexahydrate ($Mg(NO_3)_2(6H_2O)$), sodium citrate dihydrate and magnesium acetate tetrahydrate. Preferably the salt is applied as a solution of the salt, e.g., using a fluid bed.

One embodiment of the present invention provides a granule, which comprises:

(a) a core comprising a DNase and a carbohydrase, wherein the carbohydrase is a cellulase, an amylase, a mannanase or a xylanase, and (b) optionally a coating consisting of one or more layer(s) surrounding the core.

One embodiment of the invention relates to a granule, which comprises:

(a) a core comprising a DNase and a cellulase, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 13, and (b) optionally a coating consisting of one or more layer(s) surrounding the core.

One embodiment of the invention relates to a granule, which comprises:

(a) a core comprising a DNase and an amylase, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 13, and (b) optionally a coating consisting of one or more layer(s) surrounding the core.

One embodiment of the invention relates to a granule, which comprises:

(a) a core comprising a DNase and a mannanase, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 13, and (b) optionally a coating consisting of one or more layer(s) surrounding the core.

One embodiment of the invention relates to a granule, which comprises:

(a) a core comprising a DNase and a xylanase, wherein the xylanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 13, and (b) optionally a coating consisting of one or more layer(s) surrounding the core.

One embodiment of the invention relates to a granule, which comprises:

(a) a core comprising a DNase and a cellulase, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 65, and (b) optionally a coating consisting of one or more layer(s) surrounding the core.

One embodiment of the invention relates to a granule, which comprises:

(a) a core comprising a DNase and an amylase, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 65, and (b) optionally a coating consisting of one or more layer(s) surrounding the core.

One embodiment of the invention relates to a granule, which comprises:

(a) a core comprising a DNase and a mannanase, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 65, and (b) optionally a coating consisting of one or more layer(s) surrounding the core.

One embodiment of the invention relates to a granule, which comprises:

(a) a core comprising a DNase and a xylanase, wherein the xylanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 65, and (b) optionally a coating consisting of one or more layer(s) surrounding the core.

One embodiment of the invention relates to a granule, which comprises:

(a) a core comprising a DNase and a cellulase, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 66, and (b) optionally a coating consisting of one or more layer(s) surrounding the core.

One embodiment of the invention relates to a granule, which comprises:

(a) a core comprising a DNase and an amylase, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 66, and (b) optionally a coating consisting of one or more layer(s) surrounding the core.

One embodiment of the invention relates to a granule, which comprises:

(a) a core comprising a DNase and a mannanase, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 66, and (b) optionally a coating consisting of one or more layer(s) surrounding the core.

One embodiment of the invention relates to a granule, which comprises:

(a) a core comprising a DNase and a xylanase, wherein the xylanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 66, and (b) optionally a coating consisting of one or more layer(s) surrounding the core.

One embodiment of the invention relates to a granule, which comprises:

(a) a core comprising a DNase and a cellulase, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 67, and (b) optionally a coating consisting of one or more layer(s) surrounding the core.

One embodiment of the invention relates to a granule, which comprises:

(a) a core comprising a DNase and an amylase, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 67, and (b) optionally a coating consisting of one or more layer(s) surrounding the core.

One embodiment of the invention relates to a granule, which comprises:

(a) a core comprising a DNase and a mannanase, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 67, and (b) optionally a coating consisting of one or more layer(s) surrounding the core.

One embodiment of the invention relates to a granule, which comprises:

(a) a core comprising a DNase and a xylanase, wherein the xylanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 67, and (b) optionally a coating consisting of one or more layer(s) surrounding the core.

One embodiment of the invention relates to a granule, which comprises:

(a) a core comprising a DNase and a cellulase, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 68, and (b) optionally a coating consisting of one or more layer(s) surrounding the core.

One embodiment of the invention relates to a granule, which comprises:

(a) a core comprising a DNase and an amylase, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 68, and (b) optionally a coating consisting of one or more layer(s) surrounding the core.

One embodiment of the invention relates to a granule, which comprises:

(a) a core comprising a DNase and a mannanase, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 68, and (b) optionally a coating consisting of one or more layer(s) surrounding the core.

One embodiment of the invention relates to a granule, which comprises:

(a) a core comprising a DNase and a xylanase, wherein the xylanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 68, and (b) optionally a coating consisting of one or more layer(s) surrounding the core.

Uses

The present invention is also directed to methods for using the compositions thereof. Laundry/textile/fabric (House hold laundry washing, Industrial laundry washing). Hard surface cleaning (ADW, car wash, Industrial surface). The compositions of the invention comprise a blend of DNase and carbohydrase, selected from a cellulase, an amylase, a mannanase or a xylanase and effectively reduce or remove organic components, such as protein and DNA from surfaces such as textiles and hard surfaces, e.g., dishes.

The compositions of the invention comprise a blend of DNase and carbohydrase, wherein the carbohydrase is a cellulase, an amylase, a mannanase or a xylanase, and effectively reduce or remove organic components, such as mannan, starch, cellulose, xyloglucan and DNA from surfaces such as textiles and hard surfaces, e.g., dishes. One embodiment of the invention relates to the use of a cleaning composition comprising a DNase, a carbohydrase, selected from a cellulase, an amylase, a mannanase or a xylanase and at least one cleaning component for reduction or removal of components of biofilm, such as DNA and at least one carbohydrase and a cleaning component, wherein the carbohydrase is a cellulase, an amylase, a mannanase or a xylanase, of an item, wherein the item is a textile or a hard surface.

One embodiment of the invention relates to the use of a cleaning composition comprising a DNase, at least one carbohydrase and a cleaning component, wherein the carbohydrase is a cellulase, an amylase, a mannanase or a xylanase for deep cleaning of an item, wherein the item is a textile or a surface.

One embodiment of the invention relates to the use of a composition comprising a DNase and a carbohydrase, wherein the carbohydrase is a cellulase, an amylase, a mannanase or a xylanase for reduction or removal of biofilm and/or compounds such as mannan, starch, cellulose, xyloglucan and DNA of an item. One embodiment of the invention relates to the use of a cleaning composition comprising a DNase and a carbohydrase, wherein the carbohydrase is a cellulase, an amylase, a mannanase or a xylanase for reduction or removal of biofilm and/or compounds such as mannan, starch, cellulose, xyloglucan and DNA of an item such as textile. One embodiment of the invention relates to the use of a cleaning composition comprising a DNase and a carbohydrase, wherein the carbohydrase is a cellulase, an amylase, a mannanase or a xylanase for deep cleaning when the cleaning composition is applied in, e.g., laundry process.

One embodiment of the invention relates to the use of a composition comprising a DNase and carbohydrase, selected from a cellulase, an amylase, a mannanase or a xylanase for reduction of redeposition or reduction of malodor. One embodiment of the invention relates to the use of a cleaning composition comprising a DNase and carbohydrase, selected from a cellulase, an amylase, a mannanase or a xylanase for reduction of redeposition or reduction of malodor.

One embodiment of the invention relates to the use of a cleaning composition comprising a DNase and carbohydrase, selected from a cellulase, an amylase, a mannanase or a xylanase for reduction of redeposition or reduction of malodor when the cleaning composition is applied in, e.g., laundry process. One embodiment of the invention relates to the use of a cleaning composition comprising a DNase and carbohydrase, selected from a cellulase, an amylase, a mannanase or a xylanase for reduction of redeposition or reduction of malodor on an item, e.g., textile. In one embodiment, the composition is an anti-redeposition composition.

One embodiment of the invention relates to the use of a cleaning composition comprising a DNase and a cellulase for deep cleaning of an item or reduction of redeposition or malodor, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86.

One embodiment of the invention relates to the use of a cleaning composition comprising a DNase and an amylase for deep cleaning of an item or reduction of redeposition or malodor, wherein the amylase selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91.

One embodiment of the invention relates to the use of a cleaning composition comprising a DNase and a mannanase for deep cleaning of an item or reduction of redeposition or malodor, wherein the mannanase selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82.

One embodiment of the invention relates to the use of a cleaning composition comprising a DNase and a xylanase for deep cleaning of an item or reduction of redeposition or malodor, wherein the xylanase selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82.

One embodiment of the invention relates to the use of a cleaning composition comprising a DNase and cellulase for deep cleaning of an item or reduction of redeposition or malodor, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 13.

One embodiment of the invention relates to the use of a cleaning composition comprising a DNase and cellulase for deep cleaning of an item or reduction of redeposition or malodor, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 65.

One embodiment of the invention relates to the use of a cleaning composition comprising a DNase and cellulase for deep cleaning of an item or reduction of redeposition or malodor, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 66.

One embodiment of the invention relates to the use of a cleaning composition comprising a DNase and cellulase for deep cleaning of an item or reduction of redeposition or malodor, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 67.

One embodiment of the invention relates to the use of a cleaning composition comprising a DNase and cellulase for deep cleaning of an item or reduction of redeposition or malodor, wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 68.

One embodiment of the invention relates to the use of a cleaning composition comprising a DNase and amylase for deep cleaning of an item or reduction of redeposition or malodor, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 13.

One embodiment of the invention relates to the use of a cleaning composition comprising a DNase and amylase for deep cleaning of an item or reduction of redeposition or malodor, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 65.

One embodiment of the invention relates to the use of a cleaning composition comprising a DNase and amylase for deep cleaning of an item or reduction of redeposition or malodor, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 66.

One embodiment of the invention relates to the use of a cleaning composition comprising a DNase and amylase for deep cleaning of an item or reduction of redeposition or malodor, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 67.

One embodiment of the invention relates to the use of a cleaning composition comprising a DNase and amylase for deep cleaning of an item or reduction of redeposition or malodor, wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 68.

One embodiment of the invention relates to the use of a cleaning composition comprising a DNase and mannanase for deep cleaning of an item or reduction of redeposition or malodor, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 13.

One embodiment of the invention relates to the use of a cleaning composition comprising a DNase and mannanase for deep cleaning of an item or reduction of redeposition or malodor, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 65.

One embodiment of the invention relates to the use of a cleaning composition comprising a DNase and mannanase for deep cleaning of an item or reduction of redeposition or malodor, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 66.

One embodiment of the invention relates to the use of a cleaning composition comprising a DNase and mannanase for deep cleaning of an item or reduction of redeposition or malodor, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 67.

One embodiment of the invention relates to the use of a cleaning composition comprising a DNase and mannanase for deep cleaning of an item or reduction of redeposition or malodor, wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 68.

One embodiment of the invention relates to the use of a cleaning composition comprising a DNase and xylanase for deep cleaning of an item or reduction of redeposition or malodor, wherein the xylanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 13.

One embodiment of the invention relates to the use of a cleaning composition comprising a DNase and xylanase for deep cleaning of an item or reduction of redeposition or malodor, wherein the xylanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 65.

One embodiment of the invention relates to the use of a cleaning composition comprising a DNase and xylanase for deep cleaning of an item or reduction of redeposition or malodor, wherein the xylanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 66.

One embodiment of the invention relates to the use of a cleaning composition comprising a DNase and xylanase for deep cleaning of an item or reduction of redeposition or malodor, wherein the xylanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 67.

One embodiment of the invention relates to the use of a cleaning composition comprising a DNase and xylanase for deep cleaning of an item or reduction of redeposition or malodor, wherein the xylanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 68.

The invention further relates to a method of deep cleaning of an item, wherein the item may be textile or hard surface preferably is a textile.

One embodiment of the invention relates to a method of deep cleaning on an item, comprising the steps of:
a) contacting the item with a cleaning composition according to the invention; and
b) optionally rinsing the item, wherein the item is preferably a textile.

One embodiment of the invention relates to a method of deep cleaning on an item, comprising the steps of:
a) contacting the item with a solution comprising an enzyme mixture comprising a DNase, a carbohydrase, wherein the carbohydrase is a cellulase, an amylase, a mannanase or a xylanase; and a cleaning component, wherein the cleaning component is selected from 0.1 to 50 wt. % of at least one a surfactant; 0.5 to 30 wt. % of at least one builder; and 0.01 to 20 wt. % of at least one bleach component; and
b) optionally rinsing the item, wherein the item is preferably a textile.

One embodiment of the invention relates to a method of deep cleaning on an item, comprising the steps of:
a) contacting the item with a solution comprising an enzyme mixture comprising a DNase, a cellulase; and a cleaning component, wherein the cleaning component is selected from 0.1 to 50 wt. % of at least one a surfactant; 0.5 to 30 wt. % of at least one builder; and 0.01 to 20 wt. % of at least one bleach component; and
b) optionally rinsing the item, wherein the item is preferably a textile;

wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86.

One embodiment of the invention relates to a method of deep cleaning on an item, comprising the steps of:
a) contacting the item with a solution comprising an enzyme mixture comprising a DNase, an amylase; and a cleaning component, wherein the cleaning component is selected from 0.1 to 50 wt. % of at least one a surfactant; 0.5 to 30 wt. % of at least one builder; and 0.01 to 20 wt. % of at least one bleach component; and
b) optionally rinsing the item, wherein the item is preferably a textile;
wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91.

One embodiment of the invention relates to a method of deep cleaning on an item, comprising the steps of:
a) contacting the item with a solution comprising an enzyme mixture comprising a DNase, mannanase; and a cleaning component, wherein the cleaning component is selected from 0.1 to 50 wt. % of at least one a surfactant; 0.5 to 30 wt. % of at least one builder; and 0.01 to 20 wt. % of at least one bleach component; and
b) optionally rinsing the item, wherein the item is preferably a textile;
wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82.

One embodiment of the invention relates to a method of deep cleaning on an item, comprising the steps of:
a) contacting the item with a solution comprising an enzyme mixture comprising a DNase, xylanase; and a cleaning component, wherein the cleaning component is selected from 0.1 to 50 wt. % of at least one a surfactant; 0.5 to 30 wt. % of at least one builder; and 0.01 to 20 wt. % of at least one bleach component; and
b) optionally rinsing the item, wherein the item is preferably a textile;

wherein the xylanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87.

One embodiment of the invention relates to a method of deep cleaning on an item, comprising the steps of:

a) contacting the item with a solution comprising an enzyme mixture comprising a DNase, a cellulase; and a cleaning component, wherein the cleaning component is selected from 0.1 to 50 wt. % of at least one a surfactant; 0.5 to 30 wt. % of at least one builder; and 0.01 to 20 wt. % of at least one bleach component; and b) optionally rinsing the item, wherein the item is preferably a textile;

wherein the cellulase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 83, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 85, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 86 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 13, SEQ ID NO 65, SEQ ID NO 66, SEQ ID NO 67 or SEQ ID NO 68.

One embodiment of the invention relates to a method of deep cleaning on an item, comprising the steps of:

a) contacting the item with a solution comprising an enzyme mixture comprising a DNase, an amylase; and a cleaning component, wherein the cleaning component is selected from 0.1 to 50 wt. % of at least one a surfactant; 0.5 to 30 wt. % of at least one builder; and 0.01 to 20 wt. % of at least one bleach component; and b) optionally rinsing the item, wherein the item is preferably a textile;

wherein the amylase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98% or 100% sequence identity to the polypeptide shown in SEQ ID NO: 90, and a polypeptide having at least 60%, at least 65%, at least 70%, at least 75%, at least 80%, at least 85%, at least 90%, at least 95%, at least 98% or 100% sequence identity to the polypeptide shown in SEQ ID NO: 91 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 13, SEQ ID NO 65, SEQ ID NO 66, SEQ ID NO 67 or SEQ ID NO 68.

One embodiment of the invention relates to a method of deep cleaning on an item, comprising the steps of:

a) contacting the item with a solution comprising an enzyme mixture comprising a DNase, mannanase; and a cleaning component, wherein the cleaning component is selected from 0.1 to 50 wt. % of at least one a surfactant; 0.5 to 30 wt. % of at least one builder; and 0.01 to 20 wt. % of at least one bleach component; and b) optionally rinsing the item, wherein the item is preferably a textile;

wherein the mannanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 82 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 13, SEQ ID NO 65, SEQ ID NO 66, SEQ ID NO 67 or SEQ ID NO 68.

One embodiment of the invention relates to a method of deep cleaning on an item, comprising the steps of:

a) contacting the item with a solution comprising an enzyme mixture comprising a DNase, xylanase; and a cleaning component, wherein the cleaning component is selected from 0.1 to 50 wt. % of at least one a surfactant; 0.5 to 30 wt. % of at least one builder; and 0.01 to 20 wt. % of at least one bleach component; and b) optionally rinsing the item, wherein the item is preferably a textile;

wherein the xylanase is selected from a polypeptide having at least 60%, at least 65%, at least 70%, at least 75%, at least 80%, at least 85%, at least 90%, at least 95%, at least 98% or 100% sequence identity to the polypeptide shown in SEQ ID NO: 87 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 13, SEQ ID NO 65, SEQ ID NO 66, SEQ ID NO 67 or SEQ ID NO 68.

The invention is further described in the following paragraphs

Paragraph 1 A cleaning composition comprising at least 0.001 ppm DNase and at least 0.001 ppm carbohydrase and a cleaning component, wherein the cleaning component is selected from a. 0.1 to 15 wt. % of at least one a surfactant;
   b. 0.5 to 20 wt. % of at least one builder; and
   c. 0.01 to 10 wt. % of at least one bleach component.

Paragraph 2. The cleaning composition according to paragraph 1, wherein the DNase comprises one or both of the motif(s) [D/M/L][S/T]GYSR[D/N] (SEQ ID NO: 73), ASXNRSKG (SEQ ID NO: 74) and the carbohydrase is a cellulase.

Paragraph 3. The cleaning composition according to paragraph 1, wherein the DNase comprises one or both of the motif(s) [D/M/L][S/T]GYSR[D/N] (SEQ ID NO: 73), ASXNRSKG (SEQ ID NO: 74) and the carbohydrase is a mannanase.

Paragraph 4. The cleaning composition according to paragraph 1, wherein the DNase comprises one or both of the motif(s) [D/M/L][S/T]GYSR[D/N] (SEQ ID NO: 73), ASXNRSKG (SEQ ID NO: 74) and the carbohydrase is a amylase.

Paragraph 5. The cleaning composition according to any of paragraphs 1 to 4, wherein the DNase is selected from the group of polypeptides:

a) a polypeptide having at least 80% sequence identity to the polypeptide shown in SEQ ID NO: 1,
b) a polypeptide having at least 80% sequence identity to the polypeptide shown in SEQ ID NO: 2,
c) a polypeptide having at least 80% sequence identity to the polypeptide shown in SEQ ID NO: 3,
d) a polypeptide having at least 80% sequence identity to the polypeptide shown in SEQ ID NO: 4,
e) a polypeptide having at least 80% sequence identity to the polypeptide shown in SEQ ID NO: 5,
f) a polypeptide having at least 80% sequence identity to the polypeptide shown in SEQ ID NO: 6,
g) a polypeptide having at least 80% sequence identity to the polypeptide shown in SEQ ID NO: 7,
h) a polypeptide having at least 80% sequence identity to the polypeptide shown in SEQ ID NO: 8,
i) a polypeptide having at least 80% sequence identity to the polypeptide shown in SEQ ID NO: 9,
j) a polypeptide having at least 80% sequence identity to the polypeptide shown in SEQ ID NO: 10,
k) a polypeptide having at least 80% sequence identity to the polypeptide shown in SEQ ID NO: 11,
l) a polypeptide having at least 80% sequence identity to the polypeptide shown in SEQ ID NO: 12,
m) a polypeptide having at least 80% sequence identity to the polypeptide shown in SEQ ID NO: 13,
n) a polypeptide having at least 80% sequence identity to the polypeptide shown in SEQ ID NO: 14,
o) a polypeptide having at least 80% sequence identity to the polypeptide shown in SEQ ID NO: 15,
p) a polypeptide having at least 80% sequence identity to the polypeptide shown in SEQ ID NO: 16,
q) a polypeptide having at least 80% sequence identity to the polypeptide shown in SEQ ID NO: 17,
r) a polypeptide having at least 80% sequence identity to the polypeptide shown in SEQ ID NO: 18,
s) a polypeptide having at least 80% sequence identity to the polypeptide shown in SEQ ID NO: 19,
t) a polypeptide having at least 80% sequence identity to the polypeptide shown in SEQ ID NO: 20,
u) a polypeptide having at least 80% sequence identity to the polypeptide shown in SEQ ID NO: 21,
v) a polypeptide having at least 80% sequence identity to the polypeptide shown in SEQ ID NO: 22,
w) a polypeptide having at least 80% sequence identity to the polypeptide shown in SEQ ID NO: 23,
x) a polypeptide having at least 80% sequence identity to the polypeptide shown in SEQ ID NO: 24, and
y) a polypeptide having at least 80% sequence identity to the polypeptide shown in SEQ ID NO: 25, and wherein the carbohydrase is selected from the group consisting of:
  i. a cellulase selected from a polypeptide having at least 80% sequence identity to the polypeptide shown in SEQ ID NO: 83, a polypeptide having at least 80% sequence identity to the polypeptide shown in SEQ ID NO: 84, a polypeptide having at least 80% sequence identity to the polypeptide shown in SEQ ID NO: 85, and a polypeptide having at least 80% sequence identity to the polypeptide shown in SEQ ID NO: 86;
  ii. a xylanase selected from a polypeptide having at least 80% sequence identity to the polypeptide shown in SEQ ID NO: 87;
  iii. a mannanase selected from a polypeptide having at least 80% sequence identity to the polypeptide shown in SEQ ID NO: 82; and
  iv. an amylase selected from a polypeptide having at least 80% sequence identity to the polypeptide shown in SEQ ID NO: 88, a polypeptide having at least 80% sequence identity to the polypeptide shown in SEQ ID NO: 89, a polypeptide having at least 80% sequence identity to the polypeptide shown in SEQ ID NO: 90, and a polypeptide having at least 80% sequence identity to the polypeptide shown in SEQ ID NO: 91.

Paragraph 6. The cleaning composition according to paragraph 1 wherein the DNase comprises one or both of the motifs [V/I]PL[S/A]NAWK (SEQ ID NO: 75) or NPQL (SEQ ID NO: 76) and the carbohydrase is a cellulase.

Paragraph 7. The cleaning composition according to paragraph 1 wherein the DNase comprises one or both of the motifs [V/I]PL[S/A]NAWK (SEQ ID NO: 75) or NPQL (SEQ ID NO: 76) and the carbohydrase is a mannanase.

Paragraph 8. The cleaning composition according to paragraph 1 wherein the DNase comprise one or both of the motifs [V/I]PL[S/A]NAWK (SEQ ID NO: 75) or NPQL (SEQ ID NO: 76) and the carbohydrase is a amylase.

Paragraph 9. The cleaning composition according to any of paragraphs 1 and 6 to 8, wherein the DNase is selected from the group of polypeptides:
a) a polypeptide having at least 80% sequence identity to the polypeptide shown in SEQ ID NO: 26,
b) a polypeptide having at least 80% sequence identity to the polypeptide shown in SEQ ID NO: 27,
c) a polypeptide having at least 80% sequence identity to the polypeptide shown in SEQ ID NO: 28,
d) a polypeptide having at least 80% sequence identity to the polypeptide shown in SEQ ID NO: 29,
e) a polypeptide having at least 80% sequence identity to the polypeptide shown in SEQ ID NO: 30,
f) a polypeptide having at least 80% sequence identity to the polypeptide shown in SEQ ID NO: 31,
g) a polypeptide having at least 80% sequence identity to the polypeptide shown in SEQ ID NO: 32,
h) a polypeptide having at least 80% sequence identity to the polypeptide shown in SEQ ID NO: 33,
i) a polypeptide having at least 80% sequence identity to the polypeptide shown in SEQ ID NO: 34,
j) a polypeptide having at least 80% sequence identity to the polypeptide shown in SEQ ID NO: 35,
k) a polypeptide having at least 80% sequence identity to the polypeptide shown in SEQ ID NO: 36,
l) a polypeptide having at least 80% sequence identity to the polypeptide shown in SEQ ID NO: 37,
m) a polypeptide having at least 80% sequence identity to the polypeptide shown in SEQ ID NO: 38, and wherein the carbohydrase is selected from the group consisting of:
  i. a cellulase selected from a polypeptide having at least 80% sequence identity to the polypeptide shown in SEQ ID NO: 83, a polypeptide having at least 80% sequence identity to the polypeptide shown in SEQ ID NO: 84, a polypeptide having at least 80% sequence identity to the polypeptide shown in SEQ ID NO: 85, and a polypeptide having at least 80% sequence identity to the polypeptide shown in SEQ ID NO: 86;
  ii. a xylanase selected from a polypeptide having at least 80% sequence identity to the polypeptide shown in SEQ ID NO: 87;
  iii. a mannanase selected from a polypeptide having at least 80% sequence identity to the polypeptide shown in SEQ ID NO: 82; and
  iv. an amylase selected from a polypeptide having at least 80% sequence identity to the polypeptide shown in SEQ ID NO: 88, a polypeptide having at least 80% sequence identity to the polypeptide shown in SEQ ID NO: 89, a polypeptide having at least 80% sequence identity to the polypeptide shown in SEQ ID NO: 90, and a polypeptide having at least 80% sequence identity to the polypeptide shown in SEQ ID NO: 91.

Paragraph 10. The cleaning composition according to paragraph 1 wherein the DNase comprises one or both of the motifs P[Q/E]L[W/Y] (SEQ ID NO: 77) or [K/H/E]NAW (SEQ ID NO: 78) and the carbohydrase is a cellulase.

Paragraph 11. The cleaning composition according to paragraph 1 wherein the DNase comprise one or both of the motifs P[Q/E]L[W/Y] (SEQ ID NO: 77) or [K/H/E]NAW (SEQ ID NO: 78) and the carbohydrase is a mannanase.

Paragraph 12. The cleaning composition according to paragraph 1 wherein the DNase comprise one or both of the motifs P[Q/E]L[W/Y] (SEQ ID NO: 77) or [K/H/E]NAW (SEQ ID NO: 78) and the carbohydrase is an amylase.

Paragraph 13. The cleaning composition according to paragraph 1 or 10 to 12, wherein the DNase is selected from the group of polypeptides:
  a) a polypeptide having at least 80% sequence identity to the polypeptide shown in SEQ ID NO: 39,
  b) a polypeptide having at least 80% sequence identity to the polypeptide shown in SEQ ID NO: 40,
  c) a polypeptide having at least 80% sequence identity to the polypeptide shown in
  SEQ ID NO: 41,
  d) a polypeptide having at least 80% sequence identity to the polypeptide shown in SEQ ID NO: 42,
  e) a polypeptide having at least 80% sequence identity to the polypeptide shown in SEQ ID NO: 43
  f) a polypeptide having at least 80% sequence identity to the polypeptide shown in SEQ ID NO: 44,
  g) a polypeptide having at least 80% sequence identity to the polypeptide shown in SEQ ID NO: 45,
  h) a polypeptide having at least 80% sequence identity to the polypeptide shown in SEQ ID NO: 46,
  i) a polypeptide having at least 80% sequence identity to the polypeptide shown in SEQ ID NO: 47,
  j) a polypeptide having at least 80% sequence identity to the polypeptide shown in SEQ ID NO: 48,
  k) a polypeptide having at least 80% sequence identity to the polypeptide shown in SEQ ID NO: 49,
  l) a polypeptide having at least 80% sequence identity to the polypeptide shown in SEQ ID NO: 50,
  m) a polypeptide having at least 80% sequence identity to the polypeptide shown in SEQ ID NO: 51, and wherein the carbohydrase is selected from the group consisting of;
    i. a cellulase selected from a polypeptide having at least 80% sequence identity to the polypeptide shown in SEQ ID NO: 83, a polypeptide having at least 80% sequence identity to the polypeptide shown in SEQ ID NO: 84, a polypeptide having at least 80% sequence identity to the polypeptide shown in SEQ ID NO: 85, and a polypeptide having at least 80% sequence identity to the polypeptide shown in SEQ ID NO: 86;
    ii. a xylanase selected from a polypeptide having at least 80% sequence identity to the polypeptide shown in SEQ ID NO: 87;
    iii. a mannanase selected from a polypeptide having at least 80% sequence identity to the polypeptide shown in SEQ ID NO: 82; and
    iv. an amylase selected from a polypeptide having at least 80% sequence identity to the polypeptide shown in SEQ ID NO: 88, a polypeptide having at least 80% sequence identity to the polypeptide shown in SEQ ID NO: 89, a polypeptide having at least 80% sequence identity to the polypeptide shown in SEQ ID NO: 90, and a polypeptide having at least 80% sequence identity to the polypeptide shown in SEQ ID NO: 91.

Paragraph 14. The cleaning composition according to paragraph 1 wherein the DNase is selected from the group consisting of:
  a) polypeptide obtainable from *Bacillus licheniformis* having a sequence identity to the polypeptide shown in SEQ ID NO: 65 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity,
  b) polypeptide obtainable from *Bacillus subtilis* having a sequence identity to the polypeptide shown in SEQ ID NO: 66 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity,
  c) polypeptide obtainable from *Aspergillus oryzae* having a sequence identity to the polypeptide shown in SEQ ID NO: 67 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity,
  d) polypeptide obtainable from *Trichoderma harzianum* having a sequence identity to the polypeptide shown in SEQ ID NO: 68 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity, and wherein the carbohydrase is selected from the group consisting of;
    i. a cellulase selected from a polypeptide having at least 80% sequence identity to the polypeptide shown in SEQ ID NO: 83, a polypeptide having at least 80% sequence identity to the polypeptide shown in SEQ ID NO: 84, a polypeptide having at least 80% sequence identity to the polypeptide shown in SEQ ID NO: 85, and a polypeptide having at least 80% sequence identity to the polypeptide shown in SEQ ID NO: 86;
    ii. a xylanase selected from a polypeptide having at least 80% sequence identity to the polypeptide shown in SEQ ID NO: 87;
    iii. a mannanase selected from a polypeptide having at least 80% sequence identity to the polypeptide shown in SEQ ID NO: 82; and
    iv. an amylase selected from a polypeptide having at least 80% sequence identity to the polypeptide shown in SEQ ID NO: 88, a polypeptide having at least 80% sequence identity to the polypeptide shown in SEQ ID NO: 89, a polypeptide having at least 80% sequence identity to the polypeptide shown in SEQ ID NO: 90, and a polypeptide having at least 80% sequence identity to the polypeptide shown in SEQ ID NO: 91.

Paragraph 15. The use of a composition according to any of the previous paragraphs for deep cleaning of an item, wherein the item is a textile or a surface.

Paragraph 16. A method of formulating a cleaning composition comprising adding a DNase, a carbohydrase and at least one cleaning component.

Paragraph 17. A kit intended for deep cleaning, wherein the kit comprises a solution of an enzyme mixture comprising a DNase, carbohydrase and optionally a protease.

Paragraph 18. A method of deep cleaning on an item, comprising the steps of:
  a) contacting the item with a solution comprising an enzyme mixture comprising a DNase and a carbohydrase and optionally a protease; and a cleaning component, wherein the cleaning component is selected from 0.1 to 15 wt. % of at least one a surfactant; 0.5 to 20 wt. % of at least one builder; and 0.01 to 10 wt. % of at least one bleach component; and b) optionally rinsing the item, wherein the item is preferably a textile.

Definitions

Biofilm is produced by any group of microorganisms in which cells stick to each other or stick to a surface, such as a textile, dishware or hard surface or another kind of surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium. Bacteria living in a biofilm usually have significantly different properties from planktonic bacteria of the same species, as the dense and protected environment of the film allows them to cooperate and interact in various ways. One benefit of this environment for the microorganisms is increased resistance to detergents and antibiotics, as the dense extracellular matrix and the outer layer of cells protect the interior of the community.

On laundry biofilm producing bacteria can be found among the following species: *Acinetobacter* sp., *Aeromicrobium* sp., *Brevundimonas* sp., *Microbacterium* sp., *Micrococcus luteus, Pseudomonas* sp., *Staphylococcus epidermidis,* and *Stenotrophomonas* sp. On hard surfaces biofilm producing bacteria can be found among the following species: *Acinetobacter* sp., *Aeromicrobium* sp., *Brevundimonas* sp., *Microbacterium* sp., *Micrococcus luteus, Pseudomonas* sp., *Staphylococcus epidermidis, Staphylococcus aureus* and *Stenotrophomonas* sp. In one aspect, the biofilm producing strain is *Brevundimonas* sp. In one aspect, the biofilm producing strain is *Pseudomonas alcaliphila* or *Pseudomonas fluorescens*. In one aspect, the biofilm producing strain is *Staphylococcus aureus*.

By the term "deep cleaning" is meant reduction, disruption or removal of components of organic matter, e.g., biofilm, such as polysaccharides, proteins, DNA, soil or other components present in the organic matter.

Cleaning component: The cleaning component, e.g., the detergent adjunct ingredient is different to the DNase and carbohydrase. The precise nature of these additional cleaning components, e.g., adjunct components, and levels of incorporation thereof, will depend on the physical form of the composition and the nature of the operation for which it is to be used. Suitable cleaning components, e.g., adjunct materials include, but are not limited to the components described below such as surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, and/or pigments.

Cleaning Composition: The term "cleaning composition" refers to compositions that find use in the removal of undesired compounds from items to be cleaned, such as textiles. The detergent composition may be used to, e.g., clean textiles for both household cleaning and industrial cleaning. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; fabric fresheners; fabric softeners; and textile and laundry prespotters/pretreatment). In addition to containing the enzyme blend of the invention, the detergent formulation may contain one or more additional enzymes (such as proteases, lipases, cutinases, endoglucanases, xyloglucanases, pectinases, pectin lyases, xanthanases, peroxidases, haloperoxygenases and catalases or any mixture thereof), and/or detergent adjunct ingredients such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

The term "enzyme detergency benefit" is defined herein as the advantageous effect an enzyme may add to a detergent compared to the same detergent without the enzyme. Important detergency benefits which can be provided by enzymes are stain removal with no or very little visible soils after washing and/or cleaning, prevention or reduction of redeposition of soils released in the washing process (an effect that also is termed anti-redeposition), restoring fully or partly the whiteness of textiles which originally were white but after repeated use and wash have obtained a greyish or yellowish appearance (an effect that also is termed whitening). Textile care benefits, which are not directly related to catalytic stain removal or prevention of redeposition of soils, are also important for enzyme detergency benefits. Examples of such textile care benefits are prevention or reduction of dye transfer from one fabric to another fabric or another part of the same fabric (an effect that is also termed dye transfer inhibition or anti-backstaining), removal of protruding or broken fibers from a fabric surface to decrease pilling tendencies or remove already existing pills or fuzz (an effect that also is termed anti-pilling), improvement of the fabric-softness, colour clarification of the fabric and removal of particulate soils which are trapped in the fibers of the fabric or garment. Enzymatic bleaching is a further enzyme detergency benefit where the catalytic activity generally is used to catalyze the formation of bleaching components such as hydrogen peroxide or other peroxides. Textile care benefits, which are not directly related to catalytic stain removal or prevention of redeposition of soils, are also important for enzyme detergency benefits. Examples of such textile care benefits are prevention or reduction of dye transfer from one textile to another textile or another part of the same textile (an effect that is also termed dye transfer inhibition or anti-backstaining), removal of protruding or broken fibers from a textile surface to decrease pilling tendencies or remove already existing pills or fuzz (an effect that also is termed anti-pilling), improvement of the textile-softness, colour clarification of the textile and removal of particulate soils which are trapped in the fibers of the textile. Enzymatic bleaching is a further enzyme detergency benefit where the catalytic activity generally is used to catalyze the formation of bleaching component such as hydrogen peroxide or other peroxides or other bleaching species."

The term "hard surface cleaning" is defined herein as cleaning of hard surfaces wherein hard surfaces may include floors, tables, walls, roofs etc. as well as surfaces of hard objects such as cars (car wash) and dishes (dish wash). Dish washing includes but are not limited to cleaning of plates, cups, glasses, bowls, cutlery such as spoons, knives, forks, serving utensils, ceramics, plastics, metals, china, glass and acrylics.

The term "wash performance" is used as an enzyme's ability to remove stains present on the object to be cleaned during, e.g., wash or hard surface cleaning.

The term "whiteness" is defined herein as a greying, yellowing of a textile. Loss of whiteness may be due to removal of optical brighteners/hueing agents. Greying and yellowing can be due to soil redeposition, body soils, coloring from, e.g., iron and copper ions or dye transfer. Whiteness might include one or several issues from the list below: colourant or dye effects; incomplete stain removal (e.g., body soils, sebum etc.); redeposition (greying, yellowing or other discolourations of the object) (removed soils reassociate with other parts of textile, soiled or unsoiled); chemical changes in textile during application; and clarification or brightening of colors.

The term "laundering" relates to both household laundering and industrial laundering and means the process of treating textiles with a solution containing a cleaning or detergent composition of the present invention. The laundering process can for example be carried out using, e.g., a household or an industrial washing machine or can be carried out by hand.

The term "malodor" means an odor which is not desired on clean items. The cleaned item should smell fresh and clean without malodors adhered to the item. One example of malodor is compounds with an unpleasant smell, which may be produced by microorganisms. Another example is unpleasant smells can be sweat or body odor adhered to an item which has been in contact with human or animal. Another example of malodor can be the odor from spices, which sticks to items for example curry or other exotic spices which smells strongly.

The term "mature polypeptide" means a polypeptide in its final form following translation and any post-translational modifications, such as N-terminal processing, C-terminal truncation, glycosylation, phosphorylation, etc.

The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and towelling. The textile may be cellulose based such as natural cellulosics, including cotton, flax/linen, jute, ramie, sisal or coir or manmade cellulosics (e.g., originating from wood pulp) including viscose/rayon, cellulose acetate fibers (tricell), lyocell or blends thereof. The textile or fabric may also be non-cellulose based such as natural polyamides including wool, camel, cashmere, mohair, rabbit and silk or synthetic polymers such as nylon, aramid, polyester, acrylic, polypropylene and spandex/elastane, or blends thereof as well as blends of cellulose based and non-cellulose based fibers. Examples of blends are blends of cotton and/or rayon/viscose with one or more companion material such as wool, synthetic fiber (e.g., polyamide fiber, acrylic fiber, polyester fiber, polyvinyl chloride fiber, polyurethane fiber, polyurea fiber, aramid fiber), and/or cellulose-containing fiber (e.g., rayon/viscose, ramie, flax/linen, jute, cellulose acetate fiber, lyocell). Fabric may be conventional washable laundry, for example stained household laundry. When the term fabric or garment is used it is intended to include the broader term textiles as well.

The term "variant" means a polypeptide having the activity of the parent or precursor polypeptide and comprising an alteration, i.e., a substitution, insertion, and/or deletion, at one or more (e.g., several) positions compared to the precursor or parent polypeptide. A substitution means replacement of the amino acid occupying a position with a different amino acid; a deletion means removal of the amino acid occupying a position; and an insertion means adding an amino acid adjacent to and immediately following the amino acid occupying a position.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 6.6.0 or later. The parameters used are a gap open penalty of 10, a gap extension penalty of 0.5, and the EBLOSUM62 (EMBOSS version of BLOSUM62) substitution matrix. The output of Needle labeled "longest identity" (obtained using the-nobrief option) is used as the percent identity and is calculated as follows:

$$(\text{Identical Residues} \times 100)/(\text{Length of Alignment Total Number of Gaps in Alignment})$$

EXAMPLES

Assays
Assay I: Testing of DNase Activity

DNase activity was determined on DNase Test Agar with Methyl Green (BD, Franklin Lakes, N.J., USA), which was prepared according to the manual from supplier. Briefly, 21 g of agar was dissolved in 500 ml water and then autoclaved for 15 min at 121° C. Autoclaved agar was temperated to 48° C. in water bath, and 20 ml of agar was poured into petri dishes with and allowed to solidify by incubation o/n at room temperature. On solidified agar plates, 5 µl of enzyme solutions are added and DNase activity is observed as colorless zones around the spotted enzyme solutions.

Assay II: Testing of Mannanase Activity

Mannanase activity may be tested according to standard test procedures known in the art, such as by applying a solution to be tested to 4 mm diameter holes punched out in agar plates containing 0.2% AZCL galactomannan (carob), i.e., substrate for the assay of endo-1,4-beta-D-mannanase available as CatNo.I-AZGMA from the company Megazyme (Megazyme's Internet address: http://www.megazyme.com/Purchase/index.html).

Assay III: Testing of Xyloglucanase Activity

The reaction involves endo hydrolysis of 1,4-beta-D-glucosidic linkages in xyloglucan. For purposes of the present invention, xyloglucanase activity is determined using AZCL-xyloglucan (from Megazyme) as the reaction substrate. The assay can be performed in several ways, e.g., as described in Example 2 of the present application or as described in WO 01/62903. One unit of xyloglucanase activity (XyloU) is defined by reference to the assay method described in WO 01/62903, page 60, lines 3-17.

Assay IV: Testing of Cellulase Activity

The term "cellulase activity" is defined herein as an enzyme catalyzed hydrolysis of 1,4-beta-D-glucosidic linkages in beta-1,4-glucan (cellulose). For purposes of the present invention, cellulase activity is determined using AZCL-HE-cellulose (from Megazyme) as the reaction substrate.

Example 1

Isolating Laundry Specific Bacterial Strains

One strain of Brevundimonas sp. isolated from laundry was used in the present example. The Brevundimonas sp. was isolated during a study, where the bacterial diversity in laundry after washing at 15, 40 and 60° C., respectively, was investigated. The study was conducted on laundry collected from Danish households. For each wash, 20 g of laundry items (tea towel, towel, dish cloth, bib, T-shirt armpit, T-shirt collar, socks) in the range 4:3:2:2:1:1:1 was used. Washing was performed in a Laundr-O-Meter (LOM) at 15, 40 or 60° C. For washing at 15 and 40° C., Ariel Sensitive White & Color was used, whereas WFK IEC-A* model detergent was used for washing at 60° C. Ariel Sensitive White & Color was prepared by weighing out 5.1 g and adding tap water up to 1000 ml followed by stirring for 5 minutes. WFK IEC-A model detergent (which is available from WFK Testgewebe GmbH) was prepared by weighing out 5 g and adding tap water up to 1300 ml followed by stirring for 15 min. Washing was performed for 1 hour at 15, 40 and 60° C., respectively, followed by 2 times rinsing with tap water for 20 min at 15° C. Laundry was sampled immediately after washing at 15, 40 and 60° C., respectively. Twenty grams of laundry was added 0.9% (w/v) NaCl (1.06404; Merck, Darmstadt, Germany) with 0.5% (w/w) tween 80 to yield a 1:10 dilution in stomacher bag. The mixture was homogenized using a Stomacher for 2 minutes at medium speed. After homogenization, ten-fold dilutions were prepared in 0.9% (w/v) NaCl. Bacteria were enumerated on Tryptone Soya Agar (TSA) (CM0129, Oxoid, Basingstoke, Hampshire, UK) incubated aerobically at 30° C. for 5-7 days. To suppress growth of yeast and moulds, 0.2% sorbic acid (359769, Sigma) and 0.1% cycloheximide (18079; Sigma) were added. Bacterial colonies were selected from countable plates and purified by restreaking twice on TSA. For long time storage, purified isolates were stored at −80° C. in TSB containing 20% (w/v) glycerol (49779; Sigma).

Preparation of Swatches with Biofilm

Swatches with biofilm of Brevundimonas sp. was included in the present study. Bacteria was pre-grown on Tryptone Soya Agar (TSA) (pH 7.3) (CM0131; Oxoid Ltd, Basingstoke, UK) for 2-5 days at 30° C. From a single colony, a loop-full was transferred to 10 mL of TSB and incubated for 1 day at 30° C. with shaking (240 rpm). After propagation, cells were pelleted by centrifugation (Sigma Laboratory Centrifuge 6K15) (3000 g at 21° C. in 7 min) and resuspended in 10 mL of TSB diluted twice with water. Optical density (OD) at 600 nm was measured using a spectophometer (POLARstar Omega (BMG Labtech, Ortenberg, Germany). Fresh TSB diluted twice with water was inoculated to an OD600 nm of 0.03, and 50 mL was added into a petridish (diameter 125 mm), in which a swatch (80 mm×120 mm) of sterile cotton (WFK10A). After incubation (48 h at 15° C. with shaking (100 rpm), swatches were rinsed twice with 0.9% (w/v) NaCl and dried in LAF bench for 60 min. Swatches were stored at 4° C. prior to wash.

Example 2

Wash Experiment

Wash experiment was performed using the Automatic Mechanical Stress Assay (AMSA). With AMSA, the wash performance of many small volume enzyme-detergent solutions can be examined at the same time. The AMSA plate has many slots for test solutions, and a lid that firmly squeezes the textile to be washed against the slot openings. During the wash, the plate, test solutions, textile and lid are vigorously shaken to bring the test solution in contact with the textile and apply mechanical stress in a regular, periodic, oscillating manner.

The wash experiment was conducted under the experimental conditions specified below:

| | |
|---|---|
| Detergent dosage | 3.3 g/L (liquid detergent) |
| Test solution volume | 160 micro L |
| pH | pH 8 |
| Wash time | 20 minutes |
| Temperature | 30° C. |
| Water hardness | 15° dH |
| Soil | Wfk09V 0.7 g/L |

Model detergents and test materials were as follows:

| | |
|---|---|
| Laundry liquid model detergent | Model detergent A |
| Test material | Brevundimonas sp. 2-day biofilm grown on WFK10 (cotton) or WFK30A (polyester) |

For wash experiments, Model detergent A (containing 12% LAS, 11% AEO Biosoft N25-7 (NI), 7% AEOS (SLES), 6% MPG, 3% ethanol, 3% TEA, 2.75% cocoa soap, 2.75% soya soap, 2% glycerol, 2% sodium hydroxide, 2% sodium citrate, 1% sodium formate, 0.2% DTMPA and 0.2% PCA (all percentages are w/w)) (3.3 g/L) dissolved in water hardness 15° dH (Ca:Mg:NaHCO3-=4:1:1.5) was used. Soil was subsequently added to reach a concentration of 0.7 g soil/L (WFK09V pigment soil) to reveal biofilm. After washing, textiles were flushed in tap water and dried over night before scanning. Wash experiments were done twice.

Wash performance was measured as the brightness of the WFK09V pigment soiled, washed textile. Brightness can also be expressed as the intensity of the light reflected from the sample when illuminated with white light. When the sample is soiled, the intensity of the reflected light is lower, than that of a clean sample. Therefore, the intensity of the reflected light can be used to measure wash performance. Intensity measurements were made with a professional flatbed scanner (Kodak iQsmart, Kodak, Midtager 29, DK-2605 Brøndby, Denmark), which was used to capture an image of the washed and dried textile. To extract a value for the light intensity from the scanned images, 24-bit pixel values from the image were converted into values for red, green and blue (RGB). The intensity value (Int) was calculated by adding the RGB values together as vectors and then taking the length of the resulting vector:

$$Int = \sqrt{r^2 + g^2 + b^2}$$

Example 3: Wash Synergy Between DNase and Cellulase

To asses wash synergy between DNase (SEQ ID NO 13) and cellulase (SEQ ID NO 85) biofilm-harboring textile was AMSA washed a) in the absence of enzyme (blank), b) in the presence of DNase alone, c) in the presence of cellulase alone and d) with a mixture of DNase and cellulase. The resulting textile intensities and corresponding wash performances (WPs) are listed in Table 1 and 2. Wash performances attributable to DNase ($WP_{DNase}$), cellulase ($WP_{Cellu}$) and the mixture of the two ($WP_{DNase+Cellu}$) were quantified as the difference in intensity between textile washed with and without enzyme: $WP_{DNase}=I_{DNase}-I_{Blank}$, $WP_{Cellu}=I_{Cellu}-I_{Blank}$, $WP_{DNase+Cellu}=I_{DNase+Cellu}-I_{Blank}$. The synergistic component of wash performance $WP_{syn}$ was quantified as the extent to which wash performance of mixed DNase and cellulase ($WP_{DNase+Cellu}$) exceeded the sum of the individual wash performances of DNase alone and cellulase alone: $WP_{syn}=WP_{DNase+Cellu}-(WP_{DNase}\ WP_{Cellu})$.

TABLE 1 synergistic wash effect of DNase and cellulase (wash experiment 1)

|  | Cellulase (SEQ ID NO 85) | I | WP | $WP_{syn}$ |
|---|---|---|---|---|
| Blank | No enzyme | 285.460 | — | — |
| DNase | 0.00002 ppm DNase | 298.681 | 13.22 | — |
| Cellulase | 0.015% Cellulase | 289.347 | 3.89 | — |
|  | 0.15% Cellulase | 290.955 | 5.49 | — |

TABLE 1-continued synergistic wash effect of DNase and cellulase (wash experiment 1)

|  | Cellulase (SEQ ID NO 85) | I | WP | $WP_{syn}$ |
|---|---|---|---|---|
| DNase + Cellulase | 0.00002 ppm DNase + 0.015% Cellulase | 304.770 | 19.31 | 2.20 |
|  | 0.00002 ppm DNase + 0.15% Cellulase | 310.821 | 25.36 | 6.65 |

TABLE 2 synergistic wash effect of DNase and cellulase (wash experiment 2)

|  | Cellulose (SEQ ID NO 91) | I | WP | $WP_{syn}$ |
|---|---|---|---|---|
| Blank | No enzyme | 286.616 | — | — |
| DNase | 0.00002 ppm DNase | 322.453 | 35.84 | — |
| Cellulase | 0.015% Cellulase | 287.859 | 1.24 | — |
|  | 0.15% Cellulase | 291.329 | 4.71 | — |
| DNase + Cellulase | 0.00002 ppm DNase + 0.015% Cellulase | 326.890 | 40.27 | 3.19 |
|  | 0.00002 ppm DNase + 0.15% Cellulase | 332.886 | 46.27 | 5.72 |

What is claimed is:

1. A cleaning composition comprising
   (a) a DNAse having at least 85% sequence identity to the polypeptide of SEQ ID NO: 13,
   (b) a mannanase having mannanase activity and at least 90% sequence identity to the polypeptide of SEQ ID NO: 82, and
   (c) a cleaning component.

2. The cleaning composition of claim 1, wherein the DNase has at least 90% sequence identity to the polypeptide of SEQ ID NO: 13.

3. The cleaning composition of claim 1, wherein the DNase has at least 95% sequence identity to the polypeptide of SEQ ID NO: 13.

4. The cleaning composition of claim 1, wherein the DNase has at least 98% sequence identity to the polypeptide of SEQ ID NO: 13.

5. The cleaning composition of claim 1, wherein the DNase is the polypeptide of SEQ ID NO: 13.

6. The cleaning composition of claim 1, wherein the mannanase has at least 95% sequence identity to the polypeptide of SEQ ID NO: 82.

7. The cleaning composition of claim 1, wherein the mannanase has at least 97% sequence identity to the polypeptide of SEQ ID NO: 82.

8. The cleaning composition of claim 1, further comprising a cellulase.

9. The cleaning composition of claim 8, wherein the cellulase is selected from the group consisting of:
   a polypeptide having at least 80% sequence identity to the polypeptide shown in SEQ ID NO: 83,
   a polypeptide having at least 80% sequence identity to the polypeptide shown in SEQ ID NO: 84,
   a polypeptide having at least 80% sequence identity to the polypeptide shown in SEQ ID NO: 85, and
   a polypeptide having at least 80% sequence identity to the polypeptide shown in SEQ ID NO: 86.

10. The cleaning composition of claim 1, further comprising an amylase.

11. The cleaning composition of claim 10, wherein the amylase is a polypeptide selected from the group consisting of:
    a polypeptide having at least 80% sequence identity to the polypeptide shown in SEQ ID NO: 88,
    a polypeptide having at least 80% sequence identity to the polypeptide shown in SEQ ID NO: 89,
    a polypeptide having at least 80% sequence identity to the polypeptide shown in SEQ ID NO: 90, and
    a polypeptide having at least 80% sequence identity to the polypeptide shown in SEQ ID NO: 91.

12. The cleaning composition of claim 1, further comprising a xylanase.

13. The cleaning composition of claim 12, wherein the xylanase is a polypeptide having at least 80% sequence identity to the polypeptide shown in SEQ ID NO: 87.

14. The cleaning composition of claim 1, wherein the DNase comprises one or both of the motif(s) [D/M/L][S/T]GYSR[D/N] (SEQ ID NO: 73) or ASXNRSKG (SEQ ID NO: 74).

15. The cleaning composition of claim 1, wherein the amount of the DNase is from 0.01 to 1000 ppm and the amount of the mannanase is from 0.01 to 1000 ppm.

16. The cleaning composition of claim 1, wherein the cleaning component is a surfactant.

17. The cleaning composition of claim 16, wherein the surfactant is an anionic and/or nonionic surfactant.

18. The cleaning composition of claim 1, wherein the cleaning component is a builder or bleach component.

19. A kit for deep cleaning, which comprises a solution of a mixture comprising (a) a DNase having DNA activity and at least 85% sequence identity to the polypeptide of SEQ ID NO:13, (b) a mannanase having mannanase activity and at least 90% sequence identity to the polypeptide of SEQ ID NO: 82, and (c) a cleaning component.

20. A method of deep cleaning a textile, comprising washing the textile with a cleaning composition of claim 1.

* * * * *

SEQUENCE LISTING

```
<160> NUMBER OF SEQ ID NOS: 91

<210> SEQ ID NO 1
<211> LENGTH: 182
<212> TYPE: PRT
<213> ORGANISM: Bacillus sp-62451

<400> SEQUENCE: 1

Leu Pro Pro Asp Leu Pro Ser Lys Ser Thr Thr Gln Ala Gln Leu Asn
1               5                   10                  15

Ser Leu Asn Val Lys Asn Glu Glu Ser Met Ser Gly Tyr Ser Arg Glu
            20                  25                  30

Lys Phe Pro His Trp Ile Ser Gln Gly Asp Gly Cys Asp Thr Arg Gln
        35                  40                  45

Val Ile Leu Lys Arg Asp Ala Asp Asn Tyr Ser Gly Asn Cys Pro Val
    50                  55                  60

Thr Ser Gly Lys Trp Tyr Ser Tyr Tyr Asp Gly Ile Thr Phe Asn Asp
65                  70                  75                  80

Pro Ser Gln Leu Asp Ile Asp His Val Val Pro Leu Ala Glu Ala Trp
                85                  90                  95

Arg Ser Gly Ala Ser Ser Trp Ser Thr Ala Lys Arg Glu Asp Phe Ala
            100                 105                 110

Asn Asp Leu Asn Gly Pro Gln Leu Ile Ala Val Ser Ala Ser Ser Asn
        115                 120                 125

Arg Ser Lys Gly Asp Gln Asp Pro Ser Thr Trp Gln Pro Pro Arg Ala
    130                 135                 140

Gly Ala Asn Cys Ala Tyr Ala Lys Met Trp Ile Asn Thr Lys Tyr Asn
145                 150                 155                 160

Trp Gly Leu His Leu Gln Ser Ser Glu Lys Thr Ala Leu Gln Gly Met
                165                 170                 175

Leu Asn Ser Cys Ser Tyr
            180
```

```
<210> SEQ ID NO 2
<211> LENGTH: 182
<212> TYPE: PRT
<213> ORGANISM: Bacillus horikoshii

<400> SEQUENCE: 2
```

| | | | | | | | | | | | | | | |
|---|---|---|---|---|---|---|---|---|---|---|---|---|---|---|
| Leu | Pro | Pro | Gly | Thr | Pro | Thr | Lys | Ser | Glu | Ala | Gln | Asn | Gln | Leu | Asn |
| 1 | | | | 5 | | | | | 10 | | | | | 15 |

| Ser | Leu | Thr | Val | Lys | Ser | Glu | Gly | Ser | Met | Thr | Gly | Tyr | Ser | Arg | Asp |
|---|---|---|---|---|---|---|---|---|---|---|---|---|---|---|---|
| | | | 20 | | | | | 25 | | | | | 30 | | |

| Leu | Phe | Pro | His | Trp | Ser | Gly | Gln | Gly | Asn | Gly | Cys | Asp | Thr | Arg | Gln |
|---|---|---|---|---|---|---|---|---|---|---|---|---|---|---|---|
| | | | 35 | | | | | 40 | | | | | 45 | | |

| Ile | Val | Leu | Gln | Arg | Asp | Ala | Asp | Tyr | Tyr | Thr | Gly | Thr | Cys | Pro | Thr |
|---|---|---|---|---|---|---|---|---|---|---|---|---|---|---|---|
| | 50 | | | | | 55 | | | | | 60 | | | | |

| Thr | Ser | Gly | Lys | Trp | Tyr | Ser | Tyr | Phe | Asp | Gly | Val | Ile | Val | Tyr | Ser |
|---|---|---|---|---|---|---|---|---|---|---|---|---|---|---|---|
| 65 | | | | | 70 | | | | | 75 | | | | | 80 |

| Pro | Ser | Glu | Ile | Asp | Ile | Asp | His | Ile | Val | Pro | Leu | Ala | Glu | Ala | Trp |
|---|---|---|---|---|---|---|---|---|---|---|---|---|---|---|---|
| | | | | 85 | | | | | 90 | | | | | 95 | |

| Arg | Ser | Gly | Ala | Ser | Ser | Trp | Thr | Thr | Glu | Gln | Arg | Arg | Ala | Phe | Ala |
|---|---|---|---|---|---|---|---|---|---|---|---|---|---|---|---|
| | | | 100 | | | | | 105 | | | | | 110 | | |

| Asn | Asp | Leu | Asn | Gly | Pro | Gln | Leu | Ile | Ala | Val | Thr | Ala | Ser | Val | Asn |
|---|---|---|---|---|---|---|---|---|---|---|---|---|---|---|---|
| | | | 115 | | | | | 120 | | | | | 125 | | |

| Arg | Ser | Lys | Gly | Asp | Gln | Asp | Pro | Ser | Thr | Trp | Gln | Pro | Pro | Arg | Ala |
|---|---|---|---|---|---|---|---|---|---|---|---|---|---|---|---|
| | 130 | | | | | 135 | | | | | 140 | | | | |

| Gly | Ala | Arg | Cys | Ala | Tyr | Ala | Lys | Trp | Trp | Ile | Asn | Thr | Lys | His | Arg |
|---|---|---|---|---|---|---|---|---|---|---|---|---|---|---|---|
| 145 | | | | | 150 | | | | | 155 | | | | | 160 |

| Trp | Asn | Leu | His | Leu | Gln | Ser | Ser | Glu | Lys | Ser | Ser | Leu | Gln | Thr | Met |
|---|---|---|---|---|---|---|---|---|---|---|---|---|---|---|---|
| | | | | 165 | | | | | 170 | | | | | 175 | |

| Leu | Asn | Gly | Cys | Ala | Tyr |
|---|---|---|---|---|---|
| | | | 180 | | |

```
<210> SEQ ID NO 3
<211> LENGTH: 182
<212> TYPE: PRT
<213> ORGANISM: Bacillus sp-62520

<400> SEQUENCE: 3
```

| Leu | Pro | Pro | Gly | Thr | Pro | Ser | Lys | Ser | Glu | Ala | Gln | Ser | Gln | Leu | Asn |
|---|---|---|---|---|---|---|---|---|---|---|---|---|---|---|---|
| 1 | | | | 5 | | | | | 10 | | | | | 15 | |

| Ala | Leu | Thr | Val | Lys | Pro | Glu | Asp | Pro | Met | Thr | Gly | Tyr | Ser | Arg | Asp |
|---|---|---|---|---|---|---|---|---|---|---|---|---|---|---|---|
| | | | 20 | | | | | 25 | | | | | 30 | | |

| His | Phe | Pro | His | Trp | Ile | Ser | Gln | Gly | Asn | Gly | Cys | Asn | Thr | Arg | Gln |
|---|---|---|---|---|---|---|---|---|---|---|---|---|---|---|---|
| | | | 35 | | | | | 40 | | | | | 45 | | |

| Ile | Val | Leu | Gln | Arg | Asp | Ala | Asp | Tyr | Tyr | Ser | Gly | Ala | Cys | Pro | Val |
|---|---|---|---|---|---|---|---|---|---|---|---|---|---|---|---|
| | 50 | | | | | 55 | | | | | 60 | | | | |

| Thr | Thr | Gly | Lys | Trp | Tyr | Ser | Tyr | Phe | Asp | Gly | Val | Ile | Val | Tyr | Ser |
|---|---|---|---|---|---|---|---|---|---|---|---|---|---|---|---|
| 65 | | | | | 70 | | | | | 75 | | | | | 80 |

| Pro | Ser | Glu | Ile | Asp | Ile | Asp | His | Ile | Val | Pro | Leu | Ala | Glu | Ala | Trp |
|---|---|---|---|---|---|---|---|---|---|---|---|---|---|---|---|
| | | | | 85 | | | | | 90 | | | | | 95 | |

| Arg | Ser | Gly | Ala | Ser | Ser | Trp | Thr | Thr | Glu | Lys | Arg | Arg | Ser | Phe | Ala |
|---|---|---|---|---|---|---|---|---|---|---|---|---|---|---|---|
| | | | 100 | | | | | 105 | | | | | 110 | | |

| Asn | Asp | Leu | Asn | Gly | Pro | Gln | Leu | Ile | Ala | Val | Thr | Ala | Ser | Val | Asn |
|---|---|---|---|---|---|---|---|---|---|---|---|---|---|---|---|
| | | | 115 | | | | | 120 | | | | | 125 | | |

| Arg | Ser | Lys | Gly | Asp | Gln | Asp | Pro | Ser | Thr | Trp | Gln | Pro | Pro | Arg | Ala |
|---|---|---|---|---|---|---|---|---|---|---|---|---|---|---|---|
| | 130 | | | | | 135 | | | | | 140 | | | | |

Gly Ala Arg Cys Ala Tyr Ala Lys Trp Trp Ile Asn Thr Lys His Arg
145                 150                 155                 160

Trp Gly Leu His Leu Gln Ser Ser Glu Lys Ser Ser Leu Gln Ser Met
            165                 170                 175

Leu Asn Gly Cys Ala Tyr
            180

<210> SEQ ID NO 4
<211> LENGTH: 182
<212> TYPE: PRT
<213> ORGANISM: Bacillus sp-62520

<400> SEQUENCE: 4

Leu Pro Pro Gly Thr Pro Ser Lys Ser Glu Ala Gln Ser Gln Leu Asn
1               5                   10                  15

Ala Leu Thr Val Lys Pro Glu Asp Pro Met Thr Gly Tyr Ser Arg Asp
            20                  25                  30

His Phe Pro His Trp Ile Ser Gln Gly Asn Gly Cys Asn Thr Arg Gln
        35                  40                  45

Ile Val Leu Gln Arg Asp Ala Asp Tyr Tyr Ser Gly Ala Cys Pro Val
    50                  55                  60

Thr Thr Gly Lys Trp Tyr Ser Tyr Phe Asp Gly Val Ile Val Tyr Ser
65                  70                  75                  80

Pro Ser Glu Ile Asp Ile Asp His Ile Val Pro Leu Ala Glu Ala Trp
                85                  90                  95

Arg Ser Gly Ala Ser Ser Trp Thr Thr Glu Gln Arg Arg Ser Phe Ala
            100                 105                 110

Asn Asp Leu Asn Gly Pro Gln Leu Ile Ala Val Thr Ala Ser Val Asn
        115                 120                 125

Arg Ser Lys Gly Asp Gln Asp Pro Ser Thr Trp Gln Pro Pro Arg Ala
    130                 135                 140

Gly Ala Arg Cys Ala Tyr Ala Lys Trp Trp Ile Asn Thr Lys His Arg
145                 150                 155                 160

Trp Gly Leu His Leu Gln Ser Ser Glu Lys Ser Ser Leu Gln Ser Met
            165                 170                 175

Leu Asn Gly Cys Ala Tyr
            180

<210> SEQ ID NO 5
<211> LENGTH: 182
<212> TYPE: PRT
<213> ORGANISM: Bacillus horikoshii

<400> SEQUENCE: 5

Leu Pro Pro Gly Thr Pro Ser Lys Ser Glu Ala Gln Ser Gln Leu Asn
1               5                   10                  15

Ser Leu Thr Val Lys Ser Glu Asp Pro Met Thr Gly Tyr Ser Arg Asp
            20                  25                  30

His Phe Pro His Trp Ser Gly Gln Gly Asn Gly Cys Asp Thr Arg Gln
        35                  40                  45

Ile Val Leu Gln Arg Asp Ala Asp Tyr Tyr Ser Gly Asn Cys Pro Val
    50                  55                  60

Thr Ser Gly Lys Trp Tyr Ser Tyr Phe Asp Gly Val Ile Val Tyr Ser
65                  70                  75                  80

Pro Ser Glu Ile Asp Ile Asp His Val Val Pro Leu Ala Glu Ala Trp
                85                  90                  95

```
Arg Ser Gly Ala Ser Ser Trp Thr Thr Glu Gln Arg Ser Phe Ala
            100                 105                 110

Asn Asp Leu Asn Gly Pro Gln Leu Ile Ala Val Thr Ala Ser Val Asn
            115                 120                 125

Arg Ser Lys Gly Asp Gln Asp Pro Ser Thr Trp Gln Pro Pro Arg Ala
            130                 135                 140

Gly Ala Arg Cys Ala Tyr Ala Lys Trp Trp Ile Asn Thr Lys His Arg
145                 150                 155                 160

Trp Asn Leu His Leu Gln Ser Ser Glu Lys Ser Ala Leu Gln Thr Met
                165                 170                 175

Leu Asn Gly Cys Val Tyr
            180

<210> SEQ ID NO 6
<211> LENGTH: 182
<212> TYPE: PRT
<213> ORGANISM: Bacillus horikoshii

<400> SEQUENCE: 6

Leu Pro Pro Gly Thr Pro Ser Lys Ser Glu Ala Gln Ser Gln Leu Asn
1               5                   10                  15

Ser Leu Thr Val Lys Thr Glu Asp Pro Met Thr Gly Tyr Ser Arg Asp
            20                  25                  30

Leu Phe Pro His Trp Ser Gly Gln Gly Ser Gly Cys Asp Thr Arg Gln
            35                  40                  45

Ile Val Leu Gln Arg Asp Ala Asp Tyr Phe Thr Gly Thr Cys Pro Thr
        50                  55                  60

Thr Ser Gly Lys Trp Tyr Ser Tyr Phe Asp Gly Val Ile Val Tyr Ser
65                  70                  75                  80

Pro Ser Glu Ile Asp Val Asp His Ile Val Pro Leu Ala Glu Ala Trp
                85                  90                  95

Arg Ser Gly Ala Ser Ser Trp Thr Thr Glu Gln Arg Arg Ala Phe Ala
            100                 105                 110

Asn Asp Leu Thr Gly Pro Gln Leu Ile Ala Val Thr Ala Ser Val Asn
            115                 120                 125

Arg Ser Lys Gly Asp Gln Asp Pro Ser Thr Trp Gln Pro Pro Arg Ala
            130                 135                 140

Gly Ala Arg Cys Ala Tyr Ala Lys Trp Trp Ile Asn Thr Lys His Arg
145                 150                 155                 160

Trp Asn Leu His Leu Gln Ser Ser Glu Lys Ser Ser Leu Gln Thr Met
                165                 170                 175

Leu Asn Gly Cys Ala Tyr
            180

<210> SEQ ID NO 7
<211> LENGTH: 182
<212> TYPE: PRT
<213> ORGANISM: Bacillus sp-16840

<400> SEQUENCE: 7

Leu Pro Pro Gly Thr Pro Ser Lys Ser Glu Ala Gln Ser Gln Leu Asn
1               5                   10                  15

Ala Leu Thr Val Lys Ala Glu Asp Pro Met Thr Gly Tyr Ser Arg Asn
            20                  25                  30

Leu Phe Pro His Trp Asn Ser Gln Gly Asn Gly Cys Asn Thr Arg Gln
            35                  40                  45
```

Leu Val Leu Gln Arg Asp Ala Asp Tyr Tyr Ser Gly Asn Cys Pro Val
            50                  55                  60

Thr Ser Gly Arg Trp Tyr Ser Tyr Phe Asp Gly Val Val Val Thr Ser
 65                  70                  75                  80

Pro Ser Glu Ile Asp Ile Asp His Ile Val Pro Leu Ala Glu Ala Trp
                 85                  90                  95

Arg Ser Gly Ala Ser Ser Trp Thr Thr Glu Lys Arg Lys Glu Phe Ala
                100                 105                 110

Asn Asp Leu Asn Gly Pro Gln Leu Ile Ala Val Thr Ala Ser Val Asn
                115                 120                 125

Arg Ser Lys Gly Asp Gln Asp Pro Ser Thr Trp Gln Pro Pro Arg Ala
            130                 135                 140

Ala Ala Arg Cys Gly Tyr Ala Lys Trp Trp Ile Asn Thr Lys Tyr Arg
145                 150                 155                 160

Trp Asp Leu Ser Leu Gln Ser Ser Glu Lys Ser Ser Leu Gln Thr Met
                165                 170                 175

Leu Asn Thr Cys Ser Tyr
            180

<210> SEQ ID NO 8
<211> LENGTH: 182
<212> TYPE: PRT
<213> ORGANISM: Bacillus sp-16840

<400> SEQUENCE: 8

Leu Pro Pro Gly Thr Pro Ser Lys Ser Gln Ala Gln Ser Gln Leu Asn
 1               5                  10                  15

Ala Leu Thr Val Lys Ala Glu Asp Pro Met Thr Gly Tyr Ser Arg Asn
                 20                  25                  30

Leu Phe Pro His Trp Ser Ser Gln Gly Asn Gly Cys Asn Thr Arg Gln
             35                  40                  45

Leu Val Leu Gln Arg Asp Ala Asp Tyr Tyr Ser Gly Asn Cys Pro Val
            50                  55                  60

Thr Ser Gly Arg Trp Tyr Ser Tyr Phe Asp Gly Val Val Val Thr Ser
 65                  70                  75                  80

Pro Ser Glu Ile Asp Ile Asp His Ile Val Pro Leu Ala Glu Ala Trp
                 85                  90                  95

Arg Ser Gly Ala Ser Ser Trp Thr Thr Glu Lys Arg Lys Glu Phe Ala
                100                 105                 110

Asn Asp Leu Asn Gly Pro Gln Leu Ile Ala Val Thr Ala Ser Val Asn
                115                 120                 125

Arg Ser Lys Gly Asp Gln Asp Pro Ser Thr Trp Gln Pro Pro Arg Val
            130                 135                 140

Ala Ala Arg Cys Gly Tyr Ala Lys Trp Trp Ile Asn Thr Lys Tyr Arg
145                 150                 155                 160

Trp Asp Leu Ser Leu Gln Ser Ser Glu Lys Ser Ser Leu Gln Thr Met
                165                 170                 175

Leu Asn Thr Cys Ser Tyr
            180

<210> SEQ ID NO 9
<211> LENGTH: 182
<212> TYPE: PRT
<213> ORGANISM: Bacillus sp-62668

<400> SEQUENCE: 9

Leu Pro Pro Gly Thr Pro Ser Lys Ser Glu Ala Gln Ser Gln Leu Thr
1               5                   10                  15

Ser Leu Thr Val Lys Pro Glu Asp Pro Met Thr Gly Tyr Ser Arg Asp
            20                  25                  30

His Phe Pro His Trp Ile Ser Gln Gly Asn Gly Cys Asn Thr Arg Gln
        35                  40                  45

Ile Val Leu Gln Arg Asp Ala Asp Tyr Tyr Ser Gly Asn Cys Pro Val
    50                  55                  60

Thr Thr Gly Lys Trp Tyr Ser Tyr Phe Asp Gly Val Ile Val Tyr Ser
65                  70                  75                  80

Pro Ser Glu Ile Asp Ile Asp His Ile Val Pro Leu Ala Glu Ala Trp
                85                  90                  95

Arg Ser Gly Ala Ser Ser Trp Thr Ala Glu Gln Arg Arg Asn Phe Ala
            100                 105                 110

Asn Asp Leu Asn Gly Pro Gln Leu Ile Ala Val Thr Ala Ser Val Asn
        115                 120                 125

Arg Ser Lys Gly Asp Gln Asp Pro Ser Thr Trp Gln Pro Pro Arg Thr
130                 135                 140

Gly Ala Arg Cys Ala Tyr Ala Lys Trp Trp Ile Asn Thr Lys Tyr Arg
145                 150                 155                 160

Trp Gly Leu His Leu Gln Ser Ser Glu Lys Ser Ser Leu Gln Ser Met
                165                 170                 175

Leu Asn Gly Cys Ala Tyr
            180

<210> SEQ ID NO 10
<211> LENGTH: 183
<212> TYPE: PRT
<213> ORGANISM: Bacillus sp-13395

<400> SEQUENCE: 10

Ala Phe Pro Pro Gly Thr Pro Ser Lys Ser Thr Ala Gln Ser Gln Leu
1               5                   10                  15

Asn Ser Leu Thr Val Lys Ser Glu Gly Ser Met Thr Gly Tyr Ser Arg
            20                  25                  30

Asp Lys Phe Pro His Trp Ile Ser Gln Gly Asp Gly Cys Asp Thr Arg
        35                  40                  45

Gln Leu Val Leu Lys Arg Asp Gly Asp Tyr Tyr Ser Gly Asn Cys Pro
    50                  55                  60

Val Thr Ser Gly Lys Trp Tyr Ser Tyr Tyr Asp Gly Ile Ala Val Tyr
65                  70                  75                  80

Ser Pro Ser Glu Ile Asp Ile Asp His Ile Val Pro Leu Ala Glu Ala
                85                  90                  95

Trp Arg Ser Gly Ala Ser Gly Trp Thr Thr Glu Lys Arg Gln Asn Phe
            100                 105                 110

Ala Asn Asp Leu Asn Gly Pro Gln Leu Ile Ala Val Thr Ala Ser Val
        115                 120                 125

Asn Arg Ser Lys Gly Asp Gln Asp Pro Ser Thr Trp Gln Pro Pro Arg
130                 135                 140

Ser Gly Ser His Cys Ala Tyr Ala Lys Met Trp Val Asn Thr Lys Tyr
145                 150                 155                 160

Arg Trp Gly Leu His Leu Gln Ser Ala Glu Lys Ser Ala Leu Gln Ser
                165                 170                 175

```
Met Leu Asn Ala Cys Ser Tyr
            180

<210> SEQ ID NO 11
<211> LENGTH: 185
<212> TYPE: PRT
<213> ORGANISM: Bacillus horneckiae

<400> SEQUENCE: 11

Ala Ser Ala Phe Pro Pro Gly Thr Pro Ser Lys Ser Thr Ala Gln Ser
1               5                   10                  15

Gln Leu Asn Ser Leu Thr Val Lys Ser Glu Gly Ser Met Thr Gly Tyr
            20                  25                  30

Ser Arg Asp Lys Phe Pro His Trp Ile Ser Gln Gly Asp Gly Cys Asp
        35                  40                  45

Thr Arg Gln Leu Val Leu Lys Arg Asp Gly Asp Tyr Tyr Ser Gly Asn
    50                  55                  60

Cys Pro Val Thr Ser Gly Lys Trp Tyr Ser Tyr Tyr Asp Gly Ile Thr
65                  70                  75                  80

Val Tyr Ser Pro Ser Glu Ile Asp Ile Asp His Ile Val Pro Leu Ala
                85                  90                  95

Glu Ala Trp Arg Ser Gly Ala Ser Gly Trp Thr Thr Glu Lys Arg Gln
            100                 105                 110

Ser Phe Ala Asn Asp Leu Asn Gly Pro Gln Leu Ile Ala Val Thr Ala
        115                 120                 125

Ser Val Asn Arg Ser Lys Gly Asp Gln Asp Pro Ser Thr Trp Gln Pro
    130                 135                 140

Pro Arg Ser Gly Ser His Cys Ala Tyr Ala Lys Met Trp Val Asn Thr
145                 150                 155                 160

Lys Tyr Arg Trp Gly Leu His Val Gln Ser Ala Glu Lys Ser Ala Leu
                165                 170                 175

Gln Ser Met Leu Asn Ala Cys Ser Tyr
            180                 185

<210> SEQ ID NO 12
<211> LENGTH: 182
<212> TYPE: PRT
<213> ORGANISM: Bacillus sp-11238

<400> SEQUENCE: 12

Phe Pro Pro Glu Ile Pro Ser Lys Ser Thr Ala Gln Ser Gln Leu Asn
1               5                   10                  15

Ser Leu Thr Val Lys Ser Glu Asp Ala Met Thr Gly Tyr Ser Arg Asp
            20                  25                  30

Lys Phe Pro His Trp Ile Ser Gln Gly Asp Gly Cys Asp Thr Arg Gln
        35                  40                  45

Met Val Leu Lys Arg Asp Ala Asp Tyr Tyr Ser Gly Ser Cys Pro Val
    50                  55                  60

Thr Ser Gly Lys Trp Tyr Ser Tyr Tyr Asp Gly Ile Thr Val Tyr Ser
65                  70                  75                  80

Pro Ser Glu Ile Asp Ile Asp His Ile Val Pro Leu Ala Glu Ala Trp
                85                  90                  95

Arg Ser Gly Ala Ser Ser Trp Thr Thr Glu Lys Arg Arg Asn Phe Ala
            100                 105                 110

Asn Asp Leu Asn Gly Pro Gln Leu Ile Ala Val Thr Ala Ser Val Asn
        115                 120                 125
```

Arg Ser Lys Gly Asp Gln Asp Pro Ser Thr Trp Gln Pro Pro Arg Ser
130                 135                 140

Gly Ala Arg Cys Ala Tyr Ala Lys Met Trp Val Asn Thr Lys Tyr Arg
145                 150                 155                 160

Trp Gly Leu His Leu Gln Ser Ala Glu Lys Ser Gly Leu Glu Ser Met
                165                 170                 175

Leu Asn Thr Cys Ser Tyr
            180

<210> SEQ ID NO 13
<211> LENGTH: 182
<212> TYPE: PRT
<213> ORGANISM: Bacillus cibi

<400> SEQUENCE: 13

Thr Pro Pro Gly Thr Pro Ser Lys Ser Ala Ala Gln Ser Gln Leu Asn
1               5                   10                  15

Ala Leu Thr Val Lys Thr Glu Gly Ser Met Ser Gly Tyr Ser Arg Asp
                20                  25                  30

Leu Phe Pro His Trp Ile Ser Gln Gly Ser Gly Cys Asp Thr Arg Gln
            35                  40                  45

Val Val Leu Lys Arg Asp Ala Asp Ser Tyr Ser Gly Asn Cys Pro Val
        50                  55                  60

Thr Ser Gly Ser Trp Tyr Ser Tyr Tyr Asp Gly Val Thr Phe Thr Asn
65                  70                  75                  80

Pro Ser Asp Leu Asp Ile Asp His Ile Val Pro Leu Ala Glu Ala Trp
                85                  90                  95

Arg Ser Gly Ala Ser Ser Trp Thr Thr Ser Lys Arg Gln Asp Phe Ala
            100                 105                 110

Asn Asp Leu Ser Gly Pro Gln Leu Ile Ala Val Ser Ala Ser Thr Asn
        115                 120                 125

Arg Ser Lys Gly Asp Gln Asp Pro Ser Thr Trp Gln Pro Pro Arg Ser
130                 135                 140

Gly Ala Ala Cys Gly Tyr Ser Lys Trp Trp Ile Ser Thr Lys Tyr Lys
145                 150                 155                 160

Trp Gly Leu Ser Leu Gln Ser Ser Glu Lys Thr Ala Leu Gln Gly Met
                165                 170                 175

Leu Asn Ser Cys Ser Tyr
            180

<210> SEQ ID NO 14
<211> LENGTH: 182
<212> TYPE: PRT
<213> ORGANISM: Bacillus sp-18318

<400> SEQUENCE: 14

Phe Pro Pro Gly Thr Pro Ser Lys Ser Thr Ala Gln Ser Gln Leu Asn
1               5                   10                  15

Ser Leu Thr Val Lys Ser Glu Gly Ser Met Thr Gly Tyr Ser Arg Asp
                20                  25                  30

Lys Phe Pro His Trp Ile Gly Gln Gly Ser Gly Cys Asp Thr Arg Gln
            35                  40                  45

Leu Val Leu Gln Arg Asp Ala Asp Tyr Tyr Ser Gly Ser Cys Pro Val
        50                  55                  60

Thr Ser Gly Lys Trp Tyr Ser Tyr Tyr Asp Gly Val Thr Phe Tyr Asp
65                  70                  75                  80

```
Pro Ser Asp Leu Asp Ile Asp His Val Val Pro Leu Ala Glu Ala Trp
            85                  90                  95

Arg Ser Gly Ala Ser Ser Trp Ser Thr Gln Lys Arg Lys Asp Phe Ala
            100                 105                 110

Asn Asp Leu Ser Gly Pro Gln Leu Ile Ala Val Ser Ala Ser Ser Asn
            115                 120                 125

Arg Ser Lys Gly Asp Gln Asp Pro Ser Thr Trp Gln Pro Thr Arg Ser
            130                 135                 140

Gly Ala Ala Cys Gly Tyr Ser Lys Trp Trp Ile Ser Thr Lys His Lys
145                 150                 155                 160

Trp Gly Leu Ser Leu Gln Ser Ser Glu Lys Asn Ala Leu Gln Gly Met
            165                 170                 175

Leu Asn Ser Cys Val Tyr
            180

<210> SEQ ID NO 15
<211> LENGTH: 182
<212> TYPE: PRT
<213> ORGANISM: Bacillus idriensis

<400> SEQUENCE: 15

Leu Pro Pro Gly Thr Pro Ser Lys Ser Thr Ala Gln Ser Gln Leu Asn
1               5                   10                  15

Ala Leu Thr Val Gln Thr Glu Gly Ser Met Thr Gly Tyr Ser Arg Asp
            20                  25                  30

Lys Phe Pro His Trp Ile Ser Gln Gly Asn Gly Cys Asp Thr Arg Gln
            35                  40                  45

Val Val Leu Gln Arg Asp Ala Asp Tyr Tyr

```
Lys Phe Pro His Trp Ile Gly Gln Gly Asn Gly Cys Asp Thr Arg Gln
            35                  40                  45

Leu Val Leu Gln Arg Asp Ala Asp Tyr Tyr Ser Gly Asp Cys Pro Val
 50                  55                  60

Thr Ser Gly Lys Trp Tyr Ser Tyr Phe Asp Gly Val Thr Val Tyr Asp
 65                  70                  75                  80

Pro Ser Asp Leu Asp Ile Asp His Met Val Pro Met Ala Glu Ala Trp
                 85                  90                  95

Arg Ser Gly Ala Ser Ser Trp Ser Thr Gln Lys Arg Glu Asp Phe Ala
            100                 105                 110

Asn Asp Leu Ser Gly Pro His Leu Ile Ala Val Thr Ala Ser Ser Asn
            115                 120                 125

Arg Ser Lys Gly Asp Gln Asp Pro Ser Thr Trp Lys Pro Thr Arg Tyr
        130                 135                 140

Gly Ala His Cys Gly Tyr Ala Lys Trp Trp Ile Asn Thr Lys Tyr Val
145                 150                 155                 160

Tyr Asp Leu Thr Leu Gln Ser Ser Glu Lys Thr Glu Leu Gln Ser Met
                165                 170                 175

Leu Asn Thr Cys Ser Tyr
            180

<210> SEQ ID NO 17
<211> LENGTH: 182
<212> TYPE: PRT
<213> ORGANISM: Enviromental sample J

<400> SEQUENCE: 17

Leu Pro Pro Asn Ile Pro Ser Lys Ala Asp Ala Leu Thr Lys Leu Asn
  1               5                  10                  15

Ala Leu Thr Val Gln Thr Glu Gly Pro Met Thr Gly Tyr Ser Arg Asp
             20                  25                  30

Leu Phe Pro His Trp Ser Ser Gln Gly Asn Gly Cys Asn Thr Arg His
            35                  40                  45

Val Val Leu Lys Arg Asp Ala Asp Ser Val Val Asp Thr Cys Pro Val
 50                  55                  60

Thr Thr Gly Arg Trp Tyr Ser Tyr Tyr Asp Gly Leu Val Phe Thr Ser
 65                  70                  75                  80

Ala Ser Asp Ile Asp Ile Asp His Val Val Pro Leu Ala Glu Ala Trp
                 85                  90                  95

Arg Ser Gly Ala Ser Ser Trp Thr Ser Thr Lys Arg Gln Ser Phe Ala
            100                 105                 110

Asn Asp Leu Asn Gly Pro Gln Leu Ile Ala Val Ser Ala Thr Ser Asn
            115                 120                 125

Arg Ser Lys Gly Asp Gln Asp Pro Ser Thr Trp Gln Pro Pro Arg Ala
        130                 135                 140

Gly Ala Arg Cys Ala Tyr Ala Lys Met Trp Val Glu Thr Lys Ser Arg
145                 150                 155                 160

Trp Gly Leu Thr Leu Gln Ser Ser Glu Lys Ala Ala Leu Gln Thr Ala
                165                 170                 175

Ile Asn Ala Cys Ser Tyr
            180

<210> SEQ ID NO 18
<211> LENGTH: 182
<212> TYPE: PRT
```

<213> ORGANISM: Bacillus vietnamensis

<400> SEQUENCE: 18

```
Phe Pro Pro Gly Thr Pro Ser Lys Ser

```
Tyr Asp Leu Asn Leu Gln Ser Ser Glu Lys Ser Ala Leu Gln Ser Met
                165                 170                 175

Leu Asn Thr Cys Ser Tyr
            180

<210> SEQ ID NO 20
<211> LENGTH: 182
<212> TYPE: PRT
<213> ORGANISM: Paenibacillus mucilaginosus

<400> SEQUENCE: 20

Leu Pro Pro Gly Thr Pro Ser Lys Ser Thr Ala Gln Ser Gln Leu Asn
1               5                   10                  15

Ser Leu Thr Val Lys Ser Glu Ser Thr Met Thr Gly Tyr Ser Arg Asp
                20                  25                  30

Lys Phe Pro His Trp Thr Ser Gln Gly Gly Cys Asp Thr Arg Gln
            35                  40                  45

Val Val Leu Lys Arg Asp Ala Asp Tyr Tyr Ser Gly Ser Cys Pro Val
        50                  55                  60

Thr Ser Gly Lys Trp Tyr Ser Tyr Tyr Asp Gly Ile Thr Val Tyr Ser
65                  70                  75                  80

Pro Ser Glu Ile Asp Ile Asp His Ile Val Pro Leu Ala Glu Ala Trp
                85                  90                  95

Arg Ser Gly Ala Ser Ser Trp Thr Thr Glu Lys Arg Gln Asn Phe Ala
            100                 105                 110

Asn Asp Leu Gly Gly Pro Gln Leu Ile Ala Val Thr Ala Ser Ser Asn
        115                 120                 125

Arg Ala Lys Gly Asp Gln Asp Pro Ser Thr Trp Lys Pro Thr Arg Ser
    130                 135                 140

Gly Ala His Cys Ala Tyr Ala Lys Trp Trp Ile Asn Thr Lys Tyr Arg
145                 150                 155                 160

Trp Gly Leu His Leu Gln Ser Ser Glu Lys Thr Ala Leu Gln Ser Met
                165                 170                 175

Leu Asn Thr Cys Ser Tyr
            180

<210> SEQ ID NO 21
<211> LENGTH: 182
<212> TYPE: PRT
<213> ORGANISM: Bacillus indicus

<400> SEQUENCE: 21

Thr Pro Pro Gly Thr Pro Ser Lys Ser Thr Ala Gln Thr Gln Leu Asn
1               5                   10                  15

Ala Leu Thr Val Lys Thr Glu Gly Ser Met Thr Gly Tyr Ser Arg Asp
                20                  25                  30

Leu Phe Pro His Trp Ile Ser Gln Gly Ser Gly Cys Asp Thr Arg Gln
            35                  40                  45

Val Val Leu Lys Arg Asp Ala Asp Tyr Tyr Ser Gly Ser Cys Pro Val
        50                  55                  60

Thr Ser Gly Lys Trp Tyr Ser Tyr Tyr Asp Gly Val Thr Phe Tyr Asp
65                  70                  75                  80

Pro Ser Asp Leu Asp Ile Asp His Ile Val Pro Leu Ala Glu Ala Trp
                85                  90                  95

Arg Ser Gly Ala Ser Ser Trp Thr Thr Ser Lys Arg Gln Asp Phe Ala
            100                 105                 110
```

```
Asn Asp Leu Ser Gly Pro Gln Leu Ile Ala Val Ser Ala Ser Thr Asn
        115                 120                 125

Arg Ser Lys Gly Asp Gln Asp Pro Ser Thr Trp Gln Pro Pro Arg Ala
        130                 135                 140

Gly Ala Ala Cys Gly Tyr Ser Lys Trp Trp Ile Ser Thr Lys Tyr Lys
145                 150                 155                 160

Trp Gly Leu Ser Leu Gln Ser Ser Glu Lys Thr Ala Leu Gln Gly Met
            165                 170                 175

Leu Asn Ser Cys Ser Tyr
        180

<210> SEQ ID NO 22
<211> LENGTH: 182
<212> TYPE: PRT
<213> ORGANISM: Bacillus marisflavi

<400> SEQUENCE: 22

Thr Pro Pro Val Thr Pro Ser Lys Ala Thr Ser Gln Ser Gln Leu Asn
1               5                   10                  15

Gly Leu Thr Val Lys Thr Glu Gly Ala Met Thr Gly Tyr Ser Arg Asp
            20                  25                  30

Lys Phe Pro His Trp Ser Ser Gln Gly Gly Cys Asp Thr Arg Gln
        35                  40                  45

Val Val Leu Lys Arg Asp Ala Asp Ser Tyr Ser Gly Asn Cys Pro Val
    50                  55                  60

Thr Ser Gly Ser Trp Tyr Ser Tyr Tyr Asp Gly Val Lys Phe Thr Asn
65                  70                  75                  80

Pro Ser Asp Leu Asp Ile Asp His Ile Val Pro Leu Ala Glu Ala Trp
            85                  90                  95

Arg Ser Gly Ala Ser Ser Trp Thr Thr Ala Gln Arg Glu Ala Phe Ala
        100                 105                 110

Asn Asp Leu Ser Gly Ser Gln Leu Ile Ala Val Ser Ala Ser Ser Asn
        115                 120                 125

Arg Ser Lys Gly Asp Gln Asp Pro Ser Thr Trp Gln Pro Pro Arg Ala
        130                 135                 140

Gly Ala Lys Cys Gly Tyr Ala Lys Trp Trp Ile Ser Thr Lys Ser Lys
145                 150                 155                 160

Trp Asn Leu Ser Leu Gln Ser Ser Glu Lys Thr Ala Leu Gln Gly Met
            165                 170                 175

Leu Asn Ser Cys Val Tyr
        180

<210> SEQ ID NO 23
<211> LENGTH: 184
<212> TYPE: PRT
<213> ORGANISM: Bacillus luciferensis

<400> SEQUENCE: 23

Ala Ser Leu Pro Pro Gly Ile Pro Ser Leu Ser Thr Ala Gln Ser Gln
1               5                   10                  15

Leu Asn Ser Leu Thr Val Lys Ser Glu Gly Ser Leu Thr Gly Tyr Ser
            20                  25                  30

Arg Asp Val Phe Pro His Trp Ile Ser Gln Gly Ser Gly Cys Asp Thr
        35                  40                  45

Arg Gln Val Val Leu Lys Arg Asp Ala Asp Tyr Tyr Ser Gly Asn Cys
    50                  55                  60
```

```
Pro Val Thr Ser Gly Lys Trp Tyr Ser Tyr Tyr Asp Gly Val Thr Val
 65                  70                  75                  80

Tyr Ser Pro Ser Glu Ile Asp Ile Asp His Val Val Pro Leu Ala Glu
                 85                  90                  95

Ala Trp Arg Ser Gly Ala Ser Ser Trp Thr Thr Glu Lys Arg Gln Asn
            100                 105                 110

Phe Ala Asn Asp Leu Asn Gly Pro Gln Leu Ile Ala Val Thr Ala Ser
            115                 120                 125

Ser Asn Arg Ser Lys Gly Asp Gln Asp Pro Ser Thr Trp Gln Pro Thr
            130                 135                 140

Arg Thr Gly Ala Arg Cys Ala Tyr Ala Lys Met Trp Ile Asn Thr Lys
145                 150                 155                 160

Tyr Arg Trp Gly Leu His Leu Gln Ser Ser Glu Lys Ser Ala Leu Gln
                165                 170                 175

Ser Met Leu Asn Thr Cys Ser Tyr
            180

<210> SEQ ID NO 24
<211> LENGTH: 182
<212> TYPE: PRT
<213> ORGANISM: Bacillus marisflavi

<400> SEQUENCE: 24

Thr Pro Pro Val Thr Pro Ser Lys Glu Thr Ser Gln Ser Gln Leu Asn
1               5                  10                  15

Gly Leu Thr Val Lys Thr Glu Gly Ala Met Thr Gly Tyr Ser Arg Asp
            20                  25                  30

Lys Phe Pro His Trp Ser Ser Gln Gly Gly Gly Cys Asp Thr Arg Gln
            35                  40                  45

Val Val Leu Lys Arg Asp Ala Asp Ser Tyr Ser Gly Asn Cys Pro Val
        50                  55                  60

Thr Ser Gly Ser Trp Tyr Ser Tyr Asp Gly Val Lys Phe Thr His
 65                  70                  75                  80

Pro Ser Asp Leu Asp Ile Asp His Ile Val Pro Leu Ala Glu Ala Trp
                 85                  90                  95

Arg Ser Gly Ala Ser Ser Trp Thr Thr Ala Gln Arg Glu Ala Phe Ala
            100                 105                 110

Asn Asp Leu Ser Gly Ser Gln Leu Ile Ala Val Ser Ala Ser Ser Asn
            115                 120                 125

Arg Ser Lys Gly Asp Gln Asp Pro Ser Thr Trp Gln Pro Pro Arg Ala
        130                 135                 140

Gly Ala Lys Cys Gly Tyr Ala Lys Trp Trp Ile Ser Thr Lys Ser Lys
145                 150                 155                 160

Trp Asn Leu Ser Leu Gln Ser Ser Glu Lys Thr Ala Leu Gln Gly Met
                165                 170                 175

Leu Asn Ser Cys Val Tyr
            180

<210> SEQ ID NO 25
<211> LENGTH: 182
<212> TYPE: PRT
<213> ORGANISM: Bacillus sp. SA2-6

<400> SEQUENCE: 25

Leu Pro Ser Gly Ile Pro Ser Lys Ser Thr Ala Gln Ser Gln Leu Asn
1               5                  10                  15
```

Ser Leu Thr Val Lys Ser Glu Gly Ser Met Thr Gly Tyr Ser Arg Asp
            20                  25                  30

Lys Phe Pro His Trp Ile Ser Gln Gly Gly Cys Asp Thr Arg Gln
        35                  40                  45

Val Val Leu Lys Arg Asp Ala Asp Tyr Tyr Ser Gly Asn Cys Pro Val
 50                  55                  60

Thr Ser Gly Lys Trp Tyr Ser Tyr Tyr Asp Gly Ile Ser Val Tyr Ser
 65                  70                  75                  80

Pro Ser Glu Ile Asp Ile Asp His Val Val Pro Leu Ala Glu Ala Trp
                85                  90                  95

Arg Ser Gly Ala Ser Ser Trp Thr Thr Lys Arg Gln Asn Phe Ala
            100                 105                 110

Asn Asp Leu Asn Gly Pro Gln Leu Ile Ala Val Thr Ala Ser Val Asn
            115                 120                 125

Arg Ser Lys Gly Asp Gln Asp Pro Ser Thr Trp Gln Pro Pro Arg Tyr
 130                 135                 140

Gly Ala Arg Cys Ala Tyr Ala Lys Met Trp Ile Asn Thr Lys Tyr Arg
145                 150                 155                 160

Trp Asp Leu Asn Leu Gln Ser Ser Glu Lys Ser Ser Leu Gln Ser Met
                165                 170                 175

Leu Asp Thr Cys Ser Tyr
            180

<210> SEQ ID NO 26
<211> LENGTH: 191
<212> TYPE: PRT
<213> ORGANISM: Pyrenochaetopsis sp.

<400> SEQUENCE: 26

Leu Pro Ser Pro Leu Ile Ala Arg Ser Pro Pro Asn Ile Pro Ser
 1               5                   10                  15

Ala Thr Thr Ala Lys Thr Gln Leu Ala Gly Leu Thr Val Ala Pro Gln
                20                  25                  30

Gly Pro Gln Thr Gly Tyr Ser Arg Asp Leu Phe Pro His Trp Ile Thr
            35                  40                  45

Gln Ser Gly Thr Cys Asn Thr Arg Glu Val Val Leu Lys Arg Asp Gly
 50                  55                  60

Thr Asn Val Val Thr Asn Ser Ala Cys Ala Ser Thr Ser Gly Ser Trp
 65                  70                  75                  80

Leu Ser Pro Tyr Asp Gly Lys Thr Trp Asp Ser Ala Ser Asp Ile Gln
                85                  90                  95

Ile Asp His Leu Val Pro Leu Ser Asn Ala Trp Lys Ser Gly Ala Ala
            100                 105                 110

Ala Trp Thr Thr Ala Gln Arg Gln Ala Phe Ala Asn Asp Leu Thr His
        115                 120                 125

Pro Gln Leu Val Ala Val Thr Gly Ser Val Asn Glu Ser Lys Gly Asp
 130                 135                 140

Asp Gly Pro Glu Asp Trp Lys Pro Pro Leu Ala Ser Tyr Tyr Cys Thr
145                 150                 155                 160

Tyr Ala Ser Met Trp Thr Ala Val Lys Ser Asn Tyr Lys Leu Thr Ile
                165                 170                 175

Thr Ser Ala Glu Lys Ser Ala Leu Thr Ser Met Leu Ala Thr Cys
            180                 185                 190

```
<210> SEQ ID NO 27
<211> LENGTH: 190
<212> TYPE: PRT
<213> ORGANISM: Vibrissea flavovirens

<400> SEQUENCE: 27

Thr Pro Leu Pro Ile Ile Ala Arg Thr Pro Asn Ile Pro Thr Thr
1               5                   10                  15

Ala Thr Ala Lys Ser Gln Leu Ala Ala Leu Thr Val Ala Ala Gly
            20                  25                  30

Pro Gln Thr Gly Tyr Ser Arg Asp Leu Phe Pro Thr Trp Ile Thr Ile
        35                  40                  45

Ser Gly Thr Cys Asn Thr Arg Glu Thr Val Leu Lys Arg Asp Gly Thr
50                  55                  60

Asn Val Val Asp Ser Ala Cys Val Ala Thr Ser Gly Ser Trp Tyr
65                  70                  75                  80

Ser Pro Tyr Asp Gly Ala Thr Trp Ala Ala Ser Asp Val Asp Ile
                85                  90                  95

Asp His Met Val Pro Leu Ser Asn Ala Trp Lys Ser Gly Ala Ser Ala
                100                 105                 110

Trp Thr Thr Ala Gln Arg Gln Thr Phe Ala Asn Asp Leu Thr Asn Pro
                115                 120                 125

Gln Leu Leu Ala Val Thr Asp Asn Val Asn Gln Ala Lys Gly Asp Ser
130                 135                 140

Gly Pro Glu Asp Trp Lys Pro Ser Leu Thr Ser Tyr Trp Cys Thr Tyr
145                 150                 155                 160

Ala Lys Met Trp Val Lys Val Lys Thr Val Tyr Asp Leu Thr Ile Thr
                165                 170                 175

Ser Ala Glu Lys Thr Ala Leu Thr Thr Met Leu Asn Thr Cys
                180                 185                 190

<210> SEQ ID NO 28
<211> LENGTH: 192
<212> TYPE: PRT
<213> ORGANISM: Setosphaeria rostrata

<400> SEQUENCE: 28

Ala Pro Thr Ser Ser Pro Leu Val Ala Arg Ala Pro Asn Val Pro
1               5                   10                  15

Ser Lys Ala Glu Ala Thr Ser Gln Leu Ala Gly Leu Thr Val Ala Pro
            20                  25                  30

Gln Gly Pro Gln Thr Gly Tyr Ser Arg Asp Leu Phe Pro His Trp Ile
        35                  40                  45

Thr Gln Ser Gly Thr Cys Asn Thr Arg Glu Thr Val Leu Lys Arg Asp
50                  55                  60

Gly Thr Asn Val Val Thr Asn Ser Ala Cys Ala Ser Thr Ser Gly Ser
65                  70                  75                  80

Trp Phe Ser Pro Tyr Asp Gly Ala Thr Trp Thr Ala Ala Ser Asp Val
                85                  90                  95

Asp Ile Asp His Met Val Pro Leu Ser Asn Ala Trp Lys Ser Gly Ala
                100                 105                 110

Ala Ser Trp Thr Thr Ala Arg Arg Gln Ala Phe Ala Asn Asp Leu Thr
                115                 120                 125

Asn Pro Gln Leu Leu Ala Val Thr Asp Asn Val Asn Gln Ala Lys Gly
130                 135                 140
```

```
Asp Lys Gly Pro Glu Asp Trp Lys Pro Leu Thr Ser Tyr Tyr Cys
145                 150                 155                 160

Thr Tyr Ser Lys Met Trp Ile Lys Val Lys Ser Val Trp Gly Leu Thr
                165                 170                 175

Ile Thr Ser Ala Glu Lys Ser Ala Leu Thr Ser Met Leu Ala Thr Cys
            180                 185                 190
```

<210> SEQ ID NO 29
<211> LENGTH: 192
<212> TYPE: PRT
<213> ORGANISM: Endophragmiella valdina

<400> SEQUENCE: 29

```
Ala Pro Val Pro Gly His Leu Met Pro Arg Ala Pro Asn Val Pro
1               5                   10                  15

Thr Thr Ala Ala Ala Lys Thr Ala Leu Ala Gly Leu Thr Val Gln Ala
                20                  25                  30

Gln Gly Ser Gln Thr Gly Tyr Ser Arg Asp Leu Phe Pro His Trp Ile
            35                  40                  45

Thr Gln Ser Gly Thr Cys Asn Thr Arg Glu Val Val Leu Lys Arg Asp
50                  55                  60

Gly Thr Asn Val Val Thr Asp Ser Ala Cys Ala Ala Thr Ser Gly Thr
65                  70                  75                  80

Trp Val Ser Pro Tyr Asp Gly Ala Thr Trp Thr Ala Ala Ser Asp Val
                85                  90                  95

Asp Ile Asp His Met Val Pro Leu Ser Asn Ala Trp Lys Ser Gly Ala
            100                 105                 110

Ala Ser Trp Thr Thr Ala Gln Arg Gln Ala Phe Ala Asn Asp Leu Thr
        115                 120                 125

Asn Pro Gln Leu Leu Ala Val Thr Asp Asn Val Asn Gln Ser Lys Gly
130                 135                 140

Asp Lys Gly Pro Glu Asp Trp Lys Pro Leu Thr Ser Tyr Tyr Cys
145                 150                 155                 160

Thr Tyr Ala Lys Met Trp Val Lys Val Lys Ser Val Tyr Ser Leu Thr
                165                 170                 175

Ile Thr Ser Ala Glu Lys Thr Ala Leu Thr Ser Met Leu Asn Thr Cys
            180                 185                 190
```

<210> SEQ ID NO 30
<211> LENGTH: 190
<212> TYPE: PRT
<213> ORGANISM: Corynespora cassiicola

<400> SEQUENCE: 30

```
Leu

```
Asp His Met Val Pro Leu Ser Asn Ala Trp Lys Ser Gly Ala Ala Ser
            100                 105                 110

Trp Thr Thr Ser Arg Arg Gln Ala Phe Ala Asn Asp Leu Thr Asn Pro
        115                 120                 125

Gln Leu Ile Ala Val Thr Asp Asn Val Asn Gln Ser Lys Gly Asp Lys
130                 135                 140

Gly Pro Glu Asp Trp Lys Pro Pro Leu Thr Ser Tyr Tyr Cys Thr Tyr
145                 150                 155                 160

Ala Lys Met Trp Val Arg Val Lys Ser Val Tyr Ser Leu Thr Ile Thr
                165                 170                 175

Ser Ala Glu Lys Ser Ala Leu Thr Ser Met Leu Asp Thr Cys
            180                 185                 190

<210> SEQ ID NO 31
<211> LENGTH: 192
<212> TYPE: PRT
<213> ORGANISM: Paraphoma sp. XZ1965

<400> SEQUENCE: 31

Ala Pro Ala Pro Val His Leu Val Ala Arg Ala Pro Asn Val Pro
1               5                   10                  15

Thr Ala Ala Gln Ala Gln Thr Gln Leu Ala Gly Leu Thr Val Ala Ala
                20                  25                  30

Gln Gly Pro Gln Thr Gly Tyr Ser Arg Asp Leu Phe Pro His Trp Ile
            35                  40                  45

Thr Gln Ser Gly Ala Cys Asn Thr Arg Glu Thr Val Leu Lys Arg Asp
 50                 55                  60

Gly Thr Gly Val Val Gln Asp Ser Ala Cys Ala Ala Thr Ser Gly Thr
65                  70                  75                  80

Trp Lys Ser Pro Tyr Asp Gly Ala Thr Trp Thr Ala Ala Ser Asp Val
                85                  90                  95

Asp Ile Asp His Met Val Pro Leu Ser Asn Ala Trp Lys Ser Gly Ala
            100                 105                 110

Ala Ser Trp Thr Thr Ala Arg Arg Gln Ala Phe Ala Asn Asp Leu Thr
        115                 120                 125

Asn Pro Gln Leu Leu Ala Val Thr Asp Asn Val Asn Gln Ala Lys Gly
130                 135                 140

Asp Lys Gly Pro Glu Asp Trp Lys Pro Pro Leu Thr Ser Tyr Tyr Cys
145                 150                 155                 160

Ile Tyr Ala Arg Met Trp Ile Lys Val Lys Ser Val Tyr Ser Leu Thr
                165                 170                 175

Ile Thr Ser Ala Glu Lys Ser Ala Leu Thr Ser Met Leu Gly Thr Cys
            180                 185                 190

<210> SEQ ID NO 32
<211> LENGTH: 186
<212> TYPE: PRT
<213> ORGANISM: Monilinia fructicola

<400> SEQUENCE: 32

Thr Pro Val Pro Ala Pro Thr Gly Ile Pro Ser Thr Ser Val Ala Asn
1               5                   10                  15

Thr Gln Leu Ala Ala Leu Thr Val Ala Ala Gly Ser Gln Asp Gly
                20                  25                  30

Tyr Ser Arg Asp Leu Phe Pro His Trp Ile Thr Ile Ser Gly Ala Cys
            35                  40                  45
```

```
Asn Thr Arg Glu Thr Val Leu Lys Arg Asp Gly Thr Asn Val Val Val
     50                  55                  60

Asn Ser Ala Cys Ala Ala Thr Ser Gly Thr Trp Val Ser Pro Tyr Asp
65                  70                  75                  80

Gly Ala Thr Trp Thr Ala Ala Ser Asp Val Asp Ile Asp His Leu Val
                     85                  90                  95

Pro Leu Ser Asn Ala Trp Lys Ala Gly Ala Ser Ser Trp Thr Thr Ala
                100                 105                 110

Gln Arg Gln Ala Phe Ala Asn Asp Leu Val Asn Pro Gln Leu Leu Ala
            115                 120                 125

Val Thr Asp Ser Val Asn Gln Gly Lys Ser Asp Ser Gly Pro Glu Ala
    130                 135                 140

Trp Lys Pro Ser Leu Lys Ser Tyr Trp Cys Thr Tyr Ala Lys Met Trp
145                 150                 155                 160

Ile Lys Val Lys Tyr Val Tyr Asp Leu Thr Ile Thr Ser Ala Glu Lys
                165                 170                 175

Ser Ala Leu Val Thr Met Met Asp Thr Cys
            180                 185

<210> SEQ ID NO 33
<211> LENGTH: 190
<212> TYPE: PRT
<213> ORGANISM: Curvularia lunata

<400> SEQUENCE: 33

Ala Pro Ala Pro Leu Ser Ala Arg Ala Pro Asn Ile Pro Ser Lys
1               5                   10                  15

Ala Asp Ala Thr Ser Gln Leu Ala Gly Leu Thr Val Ala Ala Gln Gly
                20                  25                  30

Pro Gln Thr Gly Tyr Ser Arg Asp Leu Phe Pro His Trp Ile Thr Gln
            35                  40                  45

Ser Gly Thr Cys Asn Thr Arg Glu Thr Val Leu Lys Arg Asp Gly Thr
    50                  55                  60

Asn Val Val Thr Ser Ser Cys Ala Ala Thr Ser Gly Thr Trp Phe
65                  70                  75                  80

Ser Pro Tyr Asp Gly Ala Thr Trp Thr Ala Ala Ser Asp Val Asp Ile
                85                  90                  95

Asp His Val Val Pro Leu Ser Asn Ala Trp Lys Ser Gly Ala Ala Ser
                100                 105                 110

Trp Thr Thr Ala Arg Arg Gln Ala Phe Ala Asn Asp Leu Thr Asn Pro
            115                 120                 125

Gln Leu Ile Ala Val Thr Asp Ser Val Asn Gln Ala Lys Gly Asp Lys
    130                 135                 140

Gly Pro Glu Asp Trp Lys Pro Pro Leu Ser Ser Tyr Tyr Cys Thr Tyr
145                 150                 155                 160

Ser Lys Met Trp Ile Lys Val Lys Ser Val Tyr Gly Leu Thr Val Thr
                165                 170                 175

Ser Ala Glu Lys Ser Ala Leu Ser Ser Met Leu Ala Thr Cys
            180                 185                 190

<210> SEQ ID NO 34
<211> LENGTH: 191
<212> TYPE: PRT
<213> ORGANISM: Penicillium reticulisporum
```

<400> SEQUENCE: 34

Leu Pro Ala Pro Glu Ala Leu Pro Ala Pro Gly Val Pro Ser Ala
1               5                   10                  15

Ser Thr Ala Gln Ser Glu Leu Ala Ala Leu Thr Val Ala Ala Gln Gly
            20                  25                  30

Ser Gln Asp Gly Tyr Ser Arg Ser Lys Phe Pro His Trp Ile Thr Gln
            35                  40                  45

Ser Gly Ser Cys Asp Thr Arg Asp Val Val Leu Lys Arg Asp Gly Thr
        50                  55                  60

Asn Val Val Gln Ser Ala Ser Gly Cys Thr Ile Thr Ser Gly Lys Trp
65                  70                  75                  80

Val Ser Pro Tyr Asp Gly Ala Thr Trp Thr Ala Ser Ser Asp Val Asp
                85                  90                  95

Ile Asp His Leu Val Pro Leu Ser Asn Ala Trp Lys Ser Gly Ala Ser
                100                 105                 110

Gly Trp Thr Thr Ala Ala Arg Gln Ala Phe Ala Asn Asp Leu Thr Asn
                115                 120                 125

Pro Gln Leu Leu Val Val Thr Asp Asn Val Asn Glu Ser Lys Gly Asp
            130                 135                 140

Lys Gly Pro Glu Glu Trp Lys Pro Pro Leu Thr Ser Tyr Tyr Cys Thr
145                 150                 155                 160

Tyr Ala Glu Met Trp Val Lys Val Lys Ser Val Tyr Lys Leu Thr Ile
                165                 170                 175

Thr Ser Ala Glu Lys Ser Ala Leu Thr Ser Met Leu Ser Thr Cys
            180                 185                 190

<210> SEQ ID NO 35
<211> LENGTH: 191
<212> TYPE: PRT
<213> ORGANISM: Penicillium quercetorum

<400> SEQUENCE: 35

Leu Pro Ala Pro Glu Pro Ala Pro Ser Pro Gly Ile Pro Ser Ala
1               5                   10                  15

Ser Thr Ala Arg Ser Glu Leu Ala Ser Leu Thr Val Ala Pro Gln Gly
            20                  25                  30

Ser Gln Asp Gly Tyr Ser Arg Ala Lys Phe Pro His Trp Ile Lys Gln
            35                  40                  45

Ser Gly Ser Cys Asp Thr Arg Asp Val Val Leu Glu Arg Asp Gly Thr
        50                  55                  60

Asn Val Val Gln Ser Ser Thr Gly Cys Thr Ile Thr Gly Gly Thr Trp
65                  70                  75                  80

Val Ser Pro Tyr Asp Gly Ala Thr Trp Thr Ala Ser Ser Asp Val Asp
                85                  90                  95

Ile Asp His Leu Val Pro Leu Ser Asn Ala Trp Lys Ser Gly Ala Ser
                100                 105                 110

Ala Trp Thr Thr Ala Gln Arg Gln Ala Phe Ala Asn Asp Leu Thr Asn
                115                 120                 125

Pro Gln Leu Val Ala Val Thr Asp Asn Val Asn Glu Ala Lys Gly Asp
            130                 135                 140

Lys Gly Pro Glu Glu Trp Lys Pro Pro Leu Thr Ser Tyr Tyr Cys Thr
145                 150                 155                 160

Tyr Ala Glu Met Trp Val Lys Val Lys Ser Val Tyr Lys Leu Thr Ile
                165                 170                 175

```
Thr Ser Ala Glu Lys Ser Ala Leu Ser Ser Met Leu Asn Thr Cys
            180                 185                 190

<210> SEQ ID NO 36
<211> LENGTH: 192
<212> TYPE: PRT
<213> ORGANISM: Setophaeosphaeria sp.

<400> SEQUENCE: 36

Leu Pro Ala Pro Val Thr Leu Glu Ala Arg Ala Pro Asn Ile Pro
1               5                   10                  15

Ser Thr Ala Ser Ala Asn Thr Leu Leu Ala Gly Leu Thr Val Ala Ala
            20                  25                  30

Gln Gly Ser Gln Thr Gly Tyr Ser Arg Asp Leu Phe Pro His Trp Ile
            35                  40                  45

Thr Gln Ser Gly Thr Cys Asn Thr Arg Glu Thr Val Leu Lys Arg Asp
        50                  55                  60

Gly Thr Gly Val Val Thr Asp Ser Ala Cys Ala Ser Thr Ser Gly Ser
65                  70                  75                  80

Trp Tyr Ser Val Tyr Asp Gly Ala Thr Trp Thr Ala Ala Ser Asp Val
                85                  90                  95

Asp Ile Asp His Val Val Pro Leu Ser Asn Ala Trp Lys Ser Gly Ala
            100                 105                 110

Ala Ser Trp Thr Thr Ala Arg Arg Gln Ser Phe Ala Asn Asp Leu Thr
            115                 120                 125

Asn Pro Gln Leu Ile Ala Val Thr Asp Asn Val Asn Gln Ala Lys Gly
        130                 135                 140

Asp Lys Gly Pro Glu Asp Trp Lys Pro Pro Leu Thr Ser Tyr Tyr Cys
145                 150                 155                 160

Thr Tyr Ala Lys Met Trp Val Lys Val Lys Ser Val Tyr Ser Leu Thr
                165                 170                 175

Ile Thr Ser Ala Glu Lys Thr Ala Leu Thr Ser Met Leu Asn Thr Cys
            180                 185                 190

<210> SEQ ID NO 37
<211> LENGTH: 192
<212> TYPE: PRT
<213> ORGANISM: Alternaria sp. XZ2545

<400> SEQUENCE: 37

Leu Pro Ala Pro Val Thr Leu Glu Ala Arg Ala Pro Asn Ile Pro
1               5                   10                  15

Thr Thr Ala Ala Ala Lys Thr Gln Leu Ala Gly Leu Thr Val Ala Ala
            20                  25                  30

Gln Gly Pro Gln Thr Gly Tyr Ser Arg Asp Leu Phe Pro His Trp Ile
            35                  40                  45

Thr Gln Ser Gly Thr Cys Asn Thr Arg Glu Thr Val Leu Lys Arg Asp
        50                  55                  60

Gly Thr Gly Val Val Thr Asp Ser Ala Cys Ala Ser Thr Ser Gly Ser
65                  70                  75                  80

Trp Phe Ser Val Tyr Asp Gly Ala Thr Trp Thr Ala Ala Ser Asp Val
                85                  90                  95

Asp Ile Asp His Val Val Pro Leu Ser Asn Ala Trp Lys Ser Gly Ala
            100                 105                 110

Ala Ser Trp Thr Thr Ala Arg Arg Gln Ser Phe Ala Asn Asp Leu Thr
            115                 120                 125
```

Asn Pro Gln Leu Ile Ala Val Thr Asp Asn Val Asn Gln Ala Lys Gly
            130                 135                 140

Asp Lys Gly Pro Glu Asp Trp Lys Pro Pro Leu Thr Ser Tyr Tyr Cys
145                 150                 155                 160

Thr Tyr Ala Lys Met Trp Val Lys Val Lys Ser Val Tyr Ala Leu Thr
                165                 170                 175

Ile Thr Ser Ala Glu Lys Thr Ala Leu Thr Ser Met Leu Asn Thr Cys
            180                 185                 190

<210> SEQ ID NO 38
<211> LENGTH: 192
<212> TYPE: PRT
<213> ORGANISM: Alternaria sp.

<400> SEQUENCE: 38

Leu Pro Ala Pro Val Thr Leu Glu Ala Arg Ala Pro Pro Asn Ile Pro
1               5                   10                  15

Thr Thr Ala Ala Ala Lys Thr Gln Leu Ala Gly Leu Thr Val Ala Ala
            20                  25                  30

Gln Gly Pro Gln Thr Gly Tyr Ser Arg Asp Leu Phe Pro His Trp Ile
        35                  40                  45

Thr Gln Ser Gly Ser Cys Asn Thr Arg Glu Val Val Leu Gln Arg Asp
    50                  55                  60

Gly Thr Gly Val Val Thr Asp Ser Ala Cys Ala Thr Ser Gly Ser
65                  70                  75                  80

Trp Tyr Ser Val Tyr Asp Gly Ala Thr Trp Thr Ala Ala Ser Asp Val
                85                  90                  95

Asp Ile Asp His Met Val Pro Leu Ser Asn Ala Trp Lys Ser Gly Ala
            100                 105                 110

Ala Ser Trp Thr Thr Ala Arg Arg Gln Ala Phe Ala Asn Asp Leu Thr
        115                 120                 125

Asn Pro Gln Leu Leu Ala Val Thr Asp Asn Val Asn Gln Ala Lys Gly
    130                 135                 140

Asp Lys Gly Pro Glu Asp Trp Lys Pro Pro Leu Thr Ser Tyr Tyr Cys
145                 150                 155                 160

Thr Tyr Ala Lys Met Trp Val Lys Val Lys Ser Val Tyr Ala Leu Thr
                165                 170                 175

Ile Thr Ser Ala Glu Lys Thr Ala Leu Thr Ser Met Leu Asn Thr Cys
            180                 185                 190

<210> SEQ ID NO 39
<211> LENGTH: 186
<212> TYPE: PRT
<213> ORGANISM: Trichoderma reesei

<400> SEQUENCE: 39

Ala Pro Leu Pro Ala Pro Pro Gly Ile Pro Ser Glu Asp Thr Ala Arg
1               5                   10                  15

Thr Gln Leu Ala Gly Leu Thr Val Ala Val Val Gly Ser Gly Thr Gly
            20                  25                  30

Tyr Ser Arg Asp Leu Phe Pro Thr Trp Asp Ala Ile Ser Gly Asn Cys
        35                  40                  45

Asn Ala Arg Glu Tyr Val Leu Lys Arg Asp Gly Glu Gly Val Gln Val
    50                  55                  60

Asn Asn Ala Cys Glu Ala Gln Ser Gly Ser Trp Ile Ser Pro Tyr Asp
65                  70                  75                  80

```
Asn Ala Ser Phe Thr Asn Ala Ser Ser Leu Asp Ile Asp His Met Val
                85                  90                  95

Pro Leu Lys Asn Ala Trp Ile Ser Gly Ala Ser Thr Trp Thr Thr Ala
            100                 105                 110

Gln Arg Glu Ala Leu Ala Asn Asp Val Ser Arg Pro Gln Leu Trp Ala
        115                 120                 125

Val Ser Ala Ser Ser Asn Arg Ser Lys Gly Asp Arg Ser Pro Asp Gln
    130                 135                 140

Trp Lys Pro Pro Leu Thr Ser Phe Tyr Cys Thr Tyr Ala Lys Ser Trp
145                 150                 155                 160

Ile Asp Val Lys Ser Tyr Tyr Lys Leu Thr Ile Thr Ser Ala Glu Lys
                165                 170                 175

Thr Ala Leu Ser Ser Met Leu Asp Thr Cys
                180                 185

<210> SEQ ID NO 40
<211> LENGTH: 188
<212> TYPE: PRT
<213> ORGANISM: Chaetomium thermophilum

<400> SEQUENCE: 40

Ala Pro Ala Pro Gln Pro Thr Pro Pro Gly Ile Pro Ser Arg Ser Thr
1               5                   10                  15

Ala Gln Ser Tyr Leu Asn Ser Leu Thr Val Ala Ala Ser Tyr Asp Asp
            20                  25                  30

Gly Asn Tyr Asn Arg Asp Leu Phe Pro His Trp Asn Thr Val Ser Gly
        35                  40                  45

Thr Cys Asn Thr Arg Glu Tyr Val Leu Lys Arg Asp Gly Ser Asn Val
    50                  55                  60

Val Thr Asn Ser Ala Cys Gln Ala Thr Ser Gly Thr Trp Tyr Ser Pro
65                  70                  75                  80

Tyr Asp Gly Ala Thr Trp Thr Ala Ala Ser Asp Ile Asp Ile Asp His
                85                  90                  95

Met Val Pro Leu Lys Asn Ala Trp Ile Ser Gly Ala Asn Thr Trp Ser
            100                 105                 110

Ser Ser Lys Arg Ser Ser Phe Ala Asn Asp Ile Asn Ser Pro Gln Leu
        115                 120                 125

Trp Ala Val Thr Asp Ser Val Asn Gln Ser Lys Gly Asp Lys Ser Pro
    130                 135                 140

Asp Lys Trp Lys Pro Pro Leu Thr Thr Phe Tyr Cys Thr Tyr Ala Lys
145                 150                 155                 160

Ser Trp Ile Thr Val Lys Tyr Asn Tyr Asn Leu Thr Ile Thr Ser Ala
                165                 170                 175

Glu Lys Ser Ala Leu Gln Asn Met Ile Asn Thr Cys
            180                 185

<210> SEQ ID NO 41
<211> LENGTH: 190
<212> TYPE: PRT
<213> ORGANISM: Scytalidium thermophilum

<400> SEQUENCE: 41

Leu Pro Ala Pro Ala Pro Met Pro Thr Pro Pro Gly Ile Pro Ser Lys
1               5                   10                  15

Ser Thr Ala Gln Ser Gln Leu Asn Ala Leu Thr Val Lys Ala Ser Tyr
            20                  25                  30
```

```
Asp Asp Gly Lys Tyr Lys Arg Asp Leu Phe Pro His Trp Asn Thr Val
            35                  40                  45

Ser Gly Thr Cys Asn Thr Arg Glu Tyr Val Leu Lys Arg Asp Gly Val
 50                  55                  60

Asn Val Val Thr Asn Ser Ala Cys Ala Ala Thr Ser Gly Thr Trp Tyr
 65                  70                  75                  80

Ser Pro Phe Asp Gly Ala Thr Trp Thr Ala Ala Ser Asp Val Asp Ile
                 85                  90                  95

Asp His Met Val Pro Leu Lys Asn Ala Trp Ile Ser Gly Ala Asn Asn
                100                 105                 110

Trp Thr Ser Thr Lys Arg Thr Gln Phe Ala Asn Asp Ile Asn Leu Pro
            115                 120                 125

Gln Leu Trp Ala Val Thr Asp Asp Val Asn Gln Ala Lys Gly Asp Lys
130                 135                 140

Ser Pro Asp Lys Trp Lys Pro Pro Leu Thr Ser Phe Tyr Cys Thr Tyr
145                 150                 155                 160

Ala Lys Ser Trp Ile Thr Val Lys Tyr Asn Tyr Gly Leu Ser Ile Thr
                165                 170                 175

Ser Ala Glu Lys Ser Ala Leu Thr Ser Met Ile Asn Thr Cys
            180                 185                 190

<210> SEQ ID NO 42
<211> LENGTH: 186
<212> TYPE: PRT
<213> ORGANISM: Metapochonia suchlasporia

<400> SEQUENCE: 42

Val Pro Val Pro Ala Pro Pro Gly Ile Pro Ser Thr Ser Thr Ala Lys
1               5                   10                  15

Thr Leu Leu Ala Gly Leu Lys Val Ala Val Pro Leu Ser Gly Asp Gly
            20                  25                  30

Tyr Ser Arg Glu Lys Phe Pro Leu Trp Glu Thr Ile Gln Gly Thr Cys
        35                  40                  45

Asn Ala Arg Glu Phe Val Leu Lys Arg Asp Gly Thr Asp Val Lys Thr
 50                  55                  60

Asn Asn Ala Cys Val Ala Glu Ser Gly Asn Trp Val Ser Pro Tyr Asp
 65                  70                  75                  80

Gly Val Lys Phe Thr Ala Ala Arg Asp Leu Asp Ile Asp His Met Val
                 85                  90                  95

Pro Leu Lys Asn Ala Trp Ile Ser Gly Ala Ser Gln Trp Thr Thr Glu
                100                 105                 110

Arg Arg Lys Ala Leu Ala Asn Asp Ile Thr Arg Pro Gln Leu Trp Ala
            115                 120                 125

Val Ser Ala His Ala Asn Arg Gly Lys Ser Asp Asp Ser Pro Asp Glu
130                 135                 140

Trp Lys Pro Pro Leu Lys Thr Phe Trp Cys Thr Tyr Ala Lys Ser Trp
145                 150                 155                 160

Val Gln Val Lys Ser Phe Tyr Glu Leu Thr Ile Thr Asp Ala Glu Lys
                165                 170                 175

Gly Ala Leu Ala Gly Met Leu Asp Ser Cys
            180                 185

<210> SEQ ID NO 43
<211> LENGTH: 198
<212> TYPE: PRT
```

<213> ORGANISM: Daldinia fissa

<400> SEQUENCE: 43

Ala Pro Ala Pro Ile Pro Val Ala Glu Pro Ala Met Pro Met Pro
1               5                   10                  15

Thr Pro Pro Gly Ile Pro Ser Ala Ser Ser Ala Lys Ser Gln Leu Ala
            20                  25                  30

Ser Leu Thr Val Lys Ala Ala Val Asp Asp Gly Gly Tyr Gln Arg Asp
            35                  40                  45

Leu Phe Pro Thr Trp Asp Thr Ile Thr Gly Thr Cys Asn Thr Arg Glu
        50                  55                  60

Tyr Val Leu Lys Arg Asp Gly Ala Asn Val Gln Val Gly Ser Asp Cys
65                  70                  75                  80

Tyr Pro Thr Ser Gly Thr Trp Thr Ser Pro Tyr Asp Gly Gly Lys Trp
                85                  90                  95

Thr Ser Pro Ser Asp Val Asp Ile Asp His Met Val Pro Leu Lys Asn
            100                 105                 110

Ala Trp Val Ser Gly Ala Asn Lys Trp Thr Thr Ala Lys Arg Glu Gln
        115                 120                 125

Phe Ala Asn Asp Val Asp Arg Pro Gln Leu Trp Ala Val Thr Asp Asn
    130                 135                 140

Val Asn Ser Ser Lys Gly Asp Lys Ser Pro Asp Thr Trp Lys Pro Pro
145                 150                 155                 160

Leu Thr Ser Phe Tyr Cys Thr Tyr Ala Ser Ala Tyr Val Ala Val Lys
                165                 170                 175

Ser Tyr Trp Gly Leu Thr Ile Thr Ser Ala Glu Lys Ser Ala Leu Ser
            180                 185                 190

Asp Met Leu Gly Thr Cys
        195

<210> SEQ ID NO 44
<211> LENGTH: 188
<212> TYPE: PRT
<213> ORGANISM: Acremonium sp. XZ2007

<400> SEQUENCE: 44

Leu Pro Leu Gln Ser Arg Asp Pro Pro Gly Ile Pro Ser Thr Ala Thr
1               5                   10                  15

Ala Lys Ser Leu Leu Asn Gly Leu Thr Val Lys Ala Trp Ser Asn Glu
            20                  25                  30

Gly Thr Tyr Asp Arg Asp Leu Phe Pro His Trp Gln Thr Ile Glu Gly
            35                  40                  45

Thr Cys Asn Ala Arg Glu Tyr Val Leu Lys Arg Asp Gly Gln Asn Val
        50                  55                  60

Val Val Asn Ser Ala Cys Thr Ala Gln Ser Gly Thr Trp Lys Ser Val
65                  70                  75                  80

Tyr Asp Gly Glu Thr Thr Asn Ser Ala Ser Asp Leu Asp Ile Asp His
                85                  90                  95

Met Ile Pro Leu Lys Asn Ala Trp Ile Ser Gly Ala Ala Thr Trp Thr
            100                 105                 110

Thr Ala Gln Arg Thr Ser Phe Ala Asn Asp Ile Ser Ser Pro Gln Leu
        115                 120                 125

Trp Ala Val Thr Ala Gly Val Asn Arg Ser Lys Ser Asp Arg Ser Pro
    130                 135                 140

```
Asp Thr Trp Val Pro Pro Leu Ala Ser Phe His Cys Thr Tyr Gly Lys
145                 150                 155                 160

Ala Trp Val Gln Val Lys Ser Lys Trp Ala Leu Ser Ile Thr Ser Ala
            165                 170                 175

Glu Lys Ser Ala Leu Thr Gly Leu Leu Asn Lys Cys
        180                 185
```

<210> SEQ ID NO 45
<211> LENGTH: 182
<212> TYPE: PRT
<213> ORGANISM: Acremonium dichromosporum

<400> SEQUENCE: 45

```
Ile Pro Pro Gly Ile Pro Ser Glu Ala Thr Ala Arg Ser Leu Leu Ser
1               5                   10                  15

Ser Leu Thr Val Ala Pro Thr Val Asp Asp Gly Thr Tyr Asp Arg Asp
            20                  25                  30

Leu Phe Pro His Trp Ser Ser Val Glu Gly Asn Cys Asn Ala Arg Glu
        35                  40                  45

Phe Val Leu Arg Arg Asp Gly Asp Gly Val Ser Val Gly Asn Asp Cys
50                  55                  60

Tyr Pro Thr Ala Gly Thr Trp Thr Cys Pro Tyr Asp Gly Lys Arg His
65                  70                  75                  80

Ser Val Pro Ser Asp Val Ser Ile Asp His Met Val Pro Leu His Asn
                85                  90                  95

Ala Trp Met Thr Gly Ala Ser Glu Trp Thr Thr Ala Glu Arg Glu Ala
            100                 105                 110

Phe Ala Asn Asp Ile Asp Gly Pro Gln Leu Trp Ala Val Thr Ser Thr
        115                 120                 125

Thr Asn Ser Gln Lys Gly Ser Asp Ala Pro Asp Glu Trp Gln Pro Pro
130                 135                 140

Gln Thr Ser Ile His Cys Lys Tyr Ala Ala Ala Trp Ile Gln Val Lys
145                 150                 155                 160

Ser Thr Tyr Asp Leu Thr Val Ser Ser Ala Glu Gln Ala Ala Leu Glu
                165                 170                 175

Glu Met Leu Gly Arg Cys
            180
```

<210> SEQ ID NO 46
<211> LENGTH: 188
<212> TYPE: PRT
<213> ORGANISM: Sarocladium sp. XZ2014

<400> SEQUENCE: 46

```
Val Pro Ile Pro Leu Pro Asp Pro Pro Gly Ile Pro Ser Ser Ser Thr
1               5                   10                  15

Ala Asn Thr Leu Leu Ala Gly Leu Thr Val Arg Ala Ser Ser Asn Glu
            20                  25                  30

Asp Thr Tyr Asn Arg Asp Leu Phe Pro His Trp Val Ala Ile Ser Gly
        35                  40                  45

Asn Cys Asn Ala Arg Glu Tyr Val Leu Arg Arg Asp Gly Thr Asn Val
50                  55                  60

Val Val Asn Thr Ala Cys Val Pro Gln Ser Gly Thr Trp Arg Ser Pro
65                  70                  75                  80

Tyr Asp Gly Glu Ser Thr Thr Asn Ala Ser Asp Leu Asp Ile Asp His
                85                  90                  95
```

```
Met Val Pro Leu Lys Asn Ala Trp Ile Ser Gly Ala Ala Ser Trp Thr
            100                 105                 110

Thr Ala Lys Arg Gln Asp Phe Ala Asn Asp Val Ser Gly Pro Gln Leu
            115                 120                 125

Trp Ala Val Thr Ala Gly Val Asn Arg Ser Lys Gly Asp Lys Ser Pro
130                 135                 140

Asp Ser Trp Val Pro Pro Leu Ala Ser Phe His Cys Thr Tyr Ala Arg
145                 150                 155                 160

Ser Trp Ile Gln Val Lys Ser Ser Trp Ala Leu Ser Val Thr Ser Ala
                165                 170                 175

Glu Lys Ala Ala Leu Thr Asp Leu Leu Ser Thr Cys
            180                 185
```

<210> SEQ ID NO 47
<211> LENGTH: 186
<212> TYPE: PRT
<213> ORGANISM: Metarhizium sp. HNA15-2

<400> SEQUENCE: 47

```
Val Pro Val Pro Ala Pro Pro Gly Ile Pro Thr Ala Ser Thr Ala Arg
1               5                   10                  15

Thr Leu Leu Ala Gly Leu Lys Val Ala Thr Pro Leu Ser Gly Asp Gly
            20                  25                  30

Tyr Ser Arg Thr Leu Phe Pro Thr Trp Glu Thr Ile Glu Gly Thr Cys
        35                  40                  45

Asn Ala Arg Glu Phe Val Leu Lys Arg Asp Gly Thr Asp Val Gln Thr
    50                  55                  60

Asn Thr Ala Cys Val Ala Gln Ser Gly Asn Trp Val Ser Pro Tyr Asp
65                  70                  75                  80

Gly Val Ala Phe Thr Ala Ala Ser Asp Leu Asp Ile Asp His Met Val
                85                  90                  95

Pro Leu Lys Asn Ala Trp Ile Ser Gly Ala Ser Gln Trp Thr Thr Asp
            100                 105                 110

Lys Arg Lys Gly Leu Ala Asn Asp Ile Thr Arg Pro Gln Leu Trp Ala
            115                 120                 125

Val Ser Ala His Ala Asn Arg Ala Lys Gly Asp Ser Ser Pro Asp Glu
130                 135                 140

Trp Lys Pro Pro Leu Lys Thr Phe Trp Cys Thr Tyr Ala Arg Ser Trp
145                 150                 155                 160

Val Gln Val Lys Ser Tyr Tyr Ala Leu Thr Ile Thr Asp Ala Glu Lys
                165                 170                 175

Gly Ala Leu Ser Gly Met Leu Asp Ser Cys
            180                 185
```

<210> SEQ ID NO 48
<211> LENGTH: 188
<212> TYPE: PRT
<213> ORGANISM: Acremonium sp. XZ2414

<400> SEQUENCE: 48

```
Ala Pro Ile Ala Val Arg Asp Pro Gly Ile Pro Ser Ala Ser Thr
1               5                   10                  15

Ala Asn Thr Leu Leu Ala Gly Leu Thr Val Arg Ala Ser Ser Asn Glu
            20                  25                  30

Asp Ser Tyr Asp Arg Asn Leu Phe Pro His Trp Ser Ala Ile Ser Gly
        35                  40                  45
```

```
Asn Cys Asn Ala Arg Glu Phe Val Leu Glu Arg Asp Gly Thr Asn Val
         50                  55                  60

Val Val Asn Asn Ala Cys Val Ala Gln Ser Gly Thr Trp Arg Ser Pro
 65                  70                  75                  80

Tyr Asp Gly Glu Thr Thr Gly Asn Ala Ser Asp Leu Asp Ile Asp His
                 85                  90                  95

Met Val Pro Leu Lys Asn Ala Trp Ile Ser Gly Ala Ser Ser Trp Ser
                100                 105                 110

Thr Thr Arg Arg Gln Glu Phe Ala Asn Asp Val Ser Gly Pro Gln Leu
            115                 120                 125

Trp Ala Val Thr Ala Gly Val Asn Arg Ser Lys Gly Asp Arg Ser Pro
        130                 135                 140

Asp Ser Trp Val Pro Pro Leu Ala Ser Phe His Cys Thr Tyr Ala Lys
145                 150                 155                 160

Ser Trp Val Gln Val Lys Ser Ser Trp Ser Leu Ser Val Thr Ser Ala
                165                 170                 175

Glu Lys Ala Ala Leu Ser Asp Leu Leu Gly Thr Cys
                180                 185

<210> SEQ ID NO 49
<211> LENGTH: 186
<212> TYPE: PRT
<213> ORGANISM: Isaria tenuipes

<400> SEQUENCE: 49

Ala Pro Val Pro Glu Pro Pro Gly Ile Pro Ser Thr Ser Thr Ala Gln
 1               5                  10                  15

Ser Asp Leu Asn Ser Leu Gln Val Ala Ala Ser Gly Ser Gly Asp Gly
            20                  25                  30

Tyr Ser Arg Ala Glu Phe Pro His Trp Val Ser Val Glu Gly Ser Cys
        35                  40                  45

Asp Ser Arg Glu Tyr Val Leu Lys Arg Asp Gly Gln Asp Val Gln Ala
 50                  55                  60

Asp Ser Ser Cys Lys Ile Thr Ser Gly Thr Trp Val Ser Pro Tyr Asp
 65                  70                  75                  80

Ala Thr Thr Trp Thr Asn Ser Ser Lys Val Asp Ile Asp His Leu Val
                 85                  90                  95

Pro Leu Lys Asn Ala Trp Ile Ser Gly Ala Ser Ser Trp Thr Lys Ala
                100                 105                 110

Gln Arg Gln Asp Phe Ala Asn Asp Ile Lys Arg Pro Gln Leu Tyr Ala
            115                 120                 125

Val Ser Glu Asn Ala Asn Arg Ser Lys Gly Asp Arg Ser Pro Asp Gly
        130                 135                 140

Trp Lys Pro Pro Leu Lys Ser Phe Tyr Cys Thr Tyr Ala Lys Ser Trp
145                 150                 155                 160

Val Ala Val Lys Ser Tyr Tyr Lys Leu Thr Ile Thr Ser Ala Glu Lys
                165                 170                 175

Ser Ala Leu Gly Asp Met Leu Asp Thr Cys
                180                 185

<210> SEQ ID NO 50
<211> LENGTH: 184
<212> TYPE: PRT
<213> ORGANISM: Scytalidium circinatum
```

<400> SEQUENCE: 50

```
Ala Pro Pro Gly Ile Pro Ser Ala Ser Thr Ala Ser Ser Leu Leu Gly
1               5                   10                  15

Glu Leu Ala Val Ala Glu Pro Val Asp Asp Gly Ser Tyr Asp Arg Asp
            20                  25                  30

Leu Phe Pro His Trp Glu Pro Ile Pro Gly Glu Thr Ala Cys Ser Ala
        35                  40                  45

Arg Glu Tyr Val Leu Arg Arg Asp Gly Thr Gly Val Glu Thr Gly Ser
    50                  55                  60

Asp Cys Tyr Pro Thr Ser Gly Thr Trp Ser Ser Pro Tyr Asp Gly Gly
65                  70                  75                  80

Ser Trp Thr Ala Pro Ser Asp Val Asp Ile Asp His Met Val Pro Leu
                85                  90                  95

Lys Asn Ala Trp Ile Ser Gly Ala Ser Glu Trp Thr Thr Ala Glu Arg
            100                 105                 110

Glu Ala Phe Ala Asn Asp Ile Asp Gly Pro Gln Leu Trp Ala Val Thr
        115                 120                 125

Asp Glu Val Asn Gln Ser Lys Ser Asp Gln Ser Pro Asp Glu Trp Lys
    130                 135                 140

Pro Pro Leu Ser Ser Phe Tyr Cys Thr Tyr Ala Cys Ala Trp Ile Gln
145                 150                 155                 160

Val Lys Ser Thr Tyr Ser Leu Ser Ile Ser Ser Ala Glu Gln Ala Ala
                165                 170                 175

Leu Glu Asp Met Leu Gly Ser Cys
            180
```

<210> SEQ ID NO 51
<211> LENGTH: 186
<212> TYPE: PRT
<213> ORGANISM: Metarhizium lepidiotae

<400> SEQUENCE: 51

```
Val Pro Val Pro Ala Pro Pro Gly Ile Pro Thr Ala Ser Thr Ala Arg
1               5                   10                  15

Thr Leu Leu Ala Gly Leu Lys Val Ala Thr Pro Leu Ser Gly Asp Gly
            20                  25                  30

Tyr Ser Arg Thr Leu Phe Pro Trp Glu Thr Ile Glu Gly Thr Cys
        35                  40                  45

Asn Ala Arg Glu Phe Val Leu Lys Arg Asp Gly Thr Asp Val Gln Thr
    50                  55                  60

Asn Thr Ala Cys Val Ala Glu Ser Gly Asn Trp Val Ser Pro Tyr Asp
65                  70                  75                  80

Gly Val Ser Phe Thr Ala Ala Ser Asp Leu Asp Ile Asp His Met Val
                85                  90                  95

Pro Leu Lys Asn Ala Trp Ile Ser Gly Ala Ser Gln Trp Thr Thr Asp
            100                 105                 110

Lys Arg Lys Asp Leu Ala Asn Asp Ile Thr Arg Pro Gln Leu Trp Ala
        115                 120                 125

Val Ser Ala His Ala Asn Arg Ser Lys Gly Asp Ser Ser Pro Asp Glu
    130                 135                 140

Trp Lys Pro Pro Leu Gln Thr Phe Trp Cys Thr Tyr Ser Lys Ser Trp
145                 150                 155                 160

Ile Gln Val Lys Ser His Tyr Ser Leu Thr Ile Thr Asp Ala Glu Lys
                165                 170                 175
```

```
Gly Ala Leu Ser Gly Met Leu Asp Ser Cys
            180             185

<210> SEQ ID NO 52
<211> LENGTH: 226
<212> TYPE: PRT
<213> ORGANISM: Thermobispora bispora

<400> SEQUENCE: 52

Leu Asp Ile Ala Asp Gly Arg Pro Ala Gly Lys Ala Ala Glu Ala
1               5                   10                  15

Ala Thr Gly Thr Ser Pro Leu Ala Asn Pro Asp Gly Thr Arg Pro Gly
            20                  25                  30

Leu Ala Ala Ile Thr Ser Ala Asp Glu Arg Ala Glu Ala Arg Ala Leu
            35                  40                  45

Ile Glu Arg Leu Arg Thr Lys Gly Arg Gly Pro Lys Thr Gly Tyr Glu
        50                  55                  60

Arg Glu Lys Phe Gly Tyr Ala Trp Ala Asp Ser Val Asp Gly Ile Pro
65                  70                  75                  80

Phe Gly Arg Asn Gly Cys Asp Thr Arg Asn Asp Val Leu Lys Arg Asp
                85                  90                  95

Gly Gln Arg Leu Gln Phe Arg Ser Gly Ser Asp Cys Val Val Ile Ser
                100                 105                 110

Met Thr Leu Phe Asp Pro Tyr Thr Gly Lys Thr Ile Glu Trp Thr Lys
            115                 120                 125

Gln Asn Ala Ala Glu Val Gln Ile Asp His Val Val Pro Leu Ser Tyr
        130                 135                 140

Ser Trp Gln Met Gly Ala Ser Arg Trp Ser Asp Glu Lys Arg Arg Gln
145                 150                 155                 160

Leu Ala Asn Asp Pro Leu Asn Leu Met Pro Val Asp Gly Ala Thr Asn
                165                 170                 175

Ser Arg Lys Gly Asp Ser Gly Pro Ala Ser Trp Leu Pro Pro Arg Arg
            180                 185                 190

Glu Ile Arg Cys Ala Tyr Val Val Arg Phe Ala Gln Val Ala Leu Lys
        195                 200                 205

Tyr Asp Leu Pro Val Thr Thr Ala Asp Lys Glu Thr Met Leu Gln Gln
    210                 215                 220

Cys Ser
225

<210> SEQ ID NO 53
<211> LENGTH: 191
<212> TYPE: PRT
<213> ORGANISM: Sporormia fimetaria

<400> SEQUENCE: 53

Leu Pro Ala Pro Val Leu Glu Lys Arg Thr Pro Asn Ile Pro Ser
1               5                   10                  15

Thr Ser Thr Ala Gln Ser Leu Leu Ser Gly Leu Thr Val Ala Pro Gln
            20                  25                  30

Gly Ser Gln Thr Gly Tyr Ser Arg Asp Leu Phe Pro His Trp Ile Thr
        35                  40                  45

Val Ser Gly Thr Cys Asn Thr Arg Glu Thr Val Leu Lys Arg Asp Gly
    50                  55                  60

Ser Asn Val Val Thr Asp Ser Ala Cys Ala Ser Val Ser Gly Ser Trp
65                  70                  75                  80
```

```
Tyr Ser Thr Tyr Asp Gly Ala Thr Trp Thr Ala Ala Ser Asp Val Asp
                85                  90                  95

Ile Asp His Val Val Pro Leu Ser Asn Ala Trp Lys Ser Gly Ala Ala
            100                 105                 110

Ser Trp Thr Thr Ala Arg Arg Gln Ala Phe Ala Asn Asp Leu Thr Asn
            115                 120                 125

Pro Gln Leu Ile Ala Val Thr Asp Asn Val Asn Gln Ala Lys Gly Asp
        130                 135                 140

Gln Gly Pro Glu Ser Trp Lys Pro Pro Leu Thr Ser Tyr Tyr Cys Thr
145                 150                 155                 160

Tyr Ala Lys Met Trp Val Lys Val Lys Ser Val Tyr Ser Leu Thr Val
                165                 170                 175

Thr Ser Ala Glu Lys Ser Ala Leu Ser Ser Met Leu Gly Thr Cys
            180                 185                 190
```

<210> SEQ ID NO 54
<211> LENGTH: 193
<212> TYPE: PRT
<213> ORGANISM: Pycnidiophora cf.dispera

<400> SEQUENCE: 54

```
Leu Pro Ala Pro Ala Pro Val Leu Val Ala Arg Glu Pro Pro Asn Ile
1               5                   10                  15

Pro Ser Thr Ser Ser Ala Gln Ser Met Leu Ser Gly Leu Thr Val Lys
            20                  25                  30

Ala Gln Gly Pro Gln Asp Gly Tyr Ser Arg Asp Leu Phe Pro His Trp
        35                  40                  45

Ile Thr Ile Ser Gly Thr Cys Asn Thr Arg Glu Thr Val Leu Lys Arg
    50                  55                  60

Asp Gly Thr Asn Val Val Thr Asn Ser Ala Cys Ala Ser Thr Ser Gly
65                  70                  75                  80

Ser Trp Tyr Ser Pro Tyr Asp Gly Ala Thr Trp Thr Ala Ala Ser Asp
                85                  90                  95

Val Asp Ile Asp His Ile Val Pro Leu Ser Asn Ala Trp Lys Ser Gly
            100                 105                 110

Ala Ala Ser Trp Thr Thr Ser Arg Arg Gln Gln Phe Ala Asn Asp Leu
            115                 120                 125

Thr Asn Pro Gln Leu Ile Ala Val Thr Asp Ser Val Asn Gln Ala Lys
        130                 135                 140

Gly Asp Lys Gly Pro Glu Asp Trp Lys Pro Ser Arg Thr Ser Tyr His
145                 150                 155                 160

Cys Thr Tyr Ala Lys Met Trp Ile Lys Val Lys Ser Val Tyr Ser Leu
                165                 170                 175

Thr Val Thr Ser Ala Glu Lys Ser Ala Leu Thr Thr Met Leu Asn Thr
            180                 185                 190

Cys
```

<210> SEQ ID NO 55
<211> LENGTH: 199
<212> TYPE: PRT
<213> ORGANISM: Enviromental sample D

<400> SEQUENCE: 55

```
Asp Thr Asp Pro Glu Pro Val Ala Gly Ser Ala Leu Glu Ala Leu Ala
1               5                   10                  15
```

Gly Leu Glu Val Lys Gly Pro Gly Pro Asp Thr Gly Tyr Glu Arg Ala
            20                  25                  30

Leu Phe Gly Pro Pro Trp Ala Asp Val Asp Gly Asn Gly Cys Asp Thr
        35                  40                  45

Arg Asn Asp Ile Leu Ala Arg Asp Leu Thr Asp Leu Thr Phe Ser Thr
    50                  55                  60

Arg Gly Asp Val Cys Glu Val Arg Thr Gly Thr Phe Asp Asp Pro Tyr
65                  70                  75                  80

Thr Gly Glu Thr Ile Asp Phe Arg Arg Gly Asn Ala Thr Ser Ala Ala
                85                  90                  95

Val Gln Ile Asp His Val Val Pro Leu Leu Asp Ala Trp Arg Lys Gly
                100                 105                 110

Ala Arg Ala Trp Asp Asp Glu Thr Arg Arg Gln Phe Ala Asn Asp Pro
            115                 120                 125

Leu Asn Leu Leu Ala Ser Asp Gly Pro Ala Asn Gln Ser Lys Gly Ala
130                 135                 140

Arg Asp Ala Ser Ala Trp Leu Pro Pro Asn His Ala Phe Arg Cys Pro
145                 150                 155                 160

Tyr Val Ala Arg Gln Ile Ala Val Lys Ala Ala Tyr Glu Leu Ser Val
                165                 170                 175

Thr Pro Ser Glu Ser Glu Ala Met Ala Arg Val Leu Ala Asp Cys Pro
            180                 185                 190

Ala Glu Pro Leu Pro Ala Gly
            195

<210> SEQ ID NO 56
<211> LENGTH: 199
<212> TYPE: PRT
<213> ORGANISM: Enviromental sample O

<400> SEQUENCE: 56

Asp Asp Glu Pro Glu Pro Ala Arg Gly Ser Ala Leu Glu Ala Leu Ala
1               5                   10                  15

Arg Leu Glu Val Val Gly Pro Gly Pro Asp Thr Gly Tyr Glu Arg Glu
            20                  25                  30

Leu Phe Gly Pro Ala Trp Ala Asp Val Asp Gly Asn Gly Cys Asp Thr
        35                  40                  45

Arg Asn Asp Ile Leu Ala Arg Asp Leu Thr Asp Leu Thr Phe Ser Thr
    50                  55                  60

Arg Gly Glu Val Cys Glu Val Arg Thr Gly Thr Phe Gln Asp Pro Tyr
65                  70                  75                  80

Thr Gly Glu Thr Ile Asp Phe Arg Arg Gly Asn Ala Thr Ser Met Ala
                85                  90                  95

Val Gln Ile Asp His Val Val Pro Leu Met Asp Ala Trp Arg Lys Gly
                100                 105                 110

Ala Arg Ala Trp Asp Asp Glu Thr Arg Arg Gln Phe Ala Asn Asp Pro
            115                 120                 125

Leu Asn Leu Leu Ala Ser Asp Gly Pro Ala Asn Gln Ser Lys Gly Ala
130                 135                 140

Arg Asp Ala Ser Ala Trp Leu Pro Pro Asn His Ala Phe Arg Cys Pro
145                 150                 155                 160

Tyr Val Ala Arg Gln Ile Ala Val Lys Thr Ala Tyr Glu Leu Ser Val
                165                 170                 175

Thr Pro Ser Glu Ser Glu Ala Met Ala Arg Val Leu Glu Asp Cys Pro
            180                 185                 190

Ala Glu Pro Val Pro Ala Gly
        195

<210> SEQ ID NO 57
<211> LENGTH: 186
<212> TYPE: PRT
<213> ORGANISM: Clavicipitaceae sp-70249

<400> SEQUENCE: 57

Val Pro Val Pro Ala Pro Pro Gly Ile Pro Ser Thr Ser Thr Ala Lys
1               5                   10                  15

Thr Leu Leu Ala Gly Leu Lys Val Ala Thr Pro Leu Ser Gly Asp Gly
            20                  25                  30

Tyr Ser Arg Asp Lys Phe Pro Thr Trp Glu Thr Ile Gln Gly Thr Cys
        35                  40                  45

Asn Ala Arg Glu Phe Val Ile Lys Arg Asp Gly Thr Asp Val Lys Thr
    50                  55                  60

Asn Ser Ala Cys Val Ala Glu Ser Gly Asn Trp Val Ser Pro Tyr Asp
65                  70                  75                  80

Gly Val Lys Phe Thr Ala Ala Arg Asp Leu Asp Ile Asp His Met Val
                85                  90                  95

Pro Leu Lys Asn Ala Trp Ile Ser Gly Ala Ser Gln Trp Thr Thr Glu
            100                 105                 110

Gln Arg Lys Ala Leu Ala Asn Asp Ile Thr Arg Pro Gln Leu Trp Ala
        115                 120                 125

Val Ser Ala His Ala Asn Arg Gly Lys Ser Asp Asp Ser Pro Asp Glu
    130                 135                 140

Trp Lys Pro Pro Leu Lys Thr Phe Trp Cys Thr Tyr Ala Lys Ser Trp
145                 150                 155                 160

Val Gln Val Lys Ser Phe Tyr Lys Leu Thr Ile Thr Asp Thr Glu Lys
                165                 170                 175

Gly Ala Leu Ala Gly Met Leu Asp Thr Cys
            180                 185

<210> SEQ ID NO 58
<211> LENGTH: 187
<212> TYPE: PRT
<213> ORGANISM: Westerdykella sp. AS85-2

<400> SEQUENCE: 58

Phe Pro Ala Pro Ala Ser Val Leu Glu Ala Arg Ala Pro Pro Asn Ile
1               5                   10                  15

Pro Ser Ala Ser Thr Ala Gln Ser Leu Leu Val Gly Leu Thr Val Gln
            20                  25                  30

Pro Gln Gly Pro Gln Asp Gly Tyr Ser Arg Asp Leu Phe Pro His Trp
        35                  40                  45

Ile Thr Ile Ser Gly Thr Cys Asn Thr Arg Glu Thr Val Leu Lys Arg
    50                  55                  60

Asp Gly Ser Asn Val Val Thr Asn Ser Ala Cys Ala Ala Thr Ser Gly
65                  70                  75                  80

Thr Trp Tyr Ser Pro Tyr Asp Gly Ala Thr Trp Thr Ser Ala Ser Asp
                85                  90                  95

Val Asp Ile Asp His Leu Val Pro Leu Ser Asn Ala Trp Lys Ser Gly
            100                 105                 110

Ala Ala Ser Trp Thr Thr Ala Lys Arg Gln Gln Phe Ala Asn Asp Leu
        115                 120                 125

```
Thr Asn Pro Gln Leu Leu Ala Val Thr Asp Arg Val Asn Gln Ala Lys
        130                 135                 140

Gly Asp Lys Gly Pro Glu Ala Trp Lys Pro Ser Leu Ala Ser Tyr His
145                 150                 155                 160

Cys Thr Tyr Ala Lys Met Trp Val Lys Val Lys Ser Lys Asp Val Arg
                165                 170                 175

Leu Thr Gly Asn Trp Thr Lys Asp Asp Gly Trp
            180                 185

<210> SEQ ID NO 59
<211> LENGTH: 194
<212> TYPE: PRT
<213> ORGANISM: Humicolopsis cephalosporioides

<400> SEQUENCE: 59

Ala Pro Thr Pro Ala Pro Val Glu Leu Glu Arg Arg Thr Pro Pro Asn
1               5                   10                  15

Ile Pro Thr Thr Ala Ser Ala Lys Ser Leu Leu Ala Gly Leu Thr Val
                20                  25                  30

Ala Ala Gln Gly Pro Gln Thr Gly Tyr Ser Arg Asp Leu Phe Pro His
            35                  40                  45

Trp Ile Thr Ile Ser Gly Ser Cys Asn Thr Arg Glu Thr Val Leu Lys
        50                  55                  60

Arg Asp Gly Thr Gly Val Val Thr Asp Ser Ala Cys Ala Ser Thr Ala
65                  70                  75                  80

Gly Ser Trp Tyr Ser Pro Tyr Asp Gly Ala Thr Trp Thr Ala Ala Ser
                85                  90                  95

Asp Val Asp Ile Asp His Met Val Pro Leu Ser Asn Ala Trp Lys Ser
            100                 105                 110

Gly Ala Ala Gln Trp Thr Thr Ala Arg Arg Gln Asp Phe Ala Asn Asp
        115                 120                 125

Leu Thr Asn Pro Gln Leu Phe Ala Val Thr Asp Asn Val Asn Gln Glu
    130                 135                 140

Lys Gly Asp Lys Gly Pro Glu Asp Trp Lys Pro Ser Leu Thr Ser Tyr
145                 150                 155                 160

Tyr Cys Thr Tyr Ala Lys Ala Trp Val Lys Val Lys Ser Val Trp Ala
                165                 170                 175

Leu Thr Ile Thr Ser Ala Glu Lys Ser Ala Leu Thr Thr Met Leu Asn
            180                 185                 190

Thr Cys

<210> SEQ ID NO 60
<211> LENGTH: 190
<212> TYPE: PRT
<213> ORGANISM: Neosartorya massa

<400> SEQUENCE: 60

Ile Pro Ala Pro Val Ala Leu Pro Thr Pro Gly Ile Pro Ser Ala
1               5                   10                  15

Ala Thr Ala Glu Ser Glu Leu Ala Ala Leu Thr Val Ala Ala Gln Gly
                20                  25                  30

Ser Ser Ser Gly Tyr Ser Arg Asp Leu Phe Pro His Trp Ile Ser Gln
            35                  40                  45

Gly Gly Ser Cys Asn Thr Arg Glu Val Val Leu Ala Arg Asp Gly Ser
        50                  55                  60
```

```
Gly Val Val Lys Asp Ser Asn Cys Tyr Pro Thr Gly Ser Trp Tyr
65                  70                  75                  80

Ser Pro Tyr Asp Gly Ala Thr Trp Thr Gln Ala Ser Asp Val Asp Ile
            85                  90                  95

Asp His Val Val Pro Leu Ala Asn Ala Trp Arg Ser Gly Ala Ser Lys
                100                 105                 110

Trp Thr Thr Ser Gln Arg Gln Ala Phe Ala Asn Asp Leu Thr Asn Pro
            115                 120                 125

Gln Leu Met Ala Val Thr Asp Asn Val Asn Gln Ala Lys Gly Asp Asp
130             135                 140

Gly Pro Glu Ala Trp Lys Pro Pro Leu Thr Ser Tyr Tyr Cys Thr Tyr
145             150                 155                 160

Ala Lys Met Trp Val Arg Val Lys Tyr Val Tyr Asp Leu Thr Ile Thr
                165                 170                 175

Ser Ala Glu Lys Ser Ala Leu Val Ser Met Leu Asp Thr Cys
                180                 185                 190
```

<210> SEQ ID NO 61
<211> LENGTH: 191
<212> TYPE: PRT
<213> ORGANISM: Roussoella intermedia

<400> SEQUENCE: 61

```
Ala Pro Thr Pro Ala Leu Leu Pro Arg Ala Pro Asn Ile Pro Ser
1               5                   10                  15

Thr Ala Thr Ala Lys Ser Gln Leu Ala Ala Leu Thr Val Ala Ala Gln
                20                  25                  30

Gly Pro Gln Asp Gly Tyr Ser Arg Asp Leu Phe Pro His Trp Ile Thr
            35                  40                  45

Gln Ser Gly Ser Cys Asn Thr Arg Glu Val Val Leu Lys Arg Asp Gly
50                  55                  60

Thr Asn Val Val Gln Asp Ser Ser Cys Ala Ala Thr Ser Gly Thr Trp
65                  70                  75                  80

Val Ser Pro Phe Asp Gly Ala Thr Trp Thr Ala Ala Ser Asp Val Asp
                85                  90                  95

Ile Asp His Leu Val Pro Leu Ser Asn Ala Trp Lys Ser Gly Ala Ala
                100                 105                 110

Ser Trp Thr Thr Ala Arg Arg Gln Ser Phe Ala Asn Asp Leu Thr Asn
            115                 120                 125

Pro Gln Leu Leu Ala Val Thr Asp Glu Val Asn Gln Ala Lys Gly Asp
130             135                 140

Lys Gly Pro Glu Ala Trp Lys Pro Pro Leu Ala Ser Tyr His Cys Thr
145             150                 155                 160

Tyr Ala Lys Met Trp Val Lys Val Lys Ser Thr Tyr Ser Leu Thr Ile
                165                 170                 175

Thr Ser Ala Glu Lys Ser Ala Leu Thr Thr Met Leu Asn Thr Cys
                180                 185                 190
```

<210> SEQ ID NO 62
<211> LENGTH: 191
<212> TYPE: PRT
<213> ORGANISM: Pleosporales

<400> SEQUENCE: 62

```
Leu Pro Thr Pro Ser Leu Val Lys Arg Thr Pro Asn Ile Pro Ser
1               5                   10                  15
```

Thr Thr Ser Ala Lys Ser Leu Leu Ala Gly Leu Thr Val Ala Ala Gln
            20                  25                  30

Gly Pro Gln Asp Gly Tyr Ser Arg Asp Leu Phe Pro His Trp Ile Thr
        35                  40                  45

Ile Ser Gly Thr Cys Asn Thr Arg Glu Thr Val Leu Lys Arg Asp Gly
    50                  55                  60

Thr Asn Val Val Thr Asp Ser Ala Cys Ala Ser Thr Ser Gly Ser Trp
65                  70                  75                  80

Tyr Ser Thr Tyr Asp Gly Ala Thr Trp Thr Ala Ser Asp Val Asp
                85                  90                  95

Ile Asp His Val Val Pro Leu Ser Asn Ala Trp Lys Ser Gly Ala Ala
            100                 105                 110

Ser Trp Thr Thr Ala Arg Arg Gln Ser Phe Ala Asn Asp Leu Thr Asn
            115                 120                 125

Pro Gln Leu Ile Ala Val Thr Asp Ser Val Asn Gln Ser Lys Gly Asp
        130                 135                 140

Lys Gly Pro Glu Ser Trp Lys Pro Pro Leu Thr Ser Tyr His Cys Thr
145                 150                 155                 160

Tyr Ala Lys Met Trp Val Lys Val Lys Asp Val Tyr Ser Leu Thr Val
                165                 170                 175

Thr Ser Ala Glu Lys Ser Ala Leu Thr Thr Met Leu Asn Thr Cys
            180                 185                 190

<210> SEQ ID NO 63
<211> LENGTH: 192
<212> TYPE: PRT
<213> ORGANISM: Phaeosphaeria sp.

<400> SEQUENCE: 63

Leu Pro Ala Pro Ile His Leu Thr Ala Arg Ala Pro Pro Asn Ile Pro
1               5                   10                  15

Ser Ala Ser Glu Ala Arg Thr Gln Leu Ala Gly Leu Thr Val Ala Ala
            20                  25                  30

Gln Gly Pro Gln Asp Gly Tyr Ser Arg Asp Leu Phe Pro His Trp Ile
        35                  40                  45

Thr Gln Ser Gly Thr Cys Asn Thr Arg Glu Thr Val Leu Lys Arg Asp
    50                  55                  60

Gly Thr Asn Val Val Thr Asn Ser Ala Cys Ala Ser Thr Ser Gly Ser
65                  70                  75                  80

Trp Phe Ser Pro Tyr Asp Gly Ala Thr Trp Thr Ala Ala Ser Asp Val
                85                  90                  95

Asp Ile Asp His Met Val Pro Leu Ser Asn Ala Trp Lys Ser Gly Ala
            100                 105                 110

Ala Ser Trp Thr Thr Ala Arg Arg Gln Ala Phe Ala Asn Asp Leu Thr
            115                 120                 125

Asn Pro Gln Leu Leu Ala Val Thr Asp Asn Val Asn Gln Ala Lys Gly
        130                 135                 140

Asp Lys Gly Pro Glu Asp Trp Lys Pro Pro Leu Thr Ser Tyr Tyr Cys
145                 150                 155                 160

Thr Tyr Ala Arg Met Trp Val Lys Val Lys Ser Val Tyr Ala Leu Thr
                165                 170                 175

Val Thr Ser Ala Glu Lys Ser Ala Leu Thr Ser Met Leu Gly Thr Cys
            180                 185                 190

<210> SEQ ID NO 64
<211> LENGTH: 189
<212> TYPE: PRT
<213> ORGANISM: Didymosphaeria futilis

<400> SEQUENCE: 64

Leu Pro Thr Pro Asn Thr Leu Glu Ala Arg Ala Pro Asn Ile Pro
1               5                   10                  15

Ser Thr Ser Ala Ala Gln Ser Gln Leu Ser Ala Leu Thr Val Ala Ala
                20                  25                  30

Gln Gly Pro Gln Thr Gly Tyr Ser Arg Asp Leu Phe Pro His Trp Ile
            35                  40                  45

Thr Gln Ser Gly Thr Cys Asn Thr Arg Glu Thr Val Leu Lys Arg Asp
        50                  55                  60

Gly Thr Asn Val Leu Thr Asp Ser Ala Cys Ala Ser Thr Ser Gly Ser
65                  70                  75                  80

Trp Lys Ser Pro Tyr Asp Gly Ala Thr Trp Thr Ala Ala Ser Asp Val
                85                  90                  95

Asp Ile Asp His Val Val Pro Leu Ser Asn Ala Trp Lys Ser Gly Ala
            100                 105                 110

Ala Ser Trp Thr Thr Ala Arg Arg Gln Ser Phe Ala Asn Asp Leu Thr
        115                 120                 125

Asn Pro Gln Leu Ile Ala Val Thr Asp Asn Val Asn Gln Ala Lys Gly
    130                 135                 140

Asp Lys Gly Pro Glu Asp Trp Lys Pro Pro Leu Thr Ser Tyr Tyr Cys
145                 150                 155                 160

Thr Tyr Ala Lys Met Trp Val Lys Val Lys Ser Val Tyr Ser Leu Thr
                165                 170                 175

Ile Thr Ser Ala Glu Lys Ser Ala Leu Thr Met Leu Ala
            180                 185

<210> SEQ ID NO 65
<211> LENGTH: 109
<212> TYPE: PRT
<213> ORGANISM: Bacillus licheniformis

<400> SEQUENCE: 65

Ala Arg Tyr Asp Asp Ile Leu Tyr Phe Pro Ala Ser Arg Tyr Pro Glu
1               5                   10                  15

Thr Gly Ala His Ile Ser Asp Ala Ile Lys Ala Gly His Ser Asp Val
                20                  25                  30

Cys Thr Ile Glu Arg Ser Gly Ala Asp Lys Arg Gln Glu Ser Leu
            35                  40                  45

Lys Gly Ile Pro Thr Lys Pro Gly Phe Asp Arg Asp Glu Trp Pro Met
        50                  55                  60

Ala Met Cys Glu Glu Gly Gly Lys Gly Ala Ser Val Arg Tyr Val Ser
65                  70                  75                  80

Ser Ser Asp Asn Arg Gly Ala Gly Ser Trp Val Gly Asn Arg Leu Ser
                85                  90                  95

Gly Phe Ala Asp Gly Thr Arg Ile Leu Phe Ile Val Gln
            100                 105

<210> SEQ ID NO 66
<211> LENGTH: 110
<212> TYPE: PRT
<213> ORGANISM: Bacillus subtilis

<400> SEQUENCE: 66

Ala Ser Ser Tyr Asp Lys Val Leu Tyr Phe Pro Leu Ser Arg Tyr Pro
1               5                   10                  15

Glu Thr Gly Ser His Ile Arg Asp Ala Ile Ala Glu Gly His Pro Asp
            20                  25                  30

Ile Cys Thr Ile Asp Arg Asp Gly Ala Asp Lys Arg Arg Glu Glu Ser
        35                  40                  45

Leu Lys Gly Ile Pro Thr Lys Pro Gly Tyr Asp Arg Asp Glu Trp Pro
50                  55                  60

Met Ala Val Cys Glu Glu Gly Ala Gly Ala Asp Val Arg Tyr Val
65                  70                  75                  80

Thr Pro Ser Asp Asn Arg Gly Ala Gly Ser Trp Val Gly Asn Gln Met
                85                  90                  95

Ser Ser Tyr Pro Asp Gly Thr Arg Val Leu Phe Ile Val Gln
            100                 105                 110

<210> SEQ ID NO 67
<211> LENGTH: 221
<212> TYPE: PRT
<213> ORGANISM: Aspergillus oryzae

<400> SEQUENCE: 67

Val Pro Val Asn Pro Glu Pro Asp Ala Thr Ser Val Glu Asn Val Ala
1               5                   10                  15

Leu Lys Thr Gly Ser Gly Asp Ser Gln Ser Asp Pro Ile Lys Ala Asp
            20                  25                  30

Leu Glu Val Lys Gly Gln Ser Ala Leu Pro Phe Asp Val Asp Cys Trp
        35                  40                  45

Ala Ile Leu Cys Lys Gly Ala Pro Asn Val Leu Gln Arg Val Asn Glu
50                  55                  60

Lys Thr Lys Asn Ser Asn Arg Asp Arg Ser Gly Ala Asn Lys Gly Pro
65                  70                  75                  80

Phe Lys Asp Pro Gln Lys Trp Gly Ile Lys Ala Leu Pro Pro Lys Asn
                85                  90                  95

Pro Ser Trp Ser Ala Gln Asp Phe Lys Ser Pro Glu Glu Tyr Ala Phe
            100                 105                 110

Ala Ser Ser Leu Gln Gly Gly Thr Asn Ala Ile Leu Ala Pro Val Asn
        115                 120                 125

Leu Ala Ser Gln Asn Ser Gln Gly Gly Val Leu Asn Gly Phe Tyr Ser
130                 135                 140

Ala Asn Lys Val Ala Gln Phe Asp Pro Ser Lys Pro Gln Gln Thr Lys
145                 150                 155                 160

Gly Thr Trp Phe Gln Ile Thr Lys Phe Thr Gly Ala Ala Gly Pro Tyr
                165                 170                 175

Cys Lys Ala Leu Gly Ser Asn Asp Lys Ser Val Cys Asp Lys Asn Lys
            180                 185                 190

Asn Ile Ala Gly Asp Trp Gly Phe Asp Pro Ala Lys Trp Ala Tyr Gln
        195                 200                 205

Tyr Asp Glu Lys Asn Asn Lys Phe Asn Tyr Val Gly Lys
210                 215                 220

<210> SEQ ID NO 68
<211> LENGTH: 188
<212> TYPE: PRT
<213> ORGANISM: Trichoderma harzianum

<400> SEQUENCE: 68

```
Ala Pro Ala Pro Met Pro Thr Pro Pro Gly Ile Pro Thr Glu Ser Ser
1               5                   10                  15

Ala Arg Thr Gln Leu Ala Gly Leu Thr Val Ala Val Ala Gly Ser Gly
            20                  25                  30

Thr Gly Tyr Ser Arg Asp Leu Phe Pro Thr Trp Asp Ala Ile Ser Gly
        35                  40                  45

Asn Cys Asn Ala Arg Glu Tyr Val Leu Lys Arg Asp Gly Glu Gly Val
    50                  55                  60

Gln Val Asn Asn Ala Cys Glu Ser Gln Ser Gly Thr Trp Ile Ser Pro
65                  70                  75                  80

Tyr Asp Asn Ala Ser Phe Thr Asn Ala Ser Ser Leu Asp Ile Asp His
                85                  90                  95

Met Val Pro Leu Lys Asn Ala Trp Ile Ser Gly Ala Ser Ser Trp Thr
            100                 105                 110

Thr Ala Gln Arg Glu Ala Leu Ala Asn Asp Val Ser Arg Pro Gln Leu
        115                 120                 125

Trp Ala Val Ser Ala Ser Ala Asn Arg Ser Lys Gly Asp Arg Ser Pro
130                 135                 140

Asp Gln Trp Lys Pro Pro Leu Thr Ser Phe Tyr Cys Thr Tyr Ala Lys
145                 150                 155                 160

Ser Trp Ile Asp Val Lys Ser Phe Tyr Lys Leu Thr Ile Thr Ser Ala
                165                 170                 175

Glu Lys Thr Ala Leu Ser Ser Met Leu Asp Thr Cys
            180                 185
```

<210> SEQ ID NO 69
<211> LENGTH: 5
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Xaa = Thr (T) or Asp (D) or Ser (S)
<220> FEATURE:
<221> NAME/KEY: MISC_FEATURE
<222> LOCATION: (2)..(2)
<223> OTHER INFORMATION: Xaa = Gly (G) or Asn (N)

<400> SEQUENCE: 69

```
Xaa Xaa Pro Gln Leu
1               5
```

<210> SEQ ID NO 70
<211> LENGTH: 5
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Xaa = F (phe) or L (Leu) or Y (Tyr) or I (Ile)
<220> FEATURE:
<221> NAME/KEY: MISC_FEATURE
<222> LOCATION: (3)..(3)
<223> OTHER INFORMATION: Xaa = N (Asn) or R (Arg)
<220> FEATURE:
<221> NAME/KEY: MISC_FEATURE
<222> LOCATION: (5)..(5)
<223> OTHER INFORMATION: Xaa = L (Leu) or I (Ile) or P (Phe) or V (Val)

```
<400> SEQUENCE: 70

Xaa Ala Xaa Asp Xaa
1               5

<210> SEQ ID NO 71
<211> LENGTH: 4
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (2)..(2)
<223> OTHER INFORMATION: Xaa= Asp (D) or Asn (N)
<220> FEATURE:
<221> NAME/KEY: MISC_FEATURE
<222> LOCATION: (4)..(4)
<223> OTHER INFORMATION: Xaa= Ala (A) or Arg (R)

<400> SEQUENCE: 71

Cys Xaa Thr Xaa
1

<210> SEQ ID NO 72
<211> LENGTH: 4
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Xaa = Asp (D) or Gln (Q)
<220> FEATURE:
<221> NAME/KEY: MISC_FEATURE
<222> LOCATION: (2)..(2)
<223> OTHER INFORMATION: Xaa = Ile (I) or Val (V)

<400> SEQUENCE: 72

Xaa Xaa Asp His
1

<210> SEQ ID NO 73
<211> LENGTH: 7
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Xaa = Asp (D) or Met (M) or Leu (L)
<220> FEATURE:
<221> NAME/KEY: MISC_FEATURE
<222> LOCATION: (2)..(2)
<223> OTHER INFORMATION: Xaa = Ser (S) or Thr (T)
<220> FEATURE:
<221> NAME/KEY: MISC_FEATURE
<222> LOCATION: (7)..(7)
<223> OTHER INFORMATION: Xaa = Asp (D) or Asn (N)

<400> SEQUENCE: 73

Xaa Xaa Gly Tyr Ser Arg Xaa
1               5

<210> SEQ ID NO 74
<211> LENGTH: 8
<212> TYPE: PRT
<213> ORGANISM: Artificial
<220> FEATURE:
```

```
<223> OTHER INFORMATION: Motif
<220> FEATURE:
<221> NAME/KEY: MISC_FEATURE
<222> LOCATION: (3)..(3)
<223> OTHER INFORMATION: Xaa = any amino acid

<400> SEQUENCE: 74

Ala Ser Xaa Asn Arg Ser Lys Gly
1               5

<210> SEQ ID NO 75
<211> LENGTH: 8
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Xaa = Val (V) or Ile (I)
<220> FEATURE:
<221> NAME/KEY: MISC_FEATURE
<222> LOCATION: (4)..(4)
<223> OTHER INFORMATION: Xaa = Ser (S) or Ala (A)

<400> SEQUENCE: 75

Xaa Pro Leu Xaa Asn Ala Trp Lys
1               5

<210> SEQ ID NO 76
<211> LENGTH: 4
<212> TYPE: PRT
<213> ORGANISM: Artificial
<220> FEATURE:
<223> OTHER INFORMATION: Motif

<400> SEQUENCE: 76

Asn Pro Gln Leu
1

<210> SEQ ID NO 77
<211> LENGTH: 4
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (2)..(2)
<223> OTHER INFORMATION: Xaa = Gln (Q) or Glu(E)
<220> FEATURE:
<221> NAME/KEY: MISC_FEATURE
<222> LOCATION: (4)..(4)
<223> OTHER INFORMATION: Xaa = Trp (W) or Tyr (Y)

<400> SEQUENCE: 77

Pro Xaa Leu Xaa
1

<210> SEQ ID NO 78
<211> LENGTH: 4
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Xaa=Lys (K) or His (H) or Glu (E)
```

```
<400> SEQUENCE: 78

Xaa Asn Ala Trp
1

<210> SEQ ID NO 79
<211> LENGTH: 269
<212> TYPE: PRT
<213> ORGANISM: Bacillus lentus

<400> SEQUENCE: 79

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 80
<211> LENGTH: 275
<212> TYPE: PRT
<213> ORGANISM: Bacillus amyloliquefaciens

<400> SEQUENCE: 80

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30
```

```
Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
 50                  55                  60

Gly Thr His Val Ala Gly Thr Val Ala Ala Leu Asn Asn Ser Ile Gly
 65                  70                  75                  80

Val Leu Gly Val Ala Pro Ser Ala Ser Leu Tyr Ala Val Lys Val Leu
                 85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
            115                 120                 125

Pro Ser Gly Ser Ala Ala Leu Lys Ala Ala Val Asp Lys Ala Val Ala
130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
            195                 200                 205

Leu Pro Gly Asn Lys Tyr Gly Ala Tyr Asn Gly Thr Ser Met Ala Ser
            210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
                260                 265                 270

Ala Ala Gln
        275

<210> SEQ ID NO 81
<211> LENGTH: 311
<212> TYPE: PRT
<213> ORGANISM: Bacillus subtilis

<400> SEQUENCE: 81

Ala Val Pro Ser Thr Gln Thr Pro Trp Gly Ile Lys Ser Ile Tyr Asn
 1               5                  10                  15

Asp Gln Ser Ile Thr Lys Thr Gly Gly Ser Gly Ile Lys Val Ala
             20                  25                  30

Val Leu Asp Thr Gly Val Tyr Thr Ser His Leu Asp Leu Ala Gly Ser
            35                  40                  45

Ala Glu Gln Cys Lys Asp Phe Thr Gln Ser Asn Pro Leu Val Asp Gly
 50                  55                  60

Ser Cys Thr Asp Arg Gln Gly His Gly Thr His Val Ala Gly Thr Val
 65                  70                  75                  80

Leu Ala His Gly Gly Ser Asn Gly Gln Gly Val Tyr Gly Val Ala Pro
                 85                  90                  95

Gln Ala Lys Leu Trp Ala Tyr Lys Val Leu Gly Asp Asn Gly Ser Gly
            100                 105                 110

Tyr Ser Asp Asp Ile Ala Ala Ile Arg His Val Ala Asp Glu Ala
            115                 120                 125
```

```
Ser Arg Thr Gly Ser Lys Val Ile Asn Met Ser Leu Gly Ser Ser
130                 135                 140

Ala Lys Asp Ser Leu Ile Ala Ser Ala Val Asp Tyr Ala Tyr Gly Lys
145                 150                 155                 160

Gly Val Leu Ile Val Ala Ala Ala Gly Asn Ser Gly Ser Gly Ser Asn
                165                 170                 175

Thr Ile Gly Phe Pro Gly Gly Leu Val Asn Ala Val Ala Val Ala Ala
                180                 185                 190

Leu Glu Asn Val Gln Gln Asn Gly Thr Tyr Arg Val Ala Asp Phe Ser
                195                 200                 205

Ser Arg Gly Asn Pro Ala Thr Ala Gly Asp Tyr Ile Ile Gln Glu Arg
210                 215                 220

Asp Ile Glu Val Ser Ala Pro Gly Ala Ser Val Glu Ser Thr Trp Tyr
225                 230                 235                 240

Thr Gly Gly Tyr Asn Thr Ile Ser Gly Thr Ser Met Ala Thr Pro His
                245                 250                 255

Val Ala Gly Leu Ala Ala Lys Ile Trp Ser Ala Asn Thr Ser Leu Ser
                260                 265                 270

His Ser Gln Leu Arg Thr Glu Leu Gln Asn Arg Ala Lys Val Tyr Asp
                275                 280                 285

Ile Lys Gly Gly Ile Gly Ala Gly Thr Gly Asp Asp Tyr Ala Ser Gly
290                 295                 300

Phe Gly Tyr Pro Arg Val Lys
305                 310

<210> SEQ ID NO 82
<211> LENGTH: 298
<212> TYPE: PRT
<213> ORGANISM: Bacillus bogoriensis

<400> SEQUENCE: 82

Ala Asn Ser Gly Phe Tyr Val Ser Gly Thr Thr Leu Tyr Asp Ala Asn
1               5                   10                  15

Gly Asn Pro Phe Val Met Arg Gly Ile Asn His Gly His Ala Trp Tyr
                20                  25                  30

Lys Asp Gln Ala Thr Thr Ala Ile Glu Gly Ile Ala Asn Thr Gly Ala
            35                  40                  45

Asn Thr Val Arg Ile Val Leu Ser Asp Gly Gly Gln Trp Thr Lys Asp
50                  55                  60

Asp Ile His Thr Val Arg Asn Leu Ile Ser Leu Ala Glu Asp Asn His
65                  70                  75                  80

Leu Val Ala Val Leu Glu Val His Asp Ala Thr Gly Tyr Asp Ser Ile
                85                  90                  95

Ala Ser Leu Asn Arg Ala Val Asp Tyr Trp Ile Glu Met Arg Ser Ala
            100                 105                 110

Leu Ile Gly Lys Glu Asp Thr Val Ile Ile Asn Ile Ala Asn Glu Trp
        115                 120                 125

Phe Gly Ser Trp Glu Gly Asp Ala Trp Ala Asp Gly Tyr Lys Gln Ala
    130                 135                 140

Ile Pro Arg Leu Arg Asn Ala Gly Leu Asn His Thr Leu Met Val Asp
145                 150                 155                 160

Ala Ala Gly Trp Gly Gln Phe Pro Gln Ser Ile His Asp Tyr Gly Arg
                165                 170                 175
```

```
Glu Val Phe Asn Ala Asp Pro Gln Arg Asn Thr Met Phe Ser Ile His
                180                 185                 190

Met Tyr Glu Tyr Ala Gly Gly Asn Ala Ser Gln Val Arg Thr Asn Ile
            195                 200                 205

Asp Arg Val Leu Asn Gln Asp Leu Ala Leu Val Ile Gly Glu Phe Gly
        210                 215                 220

His Arg His Thr Asn Gly Asp Val Asp Glu Ala Thr Ile Met Ser Tyr
225                 230                 235                 240

Ser Glu Gln Arg Gly Val Gly Trp Leu Ala Trp Ser Trp Lys Gly Asn
                245                 250                 255

Gly Pro Glu Trp Glu Tyr Leu Asp Leu Ser Asn Asp Trp Ala Gly Asn
            260                 265                 270

Asn Leu Thr Ala Trp Gly Asn Thr Ile Val Asn Gly Pro Tyr Gly Leu
        275                 280                 285

Arg Glu Thr Ser Arg Leu Ser Thr Val Phe
            290                 295

<210> SEQ ID NO 83
<211> LENGTH: 278
<212> TYPE: PRT
<213> ORGANISM: thielavia terrestris

<400> SEQUENCE: 83

Ala Ser Gly Ser Gly Gln Ser Thr Arg Tyr Trp Asp Cys Cys Lys Pro
1               5                   10                  15

Ser Cys Ala Trp Pro Gly Lys Ala Ala Val Ser Gln Pro Val Tyr Ala
            20                  25                  30

Cys Asp Ala Asn Phe Gln Arg Leu Ser Asp Phe Asn Val Gln Ser Gly
        35                  40                  45

Cys Asn Gly Gly Ser Ala Tyr Ser Cys Ala Asp Gln Thr Pro Trp Ala
    50                  55                  60

Val Asn Asp Asn Leu Ala Tyr Gly Phe Ala Ala Thr Ser Ile Ala Gly
65                  70                  75                  80

Gly Ser Glu Ser Ser Trp Cys Cys Ala Cys Tyr Ala Leu Thr Phe Thr
                85                  90                  95

Ser Gly Pro Val Ala Gly Lys Thr Met Val Val Gln Ser Thr Ser Thr
            100                 105                 110

Gly Gly Asp Leu Gly Ser Asn Gln Phe Asp Ile Ala Met Pro Gly Gly
        115                 120                 125

Gly Val Gly Ile Phe Asn Gly Cys Ser Ser Gln Phe Gly Gly Leu Pro
    130                 135                 140

Gly Ala Gln Tyr Gly Gly Ile Ser Ser Arg Asp Gln Cys Asp Ser Phe
145                 150                 155                 160

Pro Ala Pro Leu Lys Pro Gly Cys Gln Trp Arg Phe Asp Trp Phe Gln
                165                 170                 175

Asn Ala Asp Asn Pro Thr Phe Thr Phe Gln Gln Val Gln Cys Pro Ala
            180                 185                 190

Glu Ile Val Ala Arg Ser Gly Cys Lys Arg Asn Asp Asp Ser Ser Phe
        195                 200                 205

Pro Val Phe Thr Pro Pro Ser Gly Gly Asn Gly Gly Thr Gly Thr Pro
    210                 215                 220

Thr Ser Thr Ala Pro Gly Ser Gly Gln Thr Ser Pro Gly Gly Gly Ser
225                 230                 235                 240
```

```
Gly Cys Thr Ser Gln Lys Trp Ala Gln Cys Gly Ile Gly Phe Ser
                245                 250                 255

Gly Cys Thr Thr Cys Val Ser Gly Thr Thr Cys Gln Lys Leu Asn Asp
            260                 265                 270

Tyr Phe Ser Gln Cys Leu
        275
```

<210> SEQ ID NO 84
<211> LENGTH: 470
<212> TYPE: PRT
<213> ORGANISM: humicola insolens

<400> SEQUENCE: 84

```
Met Arg Ser Ser Pro Leu Leu Arg Ser Ala Val Ala Ala Leu Pro
1               5                   10                  15

Val Leu Ala Leu Ala Ala Asp Gly Arg Ser Thr Arg Tyr Trp Asp Cys
            20                  25                  30

Cys Lys Pro Ser Cys Gly Trp Ala Lys Lys Ala Pro Val Asn Gln Pro
        35                  40                  45

Val Phe Ser Cys Asn Ala Asn Phe Gln Arg Ile Thr Asp Phe Asp Ala
    50                  55                  60

Lys Ser Gly Cys Glu Pro Gly Gly Val Ala Tyr Ser Cys Ala Asp Gln
65                  70                  75                  80

Thr Pro Trp Ala Val Asn Asp Asp Phe Ala Leu Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125

Ser Thr Ser Thr Gly Gly Asp Leu Gly Ser Asn His Phe Asp Leu Asn
    130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
            180                 185                 190

Asp Trp Phe Lys Asn Ala Asp Asn Pro Ser Phe Ser Phe Arg Gln Val
        195                 200                 205

Gln Cys Pro Ala Glu Leu Val Ala Arg Thr Gly Cys Arg Arg Asn Asp
    210                 215                 220

Asp Gly Asn Phe Pro Ala Val Gln Ile Pro Ser Ser Thr Ser Ser
225                 230                 235                 240

Pro Val Asn Gln Pro Thr Ser Thr Ser Thr Ser Thr Ser Thr
                245                 250                 255

Ser Ser Pro Pro Val Gln Pro Thr Thr Pro Ser Gly Cys Ala Asp Gly
            260                 265                 270

Arg Ser Thr Arg Tyr Trp Asp Cys Cys Lys Pro Ser Cys Gly Trp Ala
        275                 280                 285

Lys Lys Ala Pro Val Asn Gln Pro Val Phe Ser Cys Asn Ala Asn Phe
    290                 295                 300

Gln Arg Ile Thr Asp Phe Asp Ala Lys Ser Gly Cys Glu Pro Gly Gly
305                 310                 315                 320
```

```
Val Ala Tyr Ser Cys Ala Asp Gln Thr Pro Trp Ala Val Asn Asp Asp
                325                 330                 335

Phe Ala Leu Gly Phe Ala Ala Thr Ser Ile Ala Gly Ser Asn Glu Ala
            340                 345                 350

Gly Trp Cys Cys Ala Cys Tyr Glu Leu Thr Phe Thr Ser Gly Pro Val
            355                 360                 365

Ala Gly Lys Lys Met Val Val Gln Ser Thr Ser Thr Gly Gly Asp Leu
            370                 375                 380

Gly Ser Asn His Phe Asp Leu Asn Ile Pro Gly Gly Val Gly Ile
385                 390                 395                 400

Phe Asp Gly Cys Thr Pro Gln Phe Gly Leu Pro Gly Gln Arg Tyr
                405                 410                 415

Gly Gly Ile Ser Ser Arg Asn Glu Cys Asp Arg Phe Pro Asp Ala Leu
            420                 425                 430

Lys Pro Gly Cys Tyr Trp Arg Phe Asp Trp Phe Lys Asn Ala Asp Asn
            435                 440                 445

Pro Ser Phe Ser Phe Arg Gln Val Gln Cys Pro Ala Glu Leu Val Ala
    450                 455                 460

Arg Thr Gly Cys Arg Arg
465             470

<210> SEQ ID NO 85
<211> LENGTH: 425
<212> TYPE: PRT
<213> ORGANISM: Escherichia coli

<400> SEQUENCE: 85

Thr Ala Leu Leu Leu Gly Leu Val Asn Gly Gln Lys Pro Gly Glu Thr
1               5                   10                  15

Lys Glu Val His Pro Gln Leu Thr Thr Phe Arg Cys Thr Lys Arg Gly
            20                  25                  30

Gly Cys Lys Pro Ala Thr Asn Phe Ile Val Leu Asp Ser Leu Ser His
        35                  40                  45

Pro Ile His Arg Ala Glu Gly Leu Gly Pro Gly Gly Cys Gly Asp Trp
    50                  55                  60

Gly Asn Pro Pro Lys Asp Val Cys Pro Asp Val Glu Ser Cys Ala
65                  70                  75                  80

Lys Asn Cys Ile Met Glu Gly Ile Pro Asp Tyr Ser Gln Tyr Gly Val
                85                  90                  95

Thr Thr Asn Gly Thr Ser Leu Arg Leu Gln His Ile Leu Pro Asp Gly
            100                 105                 110

Arg Val Pro Ser Pro Arg Val Tyr Leu Leu Asp Lys Thr Lys Arg Arg
        115                 120                 125

Tyr Glu Met Leu His Leu Thr Gly Phe Glu Phe Thr Phe Asp Val Asp
    130                 135                 140

Ala Thr Lys Leu Pro Cys Gly Met Asn Ser Ala Leu Tyr Leu Ser Glu
145                 150                 155                 160

Met His Pro Thr Gly Ala Lys Ser Lys Tyr Asn Pro Gly Gly Ala Tyr
                165                 170                 175

Tyr Gly Thr Gly Tyr Cys Asp Ala Gln Cys Phe Val Thr Pro Phe Ile
            180                 185                 190

Asn Gly Leu Gly Asn Ile Glu Gly Lys Gly Ser Cys Cys Asn Glu Met
        195                 200                 205
```

```
Asp Ile Trp Glu Ala Asn Ser Arg Ala Ser His Val Ala Pro His Thr
    210                 215                 220

Cys Asn Lys Lys Gly Leu Tyr Leu Cys Glu Gly Glu Cys Ala Phe
225                 230                 235                 240

Glu Gly Val Cys Asp Lys Asn Gly Cys Gly Trp Asn Asn Tyr Arg Val
                245                 250                 255

Asn Val Thr Asp Tyr Tyr Gly Arg Gly Glu Glu Phe Lys Val Asn Thr
            260                 265                 270

Leu Lys Pro Phe Thr Val Val Thr Gln Phe Leu Ala Asn Arg Arg Gly
        275                 280                 285

Lys Leu Glu Lys Ile His Arg Phe Tyr Val Gln Asp Gly Lys Val Ile
    290                 295                 300

Glu Ser Phe Tyr Thr Asn Lys Glu Gly Val Pro Tyr Thr Asn Met Ile
305                 310                 315                 320

Asp Asp Glu Phe Cys Glu Ala Thr Gly Ser Arg Lys Tyr Met Glu Leu
                325                 330                 335

Gly Ala Thr Gln Gly Met Gly Glu Ala Leu Thr Arg Gly Met Val Leu
            340                 345                 350

Ala Met Ser Ile Trp Trp Asp Gln Gly Gly Asn Met Glu Trp Leu Asp
        355                 360                 365

His Gly Glu Ala Gly Pro Cys Ala Lys Gly Glu Gly Ala Pro Ser Asn
    370                 375                 380

Ile Val Gln Val Glu Pro Phe Pro Glu Val Thr Tyr Thr Asn Leu Arg
385                 390                 395                 400

Trp Gly Glu Ile Gly Ser Thr Tyr Gln Glu Val Gln Lys Pro Lys Pro
                405                 410                 415

Lys Pro Gly His Gly Pro Arg Ser Asp
            420                 425

<210> SEQ ID NO 86
<211> LENGTH: 773
<212> TYPE: PRT
<213> ORGANISM: bacillus subtilis

<400> SEQUENCE: 86

Ala Glu Gly Asn Thr Arg Glu Asp Asn Phe Lys His Leu Leu Gly Asn
1               5                   10                  15

Asp Asn Val Lys Arg Pro Ser Glu Ala Gly Ala Leu Gln Leu Gln Glu
            20                  25                  30

Val Asp Gly Gln Met Thr Leu Val Asp Gln His Gly Glu Lys Ile Gln
        35                  40                  45

Leu Arg Gly Met Ser Thr His Gly Leu Gln Trp Phe Pro Glu Ile Leu
    50                  55                  60

Asn Asp Asn Ala Tyr Lys Ala Leu Ala Asn Asp Trp Glu Ser Asn Met
65                  70                  75                  80

Ile Arg Leu Ala Met Tyr Val Gly Glu Asn Gly Tyr Ala Ser Asn Pro
                85                  90                  95

Glu Leu Ile Lys Ser Arg Val Ile Lys Gly Ile Asp Leu Ala Ile Glu
            100                 105                 110

Asn Asp Met Tyr Val Ile Val Asp Trp His Val His Ala Pro Gly Asp
        115                 120                 125

Pro Arg Asp Pro Val Tyr Ala Gly Ala Glu Asp Phe Phe Arg Asp Ile
    130                 135                 140
```

```
Ala Ala Leu Tyr Pro Asn Asn Pro His Ile Ile Tyr Glu Leu Ala Asn
145                 150                 155                 160

Glu Pro Ser Ser Asn Asn Asn Gly Gly Ala Gly Ile Pro Asn Asn Glu
            165                 170                 175

Glu Gly Trp Asn Ala Val Lys Glu Tyr Ala Asp Pro Ile Val Glu Met
            180                 185                 190

Leu Arg Asp Ser Gly Asn Ala Asp Asp Asn Ile Ile Val Gly Ser
        195                 200                 205

Pro Asn Trp Ser Gln Arg Pro Asp Leu Ala Ala Asp Asn Pro Ile Asn
210                 215                 220

Asp His His Thr Met Tyr Thr Val His Phe Tyr Thr Gly Ser His Ala
225                 230                 235                 240

Ala Ser Thr Glu Ser Tyr Pro Pro Glu Thr Pro Asn Ser Glu Arg Gly
            245                 250                 255

Asn Val Met Ser Asn Thr Arg Tyr Ala Leu Glu Asn Gly Val Ala Val
            260                 265                 270

Phe Ala Thr Glu Trp Gly Thr Ser Gln Ala Asn Gly Asp Gly Gly Pro
        275                 280                 285

Tyr Phe Asp Glu Ala Asp Val Trp Ile Glu Phe Leu Asn Glu Asn Asn
290                 295                 300

Ile Ser Trp Ala Asn Trp Ser Leu Thr Asn Lys Asn Glu Val Ser Gly
305                 310                 315                 320

Ala Phe Thr Pro Phe Glu Leu Gly Lys Ser Asn Ala Thr Asn Leu Asp
            325                 330                 335

Pro Gly Pro Asp His Val Trp Ala Pro Glu Leu Ser Leu Ser Gly
        340                 345                 350

Glu Tyr Val Arg Ala Arg Ile Lys Gly Val Asn Tyr Glu Pro Ile Asp
        355                 360                 365

Arg Thr Lys Tyr Thr Lys Val Leu Trp Asp Phe Asn Asp Gly Thr Lys
370                 375                 380

Gln Gly Phe Gly Val Asn Ser Asp Ser Pro Asn Lys Glu Leu Ile Ala
385                 390                 395                 400

Val Asp Asn Glu Asn Asn Thr Leu Lys Val Ser Gly Leu Asp Val Ser
            405                 410                 415

Asn Asp Val Ser Asp Gly Asn Phe Trp Ala Asn Ala Arg Leu Ser Ala
            420                 425                 430

Asp Gly Trp Gly Lys Ser Val Asp Ile Leu Gly Ala Glu Lys Leu Thr
        435                 440                 445

Met Asp Val Ile Val Asp Glu Pro Thr Thr Val Ala Ile Ala Ala Ile
        450                 455                 460

Pro Gln Ser Ser Lys Ser Gly Trp Ala Asn Pro Glu Arg Ala Val Arg
465                 470                 475                 480

Val Asn Ala Glu Asp Phe Val Gln Gln Thr Asp Gly Lys Tyr Lys Ala
            485                 490                 495

Gly Leu Thr Ile Thr Gly Glu Asp Ala Pro Asn Leu Lys Asn Ile Ala
        500                 505                 510

Phe His Glu Glu Asp Asn Asn Met Asn Asn Ile Ile Leu Phe Val Gly
        515                 520                 525

Thr Asp Ala Ala Asp Val Ile Tyr Leu Asp Asn Ile Lys Val Ile Gly
        530                 535                 540

Thr Glu Val Glu Ile Pro Val Val His Asp Pro Lys Gly Glu Ala Val
545                 550                 555                 560
```

```
Leu Pro Ser Val Phe Glu Asp Gly Thr Arg Gln Gly Trp Asp Trp Ala
                565                 570                 575

Gly Glu Ser Gly Val Lys Thr Ala Leu Thr Ile Glu Glu Ala Asn Gly
            580                 585                 590

Ser Asn Ala Leu Ser Trp Glu Phe Gly Tyr Pro Glu Val Lys Pro Ser
        595                 600                 605

Asp Asn Trp Ala Thr Ala Pro Arg Leu Asp Phe Trp Lys Ser Asp Leu
    610                 615                 620

Val Arg Gly Glu Asn Asp Tyr Val Ala Phe Asp Phe Tyr Leu Asp Pro
625                 630                 635                 640

Val Arg Ala Thr Glu Gly Ala Met Asn Ile Asn Leu Val Phe Gln Pro
                645                 650                 655

Pro Thr Asn Gly Tyr Trp Val Gln Ala Pro Lys Thr Tyr Thr Ile Asn
            660                 665                 670

Phe Asp Glu Leu Glu Glu Ala Asn Gln Val Asn Gly Leu Tyr His Tyr
        675                 680                 685

Glu Val Lys Ile Asn Val Arg Asp Ile Thr Asn Ile Gln Asp Asp Thr
    690                 695                 700

Leu Leu Arg Asn Met Met Ile Ile Phe Ala Asp Val Glu Ser Asp Phe
705                 710                 715                 720

Ala Gly Arg Val Phe Val Asp Asn Val Arg Phe Glu Gly Ala Ala Thr
                725                 730                 735

Thr Glu Pro Val Glu Pro Glu Pro Val Asp Pro Gly Glu Glu Thr Pro
            740                 745                 750

Pro Val Asp Glu Lys Glu Ala Lys Lys Glu Gln Lys Glu Ala Glu Lys
        755                 760                 765

Glu Glu Lys Glu Glu
    770

<210> SEQ ID NO 87
<211> LENGTH: 524
<212> TYPE: PRT
<213> ORGANISM: Paenibacillus polymyxa

<400> SEQUENCE: 87

Val Val His Gly Gln Thr Ala Lys Thr Ile Thr Ile Lys Val Asp Thr
1               5                   10                  15

Phe Lys Asp Arg Lys Pro Ile Ser Pro Tyr Ile Tyr Gly Thr Asn Gln
                20                  25                  30

Asp Leu Ala Gly Asp Glu Asn Met Ala Ala Arg Arg Leu Gly Gly Asn
            35                  40                  45

Arg Met Thr Gly Tyr Asn Trp Glu Asn Asn Met Ser Asn Ala Gly Ser
50                  55                  60

Asp Trp Gln His Ser Ser Asp Asn Tyr Leu Cys Ser Asn Gly Gly Leu
65                  70                  75                  80

Thr Gln Ala Glu Cys Glu Lys Pro Gly Ala Val Val Thr Ser Phe His
                85                  90                  95

Asp Gln Ser Leu Lys Leu Gly Thr Tyr Ser Leu Val Thr Leu Pro Met
            100                 105                 110

Ala Gly Tyr Val Ala Ala Asp Gly Asn Gly Ser Val Gln Glu Ser Glu
        115                 120                 125

Ala Ala Pro Ser Ala Arg Trp Asn Gln Val Val Asn Ala Lys Asn Ala
    130                 135                 140

Pro Phe Gln Leu Gln Pro Asp Leu Asn Asp Asn Tyr Val Tyr Val Asp
145                 150                 155                 160
```

```
Glu Phe Val His Phe Leu Val Asn Lys Tyr Gly Thr Ala Ser Thr Lys
                165                 170                 175

Ala Gly Val Lys Gly Tyr Ala Leu Asp Asn Glu Pro Ala Leu Trp Ser
            180                 185                 190

His Thr His Pro Arg Ile His Pro Glu Lys Val Gly Ala Lys Glu Leu
        195                 200                 205

Val Asp Arg Ser Val Ser Leu Ser Lys Ala Val Lys Ala Ile Asp Ala
    210                 215                 220

Gly Ala Glu Val Phe Gly Pro Val Leu Tyr Gly Phe Gly Ala Tyr Lys
225                 230                 235                 240

Asp Leu Gln Thr Ala Pro Asp Trp Asp Ser Val Lys Gly Asn Tyr Ser
                245                 250                 255

Trp Phe Val Asp Tyr Tyr Leu Asp Gln Met Arg Leu Ser Ser Gln Val
            260                 265                 270

Glu Gly Lys Arg Leu Leu Asp Val Phe Asp Val His Trp Tyr Pro Glu
        275                 280                 285

Ala Met Gly Gly Gly Ile Arg Ile Thr Asn Glu Val Gly Asn Asp Glu
    290                 295                 300

Thr Lys Lys Ala Arg Met Gln Ala Pro Arg Thr Leu Trp Asp Pro Thr
305                 310                 315                 320

Tyr Lys Glu Asp Ser Trp Ile Ala Gln Trp Phe Ser Glu Phe Leu Pro
                325                 330                 335

Ile Leu Pro Arg Leu Lys Gln Ser Val Asp Lys Tyr Tyr Pro Gly Thr
            340                 345                 350

Lys Leu Ala Met Thr Glu Tyr Ser Tyr Gly Gly Glu Asn Asp Ile Ser
        355                 360                 365

Gly Gly Ile Ala Met Thr Asp Val Leu Gly Ile Leu Gly Lys Asn Asp
    370                 375                 380

Val Tyr Met Ala Asn Tyr Trp Lys Leu Lys Asp Gly Val Asn Asn Tyr
385                 390                 395                 400

Val Ser Ala Ala Tyr Lys Leu Tyr Arg Asn Tyr Asp Gly Lys Asn Ser
                405                 410                 415

Thr Phe Gly Asp Thr Ser Val Ser Ala Gln Thr Ser Asp Ile Val Asn
            420                 425                 430

Ser Ser Val His Ala Ser Val Thr Asn Ala Ser Asp Lys Glu Leu His
        435                 440                 445

Leu Val Val Met Asn Lys Ser Met Asp Ser Ala Phe Asp Ala Gln Phe
    450                 455                 460

Asp Leu Ser Gly Ala Lys Thr Tyr Ile Ser Gly Lys Val Trp Gly Phe
465                 470                 475                 480

Asp Lys Asn Ser Ser Gln Ile Lys Glu Ala Ala Pro Ile Thr Gln Ile
                485                 490                 495

Ser Gly Asn Arg Phe Thr Tyr Thr Val Pro Pro Leu Thr Ala Tyr His
            500                 505                 510

Ile Val Leu Thr Thr Gly Asn Asp Thr Ser Pro Val
        515                 520

<210> SEQ ID NO 88
<211> LENGTH: 485
<212> TYPE: PRT
<213> ORGANISM: Bacillus sp.
```

<400> SEQUENCE: 88

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
                20                  25                  30

Asn Leu Lys Asp Lys Gly Ile Ser Ala Val Trp Ile Pro Pro Ala Trp
            35                  40                  45

Lys Gly Ala Ser Gln Asn Asp Val Gly Tyr Gly Ala Tyr Asp Leu Tyr
        50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Lys Ser
    370                 375                 380

Lys Ile Asp Pro Ile Leu Glu Ala Arg Gln Lys Tyr Ala Tyr Gly Arg
385                 390                 395                 400
```

```
Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
                420                 425                 430

Gly Ala Gly Gly Asn Lys Trp Met Phe Val Gly Arg Asn Lys Ala Gly
                435                 440                 445

Gln Val Trp Thr Asp Ile Thr Gly Asn Arg Ala Gly Thr Val Thr Ile
                450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 89
<211> LENGTH: 485
<212> TYPE: PRT
<213> ORGANISM: Bacillus sp. NCIB 12513

<400> SEQUENCE: 89

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
                20                  25                  30

Asn Leu Arg Asn Arg Gly Ile Thr Ala Ile Trp Ile Pro Pro Ala Trp
                35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp
                100                 105                 110

Ala Thr Glu Asn Val Leu Ala Val Glu Val Asn Pro Asn Asn Arg Asn
                115                 120                 125

Gln Glu Ile Ser Gly Asp Tyr Thr Ile Glu Ala Trp Thr Lys Phe Asp
130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
                180                 185                 190

Ser Glu Asn Gly Asn Tyr Asp Tyr Leu Met Tyr Ala Asp Val Asp Met
                195                 200                 205

Asp His Pro Glu Val Val Asn Glu Leu Arg Arg Trp Gly Glu Trp Tyr
                210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
                245                 250                 255

Thr Gly Lys Glu Met Phe Ala Val Ala Glu Phe Trp Lys Asn Asp Leu
                260                 265                 270
```

```
Gly Ala Leu Glu Asn Tyr Leu Asn Lys Thr Asn Trp Asn His Ser Val
            275                 280                 285

Phe Asp Val Pro Leu His Tyr Asn Leu Tyr Asn Ala Ser Asn Ser Gly
        290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
            355                 360                 365

Gly Asp Tyr Tyr Gly Ile Pro Thr His Ser Val Pro Ala Met Lys Ala
        370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
            420                 425                 430

Gly Pro Gly Gly Glu Lys Trp Met Tyr Val Gly Gln Asn Lys Ala Gly
        435                 440                 445

Gln Val Trp His Asp Ile Thr Gly Asn Lys Pro Gly Thr Val Thr Ile
            450                 455                 460

Asn Ala Asp Gly Trp Ala Asn Phe Ser Val Asn Gly Gly Ser Val Ser
465                 470                 475                 480

Ile Trp Val Lys Arg
                485

<210> SEQ ID NO 90
<211> LENGTH: 485
<212> TYPE: PRT
<213> ORGANISM: Bacillus sp. no. 707

<400> SEQUENCE: 90

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
130                 135                 140
```

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
            165                 170                 175

Ile Tyr Lys Phe Arg Gly His Gly Lys Ala Trp Asp Trp Glu Val Asp
        180                 185                 190

Thr Glu Asn Gly Asn Tyr Asp Tyr Leu Met Tyr Ala Asp Ile Asp Met
    195                 200                 205

Asp His Pro Glu Val Val Asn Glu Leu Arg Asn Trp Gly Val Trp Tyr
210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Trp Phe Lys Pro Leu Ala
            340                 345                 350

Tyr Ala Leu Thr Leu Thr Arg Glu Gln Gly Tyr Pro Ser Val Phe Tyr
            355                 360                 365

Gly Asp Tyr Tyr Gly Ile Pro Thr His Gly Val Pro Ala Met Arg Ser
370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Leu Gly Trp Thr Arg Glu
            405                 410                 415

Gly Asn Thr Ala His Pro Asn Ser Gly Leu Ala Thr Ile Met Ser Asp
            420                 425                 430

Gly Ala Gly Gly Ser Lys Trp Met Phe Val Gly Arg Asn Lys Ala Gly
        435                 440                 445

Gln Val Trp Ser Asp Ile Thr Gly Asn Arg Thr Gly Thr Val Thr Ile
    450                 455                 460

Asn Ala Asp Gly Trp Gly Asn Phe Ser Val Asn Gly Ser Val Ser
465                 470                 475                 480

Ile Trp Val Asn Lys
                485

<210> SEQ ID NO 91
<211> LENGTH: 485
<212> TYPE: PRT
<213> ORGANISM: artificial
<220> FEATURE:
<223> OTHER INFORMATION: fusion protein

<400> SEQUENCE: 91

His His Asp Gly Thr Asn Gly Thr Ile Met Gln Tyr Phe Glu Trp Asn
1               5                   10                  15

```
Val Pro Asn Asp Gly Gln His Trp Asn Arg Leu His Asn Asn Ala Gln
         20                  25                  30

Asn Leu Lys Asn Ala Gly Ile Thr Ala Ile Trp Ile Pro Pro Ala Trp
         35                  40                  45

Lys Gly Thr Ser Gln Asn Asp Val Gly Tyr Ala Tyr Asp Leu Tyr
 50                  55                  60

Asp Leu Gly Glu Phe Asn Gln Lys Gly Thr Val Arg Thr Lys Tyr Gly
65                   70                  75                  80

Thr Lys Ala Glu Leu Glu Arg Ala Ile Arg Ser Leu Lys Ala Asn Gly
             85                  90                  95

Ile Gln Val Tyr Gly Asp Val Val Met Asn His Lys Gly Gly Ala Asp
             100                 105                 110

Phe Thr Glu Arg Val Gln Ala Val Glu Val Asn Pro Gln Asn Arg Asn
             115                 120                 125

Gln Glu Val Ser Gly Thr Tyr Gln Ile Glu Ala Trp Thr Gly Phe Asn
130                 135                 140

Phe Pro Gly Arg Gly Asn Gln His Ser Ser Phe Lys Trp Arg Trp Tyr
145                 150                 155                 160

His Phe Asp Gly Thr Asp Trp Asp Gln Ser Arg Gln Leu Ala Asn Arg
                 165                 170                 175

Ile Tyr Lys Phe Arg Gly Asp Gly Lys Ala Trp Asp Trp Glu Val Asp
                 180                 185                 190

Thr Glu Asn Gly Asn Tyr Asp Tyr Leu Met Tyr Ala Asp Val Asp Met
                 195                 200                 205

Asp His Pro Glu Val Ile Asn Glu Leu Asn Arg Trp Gly Val Trp Tyr
                 210                 215                 220

Ala Asn Thr Leu Asn Leu Asp Gly Phe Arg Leu Asp Ala Val Lys His
225                 230                 235                 240

Ile Lys Phe Ser Phe Met Arg Asp Trp Leu Gly His Val Arg Gly Gln
                 245                 250                 255

Thr Gly Lys Asn Leu Phe Ala Val Ala Glu Tyr Trp Lys Asn Asp Leu
                 260                 265                 270

Gly Ala Leu Glu Asn Tyr Leu Ser Lys Thr Asn Trp Thr Met Ser Ala
             275                 280                 285

Phe Asp Val Pro Leu His Tyr Asn Leu Tyr Gln Ala Ser Asn Ser Ser
290                 295                 300

Gly Asn Tyr Asp Met Arg Asn Leu Leu Asn Gly Thr Leu Val Gln Arg
305                 310                 315                 320

His Pro Ser His Ala Val Thr Phe Val Asp Asn His Asp Thr Gln Pro
                 325                 330                 335

Gly Glu Ala Leu Glu Ser Phe Val Gln Gly Trp Phe Lys Pro Leu Ala
             340                 345                 350

Tyr Ala Thr Ile Leu Thr Arg Glu Gln Gly Tyr Pro Gln Val Phe Tyr
             355                 360                 365

Gly Asp Tyr Tyr Gly Ile Pro Ser Asp Gly Val Pro Ser Tyr Arg Gln
             370                 375                 380

Gln Ile Asp Pro Leu Leu Lys Ala Arg Gln Gln Tyr Ala Tyr Gly Thr
385                 390                 395                 400

Gln His Asp Tyr Leu Asp Asn Gln Asp Val Ile Gly Trp Thr Arg Glu
                 405                 410                 415

Gly Asp Ser Ala His Ala Gly Ser Gly Leu Ala Thr Val Met Ser Asp
                 420                 425                 430
```

-continued

```
Gly Pro Gly Gly Ser Lys Thr Met Tyr Val Gly Thr Ala His Ala Gly
            435                 440                 445

Gln Val Phe Lys Asp Ile Thr Gly Asn Arg Thr Asp Thr Val Thr Ile
        450                 455                 460

Asn Ser Ala Gly Asn Gly Thr Phe Pro Cys Asn Gly Gly Ser Val Ser
465                 470                 475                 480

Ile Trp Val Lys Gln
                485
```